(12) United States Patent
Schaefer et al.

(10) Patent No.: US 11,913,945 B2
(45) Date of Patent: Feb. 27, 2024

(54) METHOD FOR DETERMINING THE AMOUNT OF A THERAPEUTIC ANTIBODY IN THE BRAIN

(71) Applicant: Hoffmann-La Roche Inc., Little Falls, NJ (US)

(72) Inventors: Martin Schaefer, Penzberg (DE); Sylvia Rottach, Penzberg (DE); Gregor Jordan, Penzberg (DE); Kay-Gunnar Stubenrauch, Penzberg (DE); Roland Staack, Penzberg (DE); Kevin Brady, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 35 days.

(21) Appl. No.: 17/136,289

(22) Filed: Dec. 29, 2020

(65) Prior Publication Data
US 2021/0364504 A1 Nov. 25, 2021

(30) Foreign Application Priority Data
Jan. 2, 2020 (EP) .................................... 20150135

(51) Int. Cl.
*G01N 33/543* (2006.01)
*C07K 16/28* (2006.01)
*C07K 16/40* (2006.01)
*G01N 33/68* (2006.01)

(52) U.S. Cl.
CPC ....... *G01N 33/543* (2013.01); *C07K 16/2803* (2013.01); *C07K 16/2881* (2013.01); *C07K 16/2887* (2013.01); *C07K 16/40* (2013.01); *G01N 33/54306* (2013.01); *G01N 33/6854* (2013.01); *C07K 2317/31* (2013.01); *G01N 2800/52* (2013.01)

(58) Field of Classification Search
None
See application file for complete search history.

(56) References Cited

U.S. PATENT DOCUMENTS

| 2018/0002433 A1 | 1/2018 | Zhang et al. |
| 2022/0357340 A1* | 11/2022 | Brady ................ G01N 33/5088 |

FOREIGN PATENT DOCUMENTS

| CA | 3000560 A1 | 4/2017 |
| EP | 0580979 A2 | 2/1994 |
| WO | 90/005301 A1 | 5/1990 |
| WO | 90/11511 A1 | 10/1990 |
| WO | 92/14128 A1 | 8/1992 |
| WO | 2015/131256 A1 | 9/2015 |
| WO | 2015/131257 A1 | 9/2015 |
| WO | 2015/131258 A1 | 9/2015 |
| WO | 2018/152359 A1 | 8/2018 |

OTHER PUBLICATIONS

Lloyd et al., Protein Engineering, Design & Selection 22:159-168 (Year: 2009).*
Edwards et al., J Mol Biol 14;334(1): 103-118 (Year: 2003).*
Abuqayyas, L., et al., "Investigation of the Role of FcγR and FcRn in mAb Distribution to the Brain" ACS Mole Pharmaceutics 10(5):1505-1513 (Jul. 12, 2012).
Aslam, M. et al. Bioconjugation: Protein Coupling Techniques for the Biomedical Sciences "Chapter 2: The Functional Chemistry of Proteins and Protein Coupling" Aslam, M, & Dent, A., eds, First edition, London, GB:MacMillian Reference Limited,:50-100 (Jan. 1, 1998).
Aspelund, A., et al., "A dural lymphatic vascular system that drains brain interstitial fluid and macromolecules" J Exp Med 212(7):991-999 (Jun. 15, 2015).
Bien-Ly, N., et al., "Transferrin receptor (TfR) trafficking determines brain uptake of TfR antibody affinity variants" J Exp Med 211(2):233-244 (Feb. 10, 2014).
Cooper, P.R., et al., "Efflux of monoclonal antibodies from rat brain by neonatal Fc receptor, FcRn" Brain Res 1534:13-21 (Oct. 9, 2013).
Deane, R., et al., "IgG-Assisted Age-Dependent Clearance of Alzheimer's Amyloid β Peptide by the Blood-Brain Barrier Neonatal Fc Receptor" J Neurosci 25(50):11495-11503 (Dec. 14, 2005).
Friden, M., et al., "Improved measurement of drug exposure in the brain using drug-specific correction for residual blood" J Celeb Blood Flow Metab 30(1):150-161 (Jan. 1, 2010).
Hage, D.S., "Immunoassays" Anal Chem 71(12):294R-304R (May 20, 1999).
Janowicz, P.W., et al., "Ultrasound-mediated blood-brain barrier opening enhances delivery of therapeutically relevant formats of a tau-specific antibody" Sci Rep 9(9255):1-9 (Jun. 25, 2019).
Louveau, A., et al., "Structural and functional features of central nervous system lymphatics" Nature 523(7560):337-341 (Jul. 16, 2015).
Lu, B., et al., "Tutorial review. Oriented immobilization of antibodies and its applications in immunoassays and immunosensors" Analyst 121(3):29R-32R (Mar. 1, 1996).
Neuwelt, E., et al., "Engaging neuroscience to advance translational research in brain barrier biology" Nat Rev Neurosci 12(3):179-182 (Mar. 1, 2022).
Schlachetzki, F., et al., "Expression of the neonatal Fc receptor (FcRn) at the blood-brain barrier" J Neurochem 81(1):203-206 (Apr. 1, 2002).
Vidarte, L.,, "Serine 132 is the C3 Covalent Attachment Point on the CH1 Domain of Human IgG1" J Biol Chem 276(41):38217-38223 (Oct. 12, 2001).

(Continued)

*Primary Examiner* — Phuong Huynh
(74) *Attorney, Agent, or Firm* — Yan Qi

(57) ABSTRACT

Herein is reported a method for determining the concentration of a therapeutic antibody in a tissue of an experimental animal to whom the therapeutic antibody had been administered, wherein the interference from residual blood in a tissue sample of the experimental animal, which is used for determining the concentration of the therapeutic antibody in said tissue, is reduced by applying an inert reference antibody that does not penetrate into said tissue, whereby the inert reference antibody is administered 2 to 10 minutes prior to obtaining the tissue and blood sample.

14 Claims, 13 Drawing Sheets

Specification includes a Sequence Listing.

(56) References Cited

OTHER PUBLICATIONS

Wilchek, M., et al. Methods in Enzymology "Chapter 54: Avidin-biotin Mediated Immunoassays: Overview" Wilchek, M. & Bayer, E. eds., New York, NY USA:Academic Press, Inc.—Elsevier BV., vol. 184:467-469 ( 1990).

Zhang, Y., et al., "Mediated efflux of IgG molecules from brain to blood across the blood-brain barrier" J Neuroimmunol 114(1-2):168-172 (Mar. 1, 2001).

Ayabe, M., et al., "Non-labelling approach for absolute quantitation of total biotherapeutics and simultaneous detection of blood volume in tissues using LC/MS" Poster (Poster-TP604) 67th ASMS Conference on Mass Spectrometry and Allied Topics, Atlanta, Georgia—US, pp. 1 ( Jun. 2-6, 2019).

Hanzatian, D., et al., "Brain uptake of multivalent and multi-specific DVD-Ig proteins after systemic administration" MABS 10(5):765-777 (Jul. 1, 2018).

"International Preliminary Report on Patentability—PCT/EP2020/087965" (Report dated Jul. 5, 2022; Chapter I) ,:pp. 1-7 (Jul. 14, 2022).

"International Search Report—PCT/EP2020/087965" (w/Written Opinion), :pp. 1-13 (dated Mar. 12, 2021).

Katsinelos, T., et al., "The Role of Antibodies and Their Receptors in Protection Against Ordered Protein Assembly in Neurodegeneration" Front Immunol 10(1139):1-15 (May 31, 2019).

Lavezzi, S.M., et al., "MPBPK-TMDD models for mAbs: alternative models, comparison, and identifiability issues" J Pharmacokinet Pharmacodyn 45(6):787-802 (Dec. 1, 2018).

Shah, D., et al., "Antibody biodistribution coefficients: Inferring tissue concentrations of monoclonal antibodies based on the plasma concentrations in several preclinical species and human" MABS 5(2):297-305 (Mar. 1, 2013).

Vedeler, C.A., et al., "Immunoglobulins in serum and cerebrospinal fluid from patients with acute Guillain-Barré syndrome" Acta Neurol Scand 73(4):388-393 (Apr. 1, 1986).

Zuchero, Y., et al., "Discovery of novel blood-brain barrier targets to enhance brain uptake of therapeutic antibodies" Neuron 89(1):70-82 (Jan. 6, 2016).

Fröhlich, E et al., "Structure and function of blood-tissue barriers" Dtsch Med Wochenschr 127 pp. 2629-2634 ( 2002) (With English Translation).

* cited by examiner

SEQUENCE LISTING

<160> NUMBER OF SEQ ID NOS: 70

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2

```
<211> LENGTH: 20
<212> TYPE: PRT
<213> ORGANISM: Artificial Sequence
<220> FEATURE:
<223> OTHER INFORMATION: (G4S)4 linker

<400> SEQUENCE: 2

Gly Gly Gly Gly Ser Gly Gly Gly Gly Ser Gly Gly Gly Gly Ser Gly
1               5                   10                  15

Gly Gly Gly Ser
            20

<210> SEQ ID NO 3
<211> LENGTH: 32
<212> TYPE: PRT
<213> ORGANISM: Artificial Sequence
<220> FEATURE:
<223> OTHER INFORMATION: (G4S)6G2 linker

<400> SEQUENCE: 3

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Ser Gly Gly
            20                  25                  30

<210> SEQ ID NO 4
<211> LENGTH: 215
<212> TYPE: PRT
<213> ORGANISM: Artificial Sequence
<220> FEATURE:
<223> OTHER INFORMATION: 0012-LC1

<400> SEQUENCE: 4

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Arg Lys Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

```
Ser Phe Asn Arg Gly Glu Cys
    210                 215
```

```
<210> SEQ ID NO 5
<211> LENGTH: 455
<212> TYPE: PRT
<213> ORGANISM: Artificial Sequence
<220> FEATURE:
<223> OTHER INFORMATION: 0012-HC1

<400> SEQUENCE: 5

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Glu Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350
```

```
Arg Glu Pro Gln Val Cys Thr Leu Pro Pro Ser Arg Asp Glu Leu Thr
            355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
    435                 440                 445

Ser Leu Ser Leu Ser Pro Gly
    450                 455

<210> SEQ ID NO 6
<211> LENGTH: 229
<212> TYPE: PRT
<213> ORGANISM: Artificial Sequence
<220> FEATURE:
<223> OTHER INFORMATION: 0012-LC2

<400> SEQUENCE: 6

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30

Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Lys Thr Ser Thr Val Ser Leu Lys Leu Ser
65                  70                  75                  80

Ser Val Thr Ala Ala Asp Thr Ala Val Tyr Tyr Cys Ala Arg Arg Tyr
                85                  90                  95

Gly Thr Ser Tyr Pro Asp Tyr Gly Asp Ala Ser Gly Phe Asp Pro Trp
            100                 105                 110

Gly Gln Gly Thr Leu Val Thr Val Ser Ser Ala Ser Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225

<210> SEQ ID NO 7
<211> LENGTH: 688
```

```
<212> TYPE: PRT
<213> ORGANISM: Artificial Sequence
<220> FEATURE:
<223> OTHER INFORMATION: 0012-HC2

<400> SEQUENCE: 7
```

| | | | | | | | | | | | | | | |
|---|---|---|---|---|---|---|---|---|---|---|---|---|---|---|
|Gln|Val|Glu|Leu|Val|Glu|Ser|Gly|Gly|Gly|Leu|Val|Gln|Pro|Gly|Gly|
|1| | |  |5| | | | |10| | | | |15|

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Glu Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Asp Glu Leu Thr
        355                 360                 365

Lys Asn Gln Val Ser Leu Trp Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly Gly Ser Gly Gly Gly Gly Ser Gly
    450                 455                 460

Gly Gly Gly Ser Gly Gly Gly Ser Ala Ile Gln Leu Thr Gln Ser
465                 470                 475                 480

Pro Ser Ser Leu Ser Ala Ser Val Gly Asp Arg Val Thr Ile Thr Cys
            485                 490                 495

Arg Ala Ser Gln Ser Ile Ser Ser Tyr Leu Ala Trp Tyr Gln Gln Lys
        500                 505                 510

Pro Gly Lys Ala Pro Lys Leu Leu Ile Tyr Arg Ala Ser Thr Leu Ala
    515                 520                 525

Ser Gly Val Pro Ser Arg Phe Ser Gly Ser Gly Ser Gly Thr Asp Phe
530                 535                 540

Thr Leu Thr Ile Ser Ser Leu Gln Pro Glu Asp Phe Ala Thr Tyr Tyr
545                 550                 555                 560

Cys Gln Gln Asn Tyr Ala Ser Ser Asn Val Asp Asn Thr Phe Gly Gly
            565                 570                 575

Gly Thr Lys Val Glu Ile Lys Ser Ser Ala Ser Thr Lys Gly Pro Ser
        580                 585                 590

Val Phe Pro Leu Ala Pro Ser Ser Lys Ser Thr Ser Gly Gly Thr Ala
    595                 600                 605

Ala Leu Gly Cys Leu Val Lys Asp Tyr Phe Pro Glu Pro Val Thr Val
    610                 615                 620

Ser Trp Asn Ser Gly Ala Leu Thr Ser Gly Val His Thr Phe Pro Ala
625                 630                 635                 640

Val Leu Gln Ser Ser Gly Leu Tyr Ser Leu Ser Ser Val Val Thr Val
            645                 650                 655

Pro Ser Ser Ser Leu Gly Thr Gln Thr Tyr Ile Cys Asn Val Asn His
        660                 665                 670

Lys Pro Ser Asn Thr Lys Val Asp Lys Lys Val Glu Pro Lys Ser Cys
    675                 680                 685

<210> SEQ ID NO 8
<211> LENGTH: 215
<212> TYPE: PRT
<213> ORGANISM: Artificial Sequence
<220> FEATURE:
<223> OTHER INFORMATION: 0015-LC1

<400> SEQUENCE: 8

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
            85                  90                  95

Ile Thr Phe Gly Gln Gly Thr Lys Val Glu Ile Lys Arg Thr Val Ala
        100                 105                 110

Ala Pro Ser Val Phe Ile Phe Pro Pro Ser Asp Arg Lys Leu Lys Ser
    115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215

<210> SEQ ID NO 9
<211> LENGTH: 455
<212> TYPE: PRT
<213> ORGANISM: Artificial Sequence
<220> FEATURE:
<223> OTHER INFORMATION: 0015-HC1

<400> SEQUENCE: 9

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Lys Gly Asn Thr His Lys Pro Tyr Gly Tyr Val Arg Tyr
        100                 105                 110

Phe Asp Val Trp Gly Gln Gly Thr Leu Val Thr Val Ser Ser Ala Ser
    115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
        180                 185                 190

Ser Val Val Thr Val Pro Ser Ser Ser Leu Gly Thr Gln Thr Tyr Ile
    195                 200                 205

```
Cys Asn Val Asn His Lys Pro Ser Asn Thr Lys Val Asp Glu Lys Val
    210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
                260                 265                 270
Val Asp Val Ser His Glu Asp Pro Glu Val Lys Phe Asn Trp Tyr Val
                275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
                340                 345                 350
Arg Glu Pro Gln Val Cys Thr Leu Pro Pro Ser Arg Asp Glu Leu Thr
    355                 360                 365
Lys Asn Gln Val Ser Leu Ser Cys Ala Val Lys Gly Phe Tyr Pro Ser
370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Val
                405                 410                 415
Ser Lys Leu Thr Val Asp Lys Ser Arg Trp Gln Gln Gly Asn Val Phe
                420                 425                 430
Ser Cys Ser Val Met His Glu Ala Leu His Asn His Tyr Thr Gln Lys
    435                 440                 445
Ser Leu Ser Leu Ser Pro Gly
    450                 455

<210> SEQ ID NO 10
<211> LENGTH: 215
<212> TYPE: PRT
<213> ORGANISM: Artificial Sequence
<220> FEATURE:
<223> OTHER INFORMATION: 0015-LC2

<400> SEQUENCE: 10

Ala Ile Gln Leu Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
                20                  25                  30
Leu Ala Trp Tyr Gln Gln Lys Pro Gly Lys Ala Pro Lys Leu Leu Ile
            35                  40                  45
Tyr Arg Ala Ser Thr Leu Ala Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Asn Tyr Ala Ser Ser Asn
                85                  90                  95
Val Asp Asn Thr Phe Gly Gly Gly Thr Lys Val Glu Ile Lys Ser Ser
                100                 105                 110
```

```
Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Leu Gly Thr Gln Thr
            180                 185                 190

Tyr Ile Cys Asn Val Asn His Lys Pro Ser Asn Thr Lys Val Asp Lys
            195                 200                 205

Lys Val Glu Pro Lys Ser Cys
210                 215

<210> SEQ ID NO 11
<211> LENGTH: 702
<212> TYPE: PRT
<213> ORGANISM: Artificial Sequence
<220> FEATURE:
<223> OTHER INFORMATION: 0015-HC2

<400> SEQUENCE: 11

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Glu Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255
```

-continued

```
Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Asp Glu Leu Thr
        355                 360                 365

Lys Asn Gln Val Ser Leu Trp Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Gly Ser Gly Gly Gly Gly Ser Gly
    450                 455                 460

Gly Gly Gly Ser Gly Gly Gly Ser Gln Ser Met Gln Glu Ser Gly
465                 470                 475                 480

Pro Gly Leu Val Lys Pro Ser Gln Thr Leu Ser Leu Thr Cys Thr Val
                485                 490                 495

Ser Gly Phe Ser Leu Ser Ser Tyr Ala Met Ser Trp Ile Arg Gln His
            500                 505                 510

Pro Gly Lys Gly Leu Glu Trp Ile Gly Tyr Ile Trp Ser Gly Gly Ser
        515                 520                 525

Thr Asp Tyr Ala Ser Trp Ala Lys Ser Arg Val Thr Ile Ser Lys Thr
    530                 535                 540

Ser Thr Thr Val Ser Leu Lys Leu Ser Ser Val Thr Ala Ala Asp Thr
545                 550                 555                 560

Ala Val Tyr Tyr Cys Ala Arg Arg Tyr Gly Thr Ser Tyr Pro Asp Tyr
                565                 570                 575

Gly Asp Ala Ser Gly Phe Asp Pro Trp Gly Gln Gly Thr Leu Val Thr
            580                 585                 590

Val Ser Ser Ala Ser Val Ala Ala Pro Ser Val Phe Ile Phe Pro Pro
        595                 600                 605

Ser Asp Glu Gln Leu Lys Ser Gly Thr Ala Ser Val Val Cys Leu Leu
    610                 615                 620

Asn Asn Phe Tyr Pro Arg Glu Ala Lys Val Gln Trp Lys Val Asp Asn
625                 630                 635                 640

Ala Leu Gln Ser Gly Asn Ser Gln Glu Ser Val Thr Glu Gln Asp Ser
                645                 650                 655

Lys Asp Ser Thr Tyr Ser Leu Ser Ser Thr Leu Thr Leu Ser Lys Ala
            660                 665                 670
```

Asp Tyr Glu Lys His Lys Val Tyr Ala Cys Glu Val Thr His Gln Gly
            675                 680                 685

Leu Ser Ser Pro Val Thr Lys Ser Phe Asn Arg Gly Glu Cys
        690                 695                 700

<210> SEQ ID NO 12
<211> LENGTH: 215
<212> TYPE: PRT
<213> ORGANISM: Artificial Sequence
<220> FEATURE:
<223> OTHER INFORMATION: 0020-LC1

<400> SEQUENCE: 12

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Arg Lys Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 13
<211> LENGTH: 457
<212> TYPE: PRT
<213> ORGANISM: Artificial Sequence
<220> FEATURE:
<223> OTHER INFORMATION: 0020-HC1

<400> SEQUENCE: 13

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Lys Gly Asn Thr His Lys Pro Tyr Gly Tyr Val Arg Tyr
            100                 105                 110
Phe Asp Val Trp Gly Gln Gly Thr Leu Val Thr Val Ser Ser Ala Ser
            115                 120                 125
Thr Lys Gly Pro Ser Val Phe Pro Leu Ala Pro Ser Ser Lys Ser Thr
130                 135                 140
Ser Gly Gly Thr Ala Ala Leu Gly Cys Leu Val Glu Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Leu Gly Thr Gln Thr Tyr Ile
            195                 200                 205
Cys Asn Val Asn His Lys Pro Ser Asn Thr Lys Val Asp Glu Lys Val
            210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
            275                 280                 285
Asp Gly Val Glu Val His Asn Ala Lys Thr Lys Pro Arg Glu Glu Gln
            290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Cys Thr Leu Pro Pro Ser Arg Asp Glu Leu Thr
            355                 360                 365
Lys Asn Gln Val Ser Leu Ser Cys Ala Val Lys Gly Phe Tyr Pro Ser
370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Val
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
            435                 440                 445
Ser Leu Ser Leu Ser Pro Gly Lys Gly
450                 455

```
<210> SEQ ID NO 14
<211> LENGTH: 947
<212> TYPE: PRT
<213> ORGANISM: Artificial Sequence
<220> FEATURE:
<223> OTHER INFORMATION: 0020-HC2

<400> SEQUENCE: 14

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Glu Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Asp Glu Leu Thr
        355                 360                 365
```

-continued

```
Lys Asn Gln Val Ser Leu Trp Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Gly Ser Gly Gly Gly Gly Ser Gly
450                 455                 460

Gly Gly Ser Gly Gly Gly Gly Ser Ala Ile Gln Leu Thr Gln Ser
465                 470                 475                 480

Pro Ser Ser Leu Ser Ala Ser Val Gly Asp Arg Val Thr Ile Thr Cys
                485                 490                 495

Arg Ala Ser Gln Ser Ile Ser Ser Tyr Leu Ala Trp Tyr Gln Gln Lys
                500                 505                 510

Pro Gly Lys Ala Pro Lys Leu Leu Ile Tyr Arg Ala Ser Thr Leu Ala
                515                 520                 525

Ser Gly Val Pro Ser Arg Phe Ser Gly Ser Gly Ser Gly Thr Asp Phe
530                 535                 540

Thr Leu Thr Ile Ser Ser Leu Gln Pro Glu Asp Phe Ala Thr Tyr Tyr
545                 550                 555                 560

Cys Gln Gln Asn Tyr Ala Ser Ser Asn Val Asp Asn Thr Phe Gly Gly
                565                 570                 575

Gly Thr Lys Val Glu Ile Lys Arg Thr Val Ala Ala Pro Ser Val Phe
                580                 585                 590

Ile Phe Pro Pro Ser Asp Glu Gln Leu Lys Ser Gly Thr Ala Ser Val
                595                 600                 605

Val Cys Leu Leu Asn Asn Phe Tyr Pro Arg Glu Ala Lys Val Gln Trp
610                 615                 620

Lys Val Asp Asn Ala Leu Gln Ser Gly Asn Ser Gln Glu Ser Val Thr
625                 630                 635                 640

Glu Gln Asp Ser Lys Asp Ser Thr Tyr Ser Leu Ser Ser Thr Leu Thr
                645                 650                 655

Leu Ser Lys Ala Asp Tyr Glu Lys His Lys Val Tyr Ala Cys Glu Val
                660                 665                 670

Thr His Gln Gly Leu Ser Ser Pro Val Thr Lys Ser Phe Asn Arg Gly
            675                 680                 685

Glu Cys Gly Gly Gly Gly Ser Gly Gly Gly Gly Ser Gly Gly Gly Gly
            690                 695                 700

Ser Gly Gly Gly Gly Ser Gly Gly Gly Gly Ser Gly Gly Gly Gly Ser
705                 710                 715                 720

Gly Gly Gln Ser Met Gln Glu Ser Gly Pro Gly Leu Val Lys Pro Ser
                725                 730                 735

Gln Thr Leu Ser Leu Thr Cys Thr Val Ser Gly Phe Ser Leu Ser Ser
                740                 745                 750

Tyr Ala Met Ser Trp Ile Arg Gln His Pro Gly Lys Gly Leu Glu Trp
            755                 760                 765

Ile Gly Tyr Ile Trp Ser Gly Gly Ser Thr Asp Tyr Ala Ser Trp Ala
770                 775                 780
```

```
Lys Ser Arg Val Thr Ile Ser Lys Thr Ser Thr Val Ser Leu Lys
785                 790                 795                 800

Leu Ser Ser Val Thr Ala Ala Asp Thr Ala Val Tyr Tyr Cys Ala Arg
            805                 810                 815

Arg Tyr Gly Thr Ser Tyr Pro Asp Tyr Gly Asp Ala Ser Gly Phe Asp
        820                 825                 830

Pro Trp Gly Gln Gly Thr Leu Val Thr Val Ser Ser Ala Ser Thr Lys
    835                 840                 845

Gly Pro Ser Val Phe Pro Leu Ala Pro Ser Ser Lys Ser Thr Ser Gly
850                 855                 860

Gly Thr Ala Ala Leu Gly Cys Leu Val Lys Asp Tyr Phe Pro Glu Pro
865                 870                 875                 880

Val Thr Val Ser Trp Asn Ser Gly Ala Leu Thr Ser Gly Val His Thr
            885                 890                 895

Phe Pro Ala Val Leu Gln Ser Ser Gly Leu Tyr Ser Leu Ser Ser Val
        900                 905                 910

Val Thr Val Pro Ser Ser Ser Leu Gly Thr Gln Thr Tyr Ile Cys Asn
    915                 920                 925

Val Asn His Lys Pro Ser Asn Thr Lys Val Asp Lys Lys Val Glu Pro
    930                 935                 940

Lys Ser Cys
945

<210> SEQ ID NO 15
<211> LENGTH: 215
<212> TYPE: PRT
<213> ORGANISM: Artificial Sequence
<220> FEATURE:
<223> OTHER INFORMATION: 0024-LC1

<400> SEQUENCE: 15

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
            85                  90                  95

Ile Thr Phe Gly Gln Gly Thr Lys Val Glu Ile Lys Arg Thr Val Ala
        100                 105                 110

Ala Pro Ser Val Phe Ile Phe Pro Pro Ser Asp Glu Gln Leu Lys Ser
    115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190
```

```
Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 16
<211> LENGTH: 455
<212> TYPE: PRT
<213> ORGANISM: Artificial Sequence
<220> FEATURE:
<223> OTHER INFORMATION: 0024-HC1

<400> SEQUENCE: 16

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335
```

```
Leu Pro Ala Pro Ile Glu Lys Thr Ile Ser Lys Ala Lys Gly Gln Pro
            340                 345                 350

Arg Glu Pro Gln Val Cys Thr Leu Pro Pro Ser Arg Asp Glu Leu Thr
            355                 360                 365

Lys Asn Gln Val Ser Leu Ser Cys Ala Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly
            450                 455

<210> SEQ ID NO 17
<211> LENGTH: 215
<212> TYPE: PRT
<213> ORGANISM: Artificial Sequence
<220> FEATURE:
<223> OTHER INFORMATION: 0024-LC2

<400> SEQUENCE: 17

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95

Val Asp Asn Thr Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys
    210                 215

<210> SEQ ID NO 18
```

<211> LENGTH: 702
<212> TYPE: PRT
<213> ORGANISM: Artificial Sequence
<220> FEATURE:
<223> OTHER INFORMATION: 0024-HC2

<400> SEQUENCE: 18

```
Gln Val Glu Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Ser Tyr
             20                  25                  30
Ala Met Ser Trp Val Arg Gln Ala Pro Gly Lys Gly Leu Glu Trp Val
         35                  40                  45
Ser Ala Ile Asn Ala Ser Gly Thr Arg Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Lys Gly Asn Thr His Lys Pro Tyr Gly Tyr Val Arg Tyr
            100                 105                 110
Phe Asp Val Trp Gly Gln Gly Thr Leu Val Thr Val Ser Ser Ala Ser
        115                 120                 125
Thr Lys Gly Pro Ser Val Phe Pro Leu Ala Pro Ser Ser Lys Ser Thr
    130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Lys Val
    210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Cys Arg Asp Glu Leu Thr
        355                 360                 365
Lys Asn Gln Val Ser Leu Trp Cys Leu Val Lys Gly Phe Tyr Pro Ser
    370                 375                 380
```

```
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly Gly Ser Gly Gly Gly Ser Gly
450                 455                 460

Gly Gly Gly Ser Gly Gly Gly Ser Gln Ser Met Gln Glu Ser Gly
465                 470                 475                 480

Pro Gly Leu Val Lys Pro Ser Gln Thr Leu Ser Leu Thr Cys Thr Val
            485                 490                 495

Ser Gly Phe Ser Leu Ser Ser Tyr Ala Met Ser Trp Ile Arg Gln His
        500                 505                 510

Pro Gly Lys Gly Leu Glu Trp Ile Gly Tyr Ile Trp Ser Gly Gly Ser
    515                 520                 525

Thr Asp Tyr Ala Ser Trp Ala Lys Ser Arg Val Thr Ile Ser Lys Thr
530                 535                 540

Ser Thr Thr Val Ser Leu Lys Leu Ser Ser Val Thr Ala Ala Asp Thr
545                 550                 555                 560

Ala Val Tyr Tyr Cys Ala Arg Arg Tyr Gly Thr Ser Tyr Pro Asp Tyr
            565                 570                 575

Gly Asp Ala Ser Gly Phe Asp Pro Trp Gly Gln Gly Thr Leu Val Thr
        580                 585                 590

Val Ser Ser Ala Ser Val Ala Ala Pro Ser Val Phe Ile Phe Pro Pro
    595                 600                 605

Ser Asp Glu Gln Leu Lys Ser Gly Thr Ala Ser Val Val Cys Leu Leu
    610                 615                 620

Asn Asn Phe Tyr Pro Arg Glu Ala Lys Val Gln Trp Lys Val Asp Asn
625                 630                 635                 640

Ala Leu Gln Ser Gly Asn Ser Gln Glu Ser Val Thr Glu Gln Asp Ser
            645                 650                 655

Lys Asp Ser Thr Tyr Ser Leu Ser Ser Thr Leu Thr Leu Ser Lys Ala
        660                 665                 670

Asp Tyr Glu Lys His Lys Val Tyr Ala Cys Glu Val Thr His Gln Gly
    675                 680                 685

Leu Ser Ser Pro Val Thr Lys Ser Phe Asn Arg Gly Glu Cys
    690                 695                 700

<210> SEQ ID NO 19
<211> LENGTH: 126
<212> TYPE: PRT
<213> ORGANISM: Homo sapiens

<400> SEQUENCE: 19

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Asn Ala Ser Gly Thr Arg Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Lys Gly Asn Thr His Lys Pro Tyr Gly Tyr Val Arg Tyr
             100                 105                 110

Phe Asp Val Trp Gly Gln Gly Thr Leu Val Thr Val Ser Ser
             115                 120                 125

<210> SEQ ID NO 20
<211> LENGTH: 108
<212> TYPE: PRT
<213> ORGANISM: Homo sapiens

<400> SEQUENCE: 20

Asp Ile Val Leu Thr Gln Ser Pro Ala Thr Leu Ser Leu Ser Pro Gly
 1               5                   10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Leu Gln Ile Tyr Asn Met Pro
                 85                  90                  95

Ile Thr Phe Gly Gln Gly Thr Lys Val Glu Ile Lys
            100                 105

<210> SEQ ID NO 21
<211> LENGTH: 122
<212> TYPE: PRT
<213> ORGANISM: Artificial Sequence
<220> FEATURE:
<223> OTHER INFORMATION: 299-023 VH humanization variant_DASG

<400> SEQUENCE: 21

Gln Ser Met Gln Glu Ser Gly Pro Gly Leu Val Lys Pro Ser Gln Thr
 1               5                   10                  15

Leu Ser Leu Thr Cys Thr Val Ser Gly Phe Ser Leu Ser Ser Tyr Ala
             20                  25                  30

Met Ser Trp Ile Arg Gln His Pro Gly Lys Gly Leu Glu Trp Ile Gly
         35                  40                  45

Tyr Ile Trp Ser Gly Gly Ser Thr Asp Tyr Ala Ser Trp Ala Lys Ser
     50                  55                  60

Arg Val Thr Ile Ser Lys Thr Ser Thr Thr Val Ser Leu Lys Leu Ser
 65                  70                  75                  80

Ser Val Thr Ala Ala Asp Thr Ala Val Tyr Tyr Cys Ala Arg Arg Tyr
                 85                  90                  95

Gly Thr Ser Tyr Pro Asp Tyr Gly Asp Ala Ser Gly Phe Asp Pro Trp
            100                 105                 110

Gly Gln Gly Thr Leu Val Thr Val Ser Ser
            115                 120
```

```
<210> SEQ ID NO 22
<211> LENGTH: 110
<212> TYPE: PRT
<213> ORGANISM: Artificial Sequence
<220> FEATURE:
<223> OTHER INFORMATION: 299-009 VL humanization variant_NYA

<400> SEQUENCE: 22

Ala Ile Gln Leu Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95

Val Asp Asn Thr Phe Gly Gly Gly Thr Lys Val Glu Ile Lys
            100                 105                 110

<210> SEQ ID NO 23
<211> LENGTH: 215
<212> TYPE: PRT
<213> ORGANISM: Artificial Sequence
<220> FEATURE:
<223> OTHER INFORMATION: 0015-LC1

<400> SEQUENCE: 23

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Arg Lys Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

Ser Phe Asn Arg Gly Glu Cys
    210                 215

<210> SEQ ID NO 24
<211> LENGTH: 455
<212> TYPE: PRT
<213> ORGANISM: Artificial Sequence
<220> FEATURE:
<223> OTHER INFORMATION: 0015-HC1

<400> SEQUENCE: 24

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Glu Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

```
Arg Glu Pro Gln Val Cys Thr Leu Pro Pro Ser Arg Asp Glu Leu Thr
            355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly
            450                 455

<210> SEQ ID NO 25
<211> LENGTH: 215
<212> TYPE: PRT
<213> ORGANISM: Artificial Sequence
<220> FEATURE:
<223> OTHER INFORMATION: 0015-LC2

<400> SEQUENCE: 25

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95

Val Asp Asn Thr Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys
    210                 215

<210> SEQ ID NO 26
<211> LENGTH: 229
<212> TYPE: PRT
<213> ORGANISM: Artificial Sequence
```

```
<220> FEATURE:
<223> OTHER INFORMATION: 0015-Fab

<400> SEQUENCE: 26

Gln Ser Met Gln Glu Ser Gly Pro Gly Leu Val Lys Pro Ser Gln Thr
 1               5                  10                  15

Leu Ser Leu Thr Cys Thr Val Ser Gly Phe Ser Leu Ser Ser Tyr Ala
             20                  25                  30

Met Ser Trp Ile Arg Gln His Pro Gly Lys Gly Leu Glu Trp Ile Gly
         35                  40                  45

Tyr Ile Trp Ser Gly Gly Ser Thr Asp Tyr Ala Ser Trp Ala Lys Ser
     50                  55                  60

Arg Val Thr Ile Ser Lys Thr Ser Thr Thr Val Ser Leu Lys Leu Ser
 65                  70                  75                  80

Ser Val Thr Ala Ala Asp Thr Ala Val Tyr Tyr Cys Ala Arg Arg Tyr
                 85                  90                  95

Gly Thr Ser Tyr Pro Asp Tyr Gly Asp Ala Ser Gly Phe Asp Pro Trp
            100                 105                 110

Gly Gln Gly Thr Leu Val Thr Val Ser Ser Ala Ser Val Ala Ala Pro
        115                 120                 125

Ser Val Phe Ile Phe Pro Pro Ser Asp Glu Gln Leu Lys Ser Gly Thr
130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly Glu Cys
225

<210> SEQ ID NO 27
<211> LENGTH: 118
<212> TYPE: PRT
<213> ORGANISM: Mus musculus

<400> SEQUENCE: 27

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Thr Met Asn Trp Val Arg Gln Ala Pro Gly Gln Gly Leu Glu Trp Met
         35                  40                  45

Gly Arg Ile Asn Pro His Asn Gly Gly Thr Asp Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Gly Tyr Tyr Tyr Ser Leu Asp Tyr Trp Gly Gln Gly Thr
            100                 105                 110
```

```
Leu Val Thr Val Ser Ser
            115

<210> SEQ ID NO 28
<211> LENGTH: 106
<212> TYPE: PRT
<213> ORGANISM: Mus musculus

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ile Arg Tyr Ile
            20                  25                  30

His Trp Tyr Gln Gln Lys Pro Gly Lys Ala Pro Lys Arg Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Arg Asn Ser Tyr Pro Trp Thr
                85                  90                  95

Phe Gly Gln Gly Thr Arg Leu Glu Ile Lys
            100                 105

<210> SEQ ID NO 29
<211> LENGTH: 122
<212> TYPE: PRT
<213> ORGANISM: Oryctolagus cuniculus

<400> SEQUENCE: 29

Gln Ser Met Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Tyr Ile Trp Ser Gly Gly Ser Thr Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Arg Tyr
                85                  90                  95

Gly Thr Ser Tyr Pro Asp Tyr Gly Asp Ala Asn Gly Phe Asp Pro Trp
            100                 105                 110

Gly Pro Gly Thr Leu Val Thr Val Ser Ser
        115                 120

<210> SEQ ID NO 30
<211> LENGTH: 110
<212> TYPE: PRT
<213> ORGANISM: Oryctolagus cuniculus

<400> SEQUENCE: 30

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30
```

```
Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Cys Tyr Ser Ser Ser Asn
                85                  90                  95

Val Asp Asn Thr Phe Gly Gly Gly Thr Glu Val Val Val Lys
                100                 105                 110

<210> SEQ ID NO 31
<211> LENGTH: 122
<212> TYPE: PRT
<213> ORGANISM: Artificial Sequence
<220> FEATURE:
<223> OTHER INFORMATION: 299-023 VH humanization variant_DASG

<400> SEQUENCE: 31

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30

Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Lys Thr Ser Thr Val Ser Leu Lys Leu Ser
65                  70                  75                  80

Ser Val Thr Ala Ala Asp Thr Ala Val Tyr Tyr Cys Ala Arg Arg Tyr
                85                  90                  95

Gly Thr Ser Tyr Pro Asp Tyr Gly Asp Ala Ser Gly Phe Asp Pro Trp
                100                 105                 110

Gly Gln Gly Thr Leu Val Thr Val Ser Ser
            115                 120

<210> SEQ ID NO 32
<211> LENGTH: 110
<212> TYPE: PRT
<213> ORGANISM: Artificial Sequence
<220> FEATURE:
<223> OTHER INFORMATION: 299-009 VL humanization variant_NYA

<400> SEQUENCE: 32

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95
```

Val Asp Asn Thr Phe Gly Gly Gly Thr Lys Val Glu Ile Lys
            100                 105                 110

<210> SEQ ID NO 33
<211> LENGTH: 7
<212> TYPE: PRT
<213> ORGANISM: Oryctolagus cuniculus

<400> SEQUENCE: 33

Gly Phe Ser Leu Ser Ser Tyr
1               5

<210> SEQ ID NO 34
<211> LENGTH: 5
<212> TYPE: PRT
<213> ORGANISM: Oryctolagus cuniculus

<400> SEQUENCE: 34

Trp Ser Gly Gly Ser
1               5

<210> SEQ ID NO 35
<211> LENGTH: 17
<212> TYPE: PRT
<213> ORGANISM: Oryctolagus cuniculus

<400> SEQUENCE: 35

Arg Tyr Gly Thr Ser Tyr Pro Asp Tyr Gly Asp Ala Asn Gly Phe Asp
1               5                   10                  15
Pro

<210> SEQ ID NO 36
<211> LENGTH: 17
<212> TYPE: PRT
<213> ORGANISM: Artificial Sequence
<220> FEATURE:
<223> OTHER INFORMATION: 299-000 HVR-H3 DASG

<400> SEQUENCE: 36

Arg Tyr Gly Thr Ser Tyr Pro Asp Tyr Gly Asp Ala Ser Gly Phe Asp
1               5                   10                  15
Pro

<210> SEQ ID NO 37
<211> LENGTH: 17
<212> TYPE: PRT
<213> ORGANISM: Artificial Sequence
<220> FEATURE:
<223> OTHER INFORMATION: 299-000 HVR-H3 DAQG

<400> SEQUENCE: 37

Arg Tyr Gly Thr Ser Tyr Pro Asp Tyr Gly Asp Ala Gln Gly Phe Asp
1               5                   10                  15
Pro

<210> SEQ ID NO 38
<211> LENGTH: 11
<212> TYPE: PRT
<213> ORGANISM: Artificial Sequence
<220> FEATURE:
<223> OTHER INFORMATION: 299-000 HVR-L1 RAA

```
<400> SEQUENCE: 38

Arg Ala Ser Gln Ser Ile Ser Ser Tyr Leu Ala
1               5                   10

<210> SEQ ID NO 39
<211> LENGTH: 7
<212> TYPE: PRT
<213> ORGANISM: Oryctolagus cuniculus

<400> SEQUENCE: 39

Arg Ala Ser Thr Leu Ala Ser
1               5

<210> SEQ ID NO 40
<211> LENGTH: 12
<212> TYPE: PRT
<213> ORGANISM: Artificial Sequence
<220> FEATURE:
<223> OTHER INFORMATION: 299-000 HVR-L3 NYA

<400> SEQUENCE: 40

Gln Gln Asn Tyr Ala Ser Ser Asn Val Asp Asn Thr
1               5                   10

<210> SEQ ID NO 41
<211> LENGTH: 119
<212> TYPE: PRT
<213> ORGANISM: Artificial Sequence
<220> FEATURE:
<223> OTHER INFORMATION: anti-CD20 antibody VH

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 42
<211> LENGTH: 112
<212> TYPE: PRT
<213> ORGANISM: Artificial Sequence
<220> FEATURE:
<223> OTHER INFORMATION: anti-CD20 antibody VL

<400> SEQUENCE: 42

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30
```

```
Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Val Glu Ile Lys
            100                 105                 110

<210> SEQ ID NO 43
<211> LENGTH: 116
<212> TYPE: PRT
<213> ORGANISM: Artificial Sequence
<220> FEATURE:
<223> OTHER INFORMATION: humanized anti-alpha synuclein acntibody 9E4 VH

<400> SEQUENCE: 43

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
     50                  55                  60

Lys Gly Arg Phe Thr Ile Ser Arg Asp Asp Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Ala Gly Ile Asp Tyr Trp Gly Gln Gly Thr Leu Val
            100                 105                 110

Thr Val Ser Ser
        115

<210> SEQ ID NO 44
<211> LENGTH: 113
<212> TYPE: PRT
<213> ORGANISM: Artificial Sequence
<220> FEATURE:
<223> OTHER INFORMATION: humanized anti-alpha synuclein acntibody 9E4 VL

<400> SEQUENCE: 44

Asp Ile Gln Met Thr Gln Ser Pro Ser Ser Leu Ser Ala Ser Val Gly
 1               5                  10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Leu Ala Thr Tyr Tyr Cys Gln Gln
                 85                  90                  95
```

-continued

```
Tyr Tyr Ser Tyr Pro Leu Thr Phe Gly Gly Gly Thr Lys Leu Glu Ile
            100                 105                 110
Lys

<210> SEQ ID NO 45
<211> LENGTH: 115
<212> TYPE: PRT
<213> ORGANISM: Mus musculus

<400> SEQUENCE: 45

Gln Val Gln Leu Gln Gln Ser Gly Ala Glu Leu Ala Lys Pro Gly Thr
1               5                   10                  15

Ser Val Gln Met Ser Cys Lys Ala Ser Gly Tyr Thr Phe Thr Asn Tyr
            20                  25                  30

Trp Met Asn Trp Ile Lys Ala Arg Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Lys Ala Ile Leu Thr Ala Asp Lys Ser Ser Asn Thr Ala Tyr
65                  70                  75                  80

Met His Leu Ser Ser Leu Thr Ser Glu Asp Ser Ala Val Tyr Phe Cys
                85                  90                  95

Ala Ser Gly Gly His Leu Ala Tyr Trp Gly Gln Gly Thr Val Val Thr
            100                 105                 110

Val Ser Ala
        115

<210> SEQ ID NO 46
<211> LENGTH: 112
<212> TYPE: PRT
<213> ORGANISM: Mus musculus

<400> SEQUENCE: 46

Asp Val Val Met Thr Gln Ile Pro Leu Tyr Leu Ser Val Ser Pro Gly
1               5                   10                  15

Asp Gln Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Lys Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Ile Arg
            100                 105                 110

<210> SEQ ID NO 47
<211> LENGTH: 115
<212> TYPE: PRT
<213> ORGANISM: Mus musculus

<400> SEQUENCE: 47

Val Gln Leu Gln Gln Ser Gly Pro Glu Leu Val Lys Pro Gly Thr Ser
1               5                   10                  15
```

```
Val Lys Ile Ser Cys Lys Ala Ser Gly Tyr Ser Phe Thr Ser Tyr Tyr
         20                  25                  30

Ile His Trp Val Lys Gln Ser Pro Gly Gln Gly Leu Glu Trp Ile Gly
         35                  40                  45

Trp Ile Tyr Pro Gly Ser Gly Asn Thr Lys Tyr Ser Glu Lys Phe Lys
 50                  55                  60

Gly Lys Ala Thr Leu Thr Ala Asp Thr Ser Ser Thr Ala Tyr Met
 65                  70                  75                  80

Gln Leu Ser Ser Leu Thr Ser Glu Asp Ser Ala Val Tyr Phe Cys Ala
                 85                  90                  95

Arg Asp Gly Cys Tyr Gly Phe Ala Tyr Trp Gly Gln Gly Thr Leu Val
                100                 105                 110

Thr Val Ser
        115

<210> SEQ ID NO 48
<211> LENGTH: 111
<212> TYPE: PRT
<213> ORGANISM: Mus musculus

<400> SEQUENCE: 48

Asp Ile Val Leu Thr Gln Ser Pro Ala Ser Leu Ala Val Ser Leu Gly
1               5                  10                  15

Gln Arg Ala Thr Ile Ser Cys Lys Ala Ser Gln Ser Val Asp Tyr Asp
         20                  25                  30

Gly Asp Ser Tyr Met Asn Trp Tyr Gln Gln Lys Pro Gly Gln Pro Pro
         35                  40                  45

Lys Phe Leu Ile Cys Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                 85                  90                  95

Glu Asp Pro Phe Thr Phe Gly Ser Gly Thr Lys Leu Glu Ile Lys
                100                 105                 110

<210> SEQ ID NO 49
<211> LENGTH: 115
<212> TYPE: PRT
<213> ORGANISM: Oryctolagus cuniculus

<400> SEQUENCE: 49

Gln Ser Val Glu Glu Ser Gly Gly Arg Leu Val Thr Pro Gly Thr Pro
1               5                  10                  15

Leu Thr Leu Thr Cys Thr Val Ser Gly Phe Ser Ile Asn Ser Tyr Ala
         20                  25                  30

Met Ile Trp Val Arg Gln Ala Pro Gly Glu Gly Leu Glu Trp Ile Gly
         35                  40                  45

Val Ile Tyr Pro Ser Gly Asn Thr Tyr Tyr Ala Asn Trp Ala Lys Gly
 50                  55                  60

Arg Phe Thr Val Ser Arg Thr Ser Thr Thr Val Asp Leu Lys Ile Thr
 65                  70                  75                  80

Ser Pro Thr Thr Glu Asp Thr Ala Thr Tyr Phe Cys Ala Arg Arg Asp
                 85                  90                  95

Gly Thr Asp Lys Thr Phe Asn Ile Trp Gly Pro Gly Thr Leu Val Thr
                100                 105                 110
```

Val Ser Leu
        115

<210> SEQ ID NO 50
<211> LENGTH: 112
<212> TYPE: PRT
<213> ORGANISM: Oryctolagus cuniculus

<400> SEQUENCE: 50

Gln Val Leu Thr Gln Thr Pro Ser Pro Val Ser Ala Ala Val Gly Gly
1               5                   10                  15

Thr Val Thr Ile Asn Cys Gln Ala Ser Gln Asn Val Tyr Gly Asp Asn
            20                  25                  30

Tyr Leu Ala Trp Tyr Gln Gln Lys Pro Gly Gln Pro Pro Lys Leu Leu
        35                  40                  45

Ile Tyr Glu Ala Ser Lys Leu Ala Ser Gly Val Pro Pro Arg Phe Ser
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Gln Gly Glu Phe Leu Cys Thr
                85                  90                  95

Thr Ser Asp Cys Phe Thr Phe Gly Gly Gly Thr Gly Val Val Val Arg
            100                 105                 110

<210> SEQ ID NO 51
<211> LENGTH: 119
<212> TYPE: PRT
<213> ORGANISM: Oryctolagus cuniculus

<400> SEQUENCE: 51

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Tyr Ala
            20                  25                  30

Met Ser Trp Val Arg Gln Ala Pro Gly Lys Gly Leu Glu Trp Ile Gly
        35                  40                  45

Val Ile Asn Ser Ser Gly Ala Thr Tyr Tyr Ala Ser Trp Ala Lys Gly
    50                  55                  60

Arg Phe Thr Ile Ser Glu Thr Ser Thr Thr Val Glu Leu Lys Ile Thr
65                  70                  75                  80

Ser Pro Thr Thr Glu Asp Thr Ala Thr Tyr Phe Cys Ala Arg Trp Thr
                85                  90                  95

Tyr Asp Asp Tyr Gly Asp Phe Gln Gly Phe Asn Ile Trp Gly Pro Gly
            100                 105                 110

Thr Leu Val Thr Val Ser Leu
        115

<210> SEQ ID NO 52
<211> LENGTH: 111
<212> TYPE: PRT
<213> ORGANISM: Oryctolagus cuniculus

<400> SEQUENCE: 52

Ala Val Leu Thr Gln Thr Pro Ser Pro Val Ser Ala Ala Val Gly Gly
1               5                   10                  15

Thr Val Thr Ile Ser Cys Gln Ser Ser Gln Ser Val Tyr Asn Asn Asn
            20                  25                  30

-continued

Asp Leu Ala Trp Tyr Gln Gln Lys Pro Gly Gln Pro Pro Lys Leu Leu
              35                  40                  45

Ile Tyr Arg Ala Ser Lys Leu Ala Ser Gly Val Pro Ser Arg Phe Lys
 50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Leu Gly Gly Tyr Asp Asp Asp
              85                  90                  95

Ala Asp Met Gly Ala Phe Gly Gly Gly Thr Glu Val Val Val Lys
              100                 105                 110

<210> SEQ ID NO 53
<211> LENGTH: 111
<212> TYPE: PRT
<213> ORGANISM: Artificial Sequence
<220> FEATURE:
<223> OTHER INFORMATION: heavy chain variable domain

<400> SEQUENCE: 53

Gln Ser Leu Glu Glu Ser Gly Gly Arg Leu Val Thr Pro Gly Thr Pro
 1               5                  10                  15

Leu Thr Leu Thr Cys Thr Val Ser Gly Ile Asp Leu Ser Arg Asp Thr
              20                  25                  30

Met Ile Trp Val Arg Gln Ala Pro Gly Glu Gly Leu Glu Trp Ile Gly
              35                  40                  45

Ser Ile Tyr Thr Asp Ser Gly Asn Thr Trp Tyr Ala Ser Trp Val Lys
 50                  55                  60

Gly Arg Phe Thr Ile Ser Lys Thr Ser Thr Thr Val Asp Leu Arg
 65                  70                  75                  80

Ile Thr Ser Pro Thr Thr Glu Asp Thr Ala Thr Tyr Phe Cys Ala Arg
              85                  90                  95

Asn Phe Ser Val Trp Gly Pro Gly Thr Leu Val Thr Val Ser Leu
              100                 105                 110

<210> SEQ ID NO 54
<211> LENGTH: 112
<212> TYPE: PRT
<213> ORGANISM: Artificial Sequence
<220> FEATURE:
<223> OTHER INFORMATION: light chain variable domain

<400> SEQUENCE: 54

Gln Val Leu Thr Gln Thr Pro Ser Pro Val Ser Ala Ala Val Gly Gly
 1               5                  10                  15

Thr Val Thr Ile Asn Cys Gln Ala Ser Gln Ser Val Tyr Asn Ser Asp
              20                  25                  30

Arg Leu Ala Trp Phe Gln Gln Met Arg Gly Gln Pro Pro Lys Leu Leu
              35                  40                  45

Ile Tyr Asp Val Ser Lys Leu Ala Ser Gly Val Pro Ser Arg Phe Ser
 50                  55                  60

Gly Ser Gly Ser Gly Thr Gln Phe Thr Leu Thr Ile Ser Asp Val Gln
 65                  70                  75                  80

Cys Asp Asp Ala Ala Thr Tyr Tyr Cys Leu Gly Gly Tyr Asp Cys Ser
              85                  90                  95

Ser Ala Glu Cys Asn Val Phe Gly Gly Gly Thr Glu Val Val Val Lys
              100                 105                 110

<210> SEQ ID NO 55

```
<211> LENGTH: 536
<212> TYPE: PRT
<213> ORGANISM: Homo sapiens

<400> SEQUENCE: 55

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
                20                  25                  30

Ala Val Ser Trp Ala Ser Gly Ala Arg Pro Cys Ile Pro Lys Ser Phe
            35                  40                  45

Gly Tyr Ser Ser Val Val Cys Val Cys Asn Ala Thr Tyr Cys Asp Ser
50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
                100                 105                 110

Lys Phe Gln Lys Val Lys Gly Phe Gly Gly Ala Met Thr Asp Ala Ala
            115                 120                 125

Ala Leu Asn Ile Leu Ala Leu Ser Pro Pro Ala Gln Asn Leu Leu Leu
130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
                180                 185                 190

Thr Lys Leu Lys Ile Pro Leu Ile His Arg Ala Leu Gln Leu Ala Gln
            195                 200                 205

Arg Pro Val Ser Leu Leu Ala Ser Pro Trp Thr Ser Pro Thr Trp Leu
210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
                260                 265                 270

Asn Glu Pro Ser Ala Gly Leu Leu Ser Gly Tyr Pro Phe Gln Cys Leu
            275                 280                 285

Gly Phe Thr Pro Glu His Gln Arg Asp Phe Ile Ala Arg Asp Leu Gly
290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
                340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
370                 375                 380
```

```
Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
            405                 410                 415

Trp Thr Asp Trp Asn Leu Ala Leu Asn Pro Glu Gly Gly Pro Asn Trp
        420                 425                 430

Val Arg Asn Phe Val Asp Ser Pro Ile Ile Val Asp Ile Thr Lys Asp
    435                 440                 445

Thr Phe Tyr Lys Gln Pro Met Phe Tyr His Leu Gly His Phe Ser Lys
450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
                500                 505                 510

Asp Pro Ala Val Gly Phe Leu Glu Thr Ile Ser Pro Gly Tyr Ser Ile
            515                 520                 525

His Thr Tyr Leu Trp Arg Arg Gln
        530                 535

<210> SEQ ID NO 56
<211> LENGTH: 20
<212> TYPE: PRT
<213> ORGANISM: Artificial Sequence
<220> FEATURE:
<223> OTHER INFORMATION: peptidic linker

<400> SEQUENCE: 56

Gly Gly Gly Gly Ser Gly Gly Gly Gly Ser Gly Gly Gly Gly Ser Gly
1               5                   10                  15

Gly Gly Gly Ser
            20

<210> SEQ ID NO 57
<211> LENGTH: 32
<212> TYPE: PRT
<213> ORGANISM: Artificial Sequence
<220> FEATURE:
<223> OTHER INFORMATION: peptidic linker

<400> SEQUENCE: 57

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

<210> SEQ ID NO 58
<211> LENGTH: 140
<212> TYPE: PRT
<213> ORGANISM: Homo sapiens

<400> SEQUENCE: 58

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45
```

```
Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
    130                 135                 140

<210> SEQ ID NO 59
<211> LENGTH: 441
<212> TYPE: PRT
<213> ORGANISM: Homo sapiens

<400> SEQUENCE: 59

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
    195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270
```

```
Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
                435                 440

<210> SEQ ID NO 60
<211> LENGTH: 441
<212> TYPE: PRT
<213> ORGANISM: Homo sapiens
<220> FEATURE:
<221> NAME/KEY: MISC_FEATURE
<222> LOCATION: (422)..(422)
<223> OTHER INFORMATION: X=phosphoserine

<400> SEQUENCE: 60

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175
```

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Xaa Pro Gln Leu Ala Thr Leu Ala Asp Glu Val
            420                 425                 430

Ser Ala Ser Leu Ala Lys Gln Gly Leu
        435                 440

<210> SEQ ID NO 61
<211> LENGTH: 297
<212> TYPE: PRT
<213> ORGANISM: Homo sapiens

<400> SEQUENCE: 61

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
            115                 120                 125

Ser Gly Met Ile Leu Ser Ile Met Asp Ile Leu Asn Ile Lys Ile Ser
        130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Pro Ile Gln Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 62
<211> LENGTH: 5
<212> TYPE: PRT
<213> ORGANISM: Oryctolagus cuniculus

<400> SEQUENCE: 62

Ser Tyr Ala Met Ser
1               5

<210> SEQ ID NO 63
<211> LENGTH: 16
<212> TYPE: PRT
<213> ORGANISM: Oryctolagus cuniculus

<400> SEQUENCE: 63

Tyr Ile Trp Ser Gly Gly Ser Thr Asp Tyr Ala Ser Trp Ala Lys Gly
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: 299-000 HVR-H2 Kabat G65S

<400> SEQUENCE: 64

Tyr Ile Trp Ser Gly Gly Ser Thr Asp Tyr Ala Ser Trp Ala Lys Ser
1               5                   10                  15

<210> SEQ ID NO 65
<211> LENGTH: 11
<212> TYPE: PRT
<213> ORGANISM: Oryctolagus cuniculus

<400> SEQUENCE: 65

Gln Ala Ser Gln Ser Ile Ser Ser Tyr Leu Ser
1               5                   10

<210> SEQ ID NO 66
<211> LENGTH: 12
<212> TYPE: PRT
<213> ORGANISM: Oryctolagus cuniculus

<400> SEQUENCE: 66

Gln Gln Cys Tyr Ser Ser Ser Asn Val Asp Asn Thr
1               5                   10

<210> SEQ ID NO 67
<211> LENGTH: 115
<212> TYPE: PRT
<213> ORGANISM: Artificial Sequence
<220> FEATURE:
<223> OTHER INFORMATION: DP47GS VH

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser
        115

<210> SEQ ID NO 68
<211> LENGTH: 108
<212> TYPE: PRT
<213> ORGANISM: Artificial Sequence
<220> FEATURE:
<223> OTHER INFORMATION: DP47GS VL

<400> SEQUENCE: 68

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

```
Leu Thr Phe Gly Gln Gly Thr Lys Val Glu Ile Lys
            100                 105

<210> SEQ ID NO 69
<211> LENGTH: 442
<212> TYPE: PRT
<213> ORGANISM: Artificial Sequence
<220> FEATURE:
<223> OTHER INFORMATION: DP47GS HC (Fc wt, P329G LALA)

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

```
Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser
        435                 440

<210> SEQ ID NO 70
<211> LENGTH: 215
<212> TYPE: PRT
<213> ORGANISM: Artificial Sequence
<220> FEATURE:
<223> OTHER INFORMATION: DP47GS LC

<400> SEQUENCE: 70

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

METHOD FOR DETERMINING THE AMOUNT OF A THERAPEUTIC ANTIBODY IN THE BRAIN

CROSS-REFERENCE TO RELATED APPLICATIONS

This application is claiming priority to European Patent Application No. EP20150135.0, filed Jan. 2, 2020, all of which are incorporated by reference in its entirety.

SEQUENCE LISTING

This application contains a Sequence Listing which has been submitted electronically in ASCII format and is hereby incorporated by reference in its entirety. Said ASCII copy, created on Dec. 17, 2020, is named P35855-US_Sequence_Listing and is 120,257 bytes in size.

FIELD OF THE INVENTION

The current invention is in the field of immunoassays. More specifically, herein is reported a method for the determination of the amount of a therapeutic antibody in brain tissue, more specifically of the amount of a therapeutic antibody transported across the blood-brain-barrier from the blood into the brain.

BACKGROUND

For the analysis of therapeutic monoclonal antibodies (tmAbs) in samples of in-vitro or in-vivo origin a respective assay is necessary.

Determining the amount of a therapeutic antibody is generally carried out by determining the amount of said therapeutic antibody in a sample. Therefore, e.g., an immunoassay, such as, ELISA, RIA, protein blot (Western blot) assay, and the like can be used.

The role of antibodies and their receptors in protection against ordered protein assembly in neurodegeneration was reviewed by Katsinelos et al. (Front. Immunol. 10 (2019) A1139). They have outlined that IgG levels are maintained in human serum at around 10 mg/ml. The brain is isolated from serum by the blood-brain barrier (BBB), which is impermeable to large macromolecules including IgG and is bathed in cerebrospinal fluid (CSF), which is produced following the filtration of blood and transport of ions across the choroid plexus. Thus, the resulting concentration of IgG in CSF is around 500- to 1,000-fold lower than in serum. Hanzatian et al. (mAbs 10 (2018) 765-777) reported that therapeutic monoclonal antibodies and endogenous IgG antibodies show limited uptake into the central nervous system (CNS) due to the blood-brain barrier (BBB), which regulates and controls the selective and specific transport of both exogenous and endogenous materials to the brain. The use of natural transport mechanisms, such as receptor-mediated transcytosis (RMT), to deliver antibody therapeutics into the brain have been studied in rodents and monkeys. After systemic administration of each DVD-Ig, Hanzatian et al. used two independent methods in parallel to observe specific uptake into the brain: An electrochemiluminescent-based sensitive quantitative assay and a semi-quantitative immunohistochemistry technique were used for brain concentration determination and bio distribution/localization in brain, respectively. Significantly enhanced brain uptake and retention was observed for all TfR1 DVD-Ig proteins regardless of the CNS target or the systemic administration route selected. To prepare brain samples for analysis the used C57BL/6N mice were transcardially perfused with cold Dulbecco's phosphate-buffered saline (PBS) containing heparin at a rate of 2 ml/min for 10 min via programmable peristaltic pump.

A comparable approach had been used by Zuchero et al. (Neuron 89 (2016) 70-82; wild-type mice, which were IV injected with the target antibody followed by collection of the whole blood and PBS perfusion) and Janowicz et al. (Nature Sci. Rep. 9 (2019) 9255; P301L tau transgenic pR5 mice, to which Alexa-647-labeled IgG, Fab or scFv had been administered by retro-orbital injection, were perfused following treatment to remove the antibody from their vasculature).

In WO 2018/152359, mice overexpressing human Tau from PS 19 line were used to evaluate target engagement of chimeric IgG anti-tau antibody clones 1C7 and TAT. Therefore, mice were injected i.v. (at 35 mg/kg) or i.p. (at 50 mg/kg) with a control IgG, chimeric IgG clone 1C7, or chimeric IgG clone TAT. At 2 or 7 days post-injection, cerebral spinal fluid (CSF) was collected via the cisterna magna and visually inspected for potential blood contamination and following transcardial perfusion with ice-cold PBS, brain tissue was removed and snap frozen.

Ayabe, M., et al. reported that an anti-human interleukin-6 receptor (hIL-6R) antibody or control antibody were administered intravenously to tumor-bearing hIL-6R transgenic mice and bovine serum albumin (BSA) was administered intravenously as a marker for residual blood volume in tissues. The lysate samples were treated with immune precipitation using anti-BSA antibody and Protein A magnetic beads followed by tryptic digestion. Each surrogate peptide was analyzed simultaneously by LC/ESI-MS/MS. Corrected tissue concentration was calculated.

Vedeler, et al., reported about immunoglobulins in serum and cerebrospinal fluid from patients with acute Guillain-Barre syndrome (Acta Neurol. Scand. 73 (1986) 388-393.

Shah, et al., reported antibody bio distribution coefficients, especially inferring tissue concentrations of monoclonal antibodies based on the plasma concentrations in several preclinical species and human (MABS, 5 (2013) 297-305).

Lavezzi, et al., reported MPBPK-TMDD models for mAbs, especially alternative models, comparison, and identifiability issues (J. Pharmacokin. Pharmcodyn. 45 (2018) 787-802).

SUMMARY OF THE INVENTION

Herein is reported a method for the determination of the amount of a therapeutic antibody, which has been transported across the blood-brain-barrier from the blood into the brain of an experimental animal. The amount is preferably determined in a brain lysate sample. The gist of the invention lies in the additional application of an inert antibody, which is not transported across the blood-brain-barrier, shortly before obtaining the brain sample in which the amount of the therapeutic antibody transported across the blood-brain-barrier has to be determined. By applying the inert antibody, a correction value for therapeutic antibody present in residual blood in the brain sample is obtained. This residual blood-derived amount is used to correct the determined amount for non-brain-located antibody. A determination without correction would determine the total amount of therapeutic antibody in the sample, i.e. the amount transported across the blood-brain-barrier into the brain and the amount in residual blood in the sample. The amount of therapeutic antibody in residual blood is not neglectable, as only about 0.1% of the antibody in the blood will pass the blood-brain-barrier. Thus, the concentration of the therapeutic antibody in the blood exceeds the concentration of the therapeutic antibody in the brain by at least two and up to three orders of magnitude. Thereby the results obtained are too high if not corrected with a method according to the current invention.

The current invention is based, at least in part, on the finding that for a robust and correct determination of the amount in brain lysates of a therapeutic antibody transported across the blood-brain-barrier into the brain a correction, i.e. reduction, with the amount of therapeutic antibody in residual blood in the brain lysate sample has to be made.

The current invention is based, at least in part, on the finding that the amount of residual blood in a brain lysate can be determined by applying a correction antibody shortly before the brain sample is taken. It has been found that it is especially advantageous to use as reference antibody an antibody that is not specifically binding to any target in the experimental animal from which the brain sample is obtained, most preferably a human germline antibody.

One aspect of the invention is a method/assay for determining the concentration of a therapeutic antibody in a tissue of an experimental animal, whereby the tissue has a barrier to the blood circulation of said animal and whereby the therapeutic antibody had been administered to said experimental animal, wherein the interference from residual blood in a tissue sample of the experimental animal, which is used for determining the concentration of the therapeutic antibody in said tissue, is reduced, the method comprising the following steps
  i) determining the concentration of the therapeutic antibody in a blood sample of the experimental animal,
  ii) determining the concentration of the therapeutic antibody in the tissue sample of the experimental animal,
  iii) determining the concentration of an inert reference antibody in the blood sample of the experimental animal,
  iv) determining the concentration of the inert reference antibody in the tissue sample of the experimental animal,
  v) determining the tissue concentration in the tissue sample,
and determining the concentration of the therapeutic antibody in the tissue of the experimental animal with the following formula:

$$C_{tmAb,tissue} = \frac{C_{tmAb,tissue,det.}}{C_{tissue,sample}} - \frac{\frac{C_{refmAb,tissue,det.}}{C_{tissue,sample}}}{C_{refmAb,plasma,det.}} * C_{tmAb,plasma,det.}$$

with
  $C_{tmAb,plasma,det}$=concentration of the therapeutic antibody of i)
  $C_{tmAb,tissue,det.}$=concentration of the therapeutic antibody of ii)
  $C_{refmAb,tissue,det.}$=concentration of the inert reference antibody of iii)
  $C_{refmAb,plasma,det.}$=concentration of the inert reference antibody of iv)
  $C_{tissue,sample}$=tissue concentration of v)
whereby the inert reference antibody does not cross said barrier between the tissue and the blood circulation,
whereby the inert reference antibody had been administered i) either together with the therapeutic antibody in case the sample is to be taken within 5 minutes after the administration of the therapeutic antibody, or ii) 2 to 10 minutes prior to taking the tissue sample.

The same aspect in an alternative wording is, a method for determining the concentration of a therapeutic antibody in a tissue of an experimental animal to whom the therapeutic antibody had been administered, wherein the interference from residual blood in a tissue sample of the experimental animal, which is used for determining the concentration of the therapeutic antibody in said tissue, is reduced,
  wherein the concentration of the therapeutic antibody in the tissue of the experimental animal is calculated with the following formula:

$$C_{tmAb,tissue} = \frac{C_{tmAb,tissue,det.}}{C_{tissue,sample}} - \frac{\frac{C_{refmAb,tissue,det.}}{C_{tissue,sample}}}{C_{refmAb,plasma,det.}} * C_{tmAb,plasma,det.}$$

wherein
  $C_{tmAb,tissue,det.}$=obtained by determining the concentration of the therapeutic antibody in the tissue sample of the experimental animal,
  $C_{tmAb,plasma,det.}$=obtained by determining the concentration of the therapeutic antibody in a blood sample of the experimental animal,
  $C_{refmAb,tissue,det.}$=obtained by determining the concentration of the inert reference antibody in the tissue sample of the experimental animal,
  $C_{refmAb,plasma,det.}$=obtained by determining the concentration of an inert reference antibody in the blood sample of the experimental animal,
  $C_{tissue,sample}$=obtained by determining the tissue concentration in the tissue sample,
  whereby the inert reference antibody does not penetrate into said tissue,
  whereby the inert reference antibody is administered 2 to 10 minutes prior to obtaining the tissue sample.

The following are all individual embodiment of each and any aspects of the invention. Thus, all and any possible permutation of embodiments is disclosed with respect to any individual aspect according to the invention, In one embodiment, the blood sample is taken at most 5 minutes prior to the tissue sample. In one embodiment, the blood sample is taken prior to the tissue sample. In one embodiment, the blood sample is taken together or at the same time as the tissue sample.

In one embodiment, the tissue is either brain tissue and the therapeutic antibody can cross the blood-brain-barrier or ocular tissue and the therapeutic antibody can cross the blood-ocular-barrier.

One aspect of the invention is a method/assay for determining the concentration of a therapeutic antibody in brain tissue or a brain tissue sample of an experimental animal, whereby the brain tissue has a barrier to the blood circulation of said animal and whereby the therapeutic antibody had been administered to said experimental animal, wherein the interference from residual blood in a brain tissue sample of the experimental animal, which is used for determining the concentration of the therapeutic antibody in said brain tissue, is reduced, the method comprising the following steps
  i) determining the concentration of the therapeutic antibody in a blood sample of the experimental animal, ii) determining the concentration of the therapeutic antibody in the brain tissue sample of the experimental animal,
iii) determining the concentration of an inert reference antibody in the blood sample of the experimental animal,
iv) determining the concentration of the inert reference antibody in the brain tissue sample of the experimental animal,
v) determining the brain tissue concentration in the tissue sample,
and determining the concentration of the therapeutic antibody in the brain tissue or the brain tissue sample of the experimental animal with the following formula:

$$C_{tmAb,tissue} = \frac{C_{tmAb,tissue,det.}}{C_{tissue,sample}} - \frac{\frac{C_{refmAb,tissue,det.}}{C_{tissue,sample}}}{C_{refmAb,plasma,det.}} * C_{tmAb,plasma,det.}$$

with $C_{tmAb,plasma,det.}$=concentration of the therapeutic antibody of i)

$C_{tmAb,tissue,det.}$=concentration of the therapeutic antibody of ii)

$C_{refmAb,tissue,det.}$=concentration of the inert reference antibody of iii)

$C_{refmAb,plasma,det.}$=concentration of the inert reference antibody of iv)

$C_{tissue,sample}$=tissue concentration of v)

whereby the inert reference antibody does not cross said blood-brain-barrier between the brain tissue and the blood circulation,
whereby the inert reference antibody had been administered i) either together with the therapeutic antibody in case the brain tissue sample is to be taken within 5 minutes after the administration of the therapeutic antibody, or ii) 2 to 10 minutes prior to taking the brain tissue sample.

The same aspect in an alternative wording is, a method for determining the concentration of a therapeutic antibody in brain tissue or a brain tissue sample of an experimental animal to whom the therapeutic antibody had been administered, wherein the interference from residual blood in the brain tissue sample of the experimental animal, which is used for determining the concentration of the therapeutic antibody in said brain tissue, is reduced, wherein the concentration of the therapeutic antibody in the brain tissue of the experimental animal is calculated with the following formula:

$$C_{tmAb,tissue} = \frac{C_{tmAb,tissue,det.}}{C_{tissue,sample}} - \frac{\frac{C_{refmAb,tissue,det.}}{C_{tissue,sample}}}{C_{refmAb,plasma,det.}} * C_{tmAb,plasma,det.}$$

wherein $C_{tmAb,tissue,det.}$=obtained by determining the concentration of the therapeutic antibody in the brain tissue sample of the experimental animal, $C_{tmAb,plasma,det.}$=obtained by determining the concentration of the therapeutic antibody in a blood sample of the experimental animal, $C_{refmAb,tissue,det.}$=obtained by determining the concentration of the inert reference antibody in the brain tissue sample of the experimental animal, $C_{refmAb,plasma,det.}$=obtained by determining the concentration of an inert reference antibody in the blood sample of the experimental animal, $C_{tissue,sample}$=obtained by determining the brain tissue concentration in the brain tissue sample, whereby the inert reference antibody does not penetrate into said brain tissue, whereby the inert reference antibody is administered 2 to 10 minutes prior to obtaining the brain tissue sample.

In one embodiment, the therapeutic antibody is a bispecific antibody.

In one embodiment, the therapeutic antibody is specifically binding to human transferrin receptor and a brain target.

In one embodiment, the brain target is human CD20 or human Abeta or human alpha-synuclein or human tau or human glucocerebrosidase or human lingo-1 or human huntingtin.

In one embodiment, the experimental animal is selected from mouse, rat, rabbit, dog, sheep, ape, and monkey.

In one embodiment, the experimental animal is a non-human experimental animal with a body weight of more than 100 g and less than 15 kg.

In one embodiment, the experimental animal is a cynomolgus monkey.

In one embodiment, the inert reference antibody is a human germline antibody.

In one embodiment, the inert reference antibody is DP47GS. In one embodiment, the inert reference antibody comprises a heavy chain variable domain of SEQ ID NO: 67 and a light chain variable domain of SEQ ID NO: 68. In one embodiment, the inert reference antibody comprises a heavy chain of SEQ ID NO: 69 and a light chain of SEQ ID NO: 70.

In one embodiment, the inert reference antibody does not cross said barrier in detectable amounts within 15 minutes after its application.

In one embodiment, the inert reference antibody does not cross said barrier in detectable amounts within 10 minutes after its application.

In one embodiment, the inert antibody is administered 5 to 10 minutes prior to taking the tissue sample.

In one embodiment, the tissue is perfused with an aqueous solution directly after taking the blood sample and prior to taking the tissue sample.

In one embodiment, the determining of the concentrations is by a bridging ELISA.

DETAILED DESCRIPTION OF EMBODIMENTS OF THE INVENTION

Herein is reported a method for the determination of the amount of a therapeutic antibody, which has been transported across the blood-brain-barrier from the blood into the brain of an experimental animal. The amount is preferably determined in a brain lysate sample. The gist of the invention lies in the additional application of an inert antibody, which is not transported across the blood-brain-barrier, shortly before obtaining the brain sample in which the amount of the therapeutic antibody transported across the blood-brain-barrier has to be determined. By applying the inert antibody, a correction value for therapeutic antibody present in residual blood in the brain sample is obtained. This residual blood-derived amount is used to correct the determined amount for non-brain-located antibody. A determination without correction would determine the total amount of therapeutic antibody in the sample, i.e. the amount transported across the blood-brain-barrier into the brain and the amount in residual blood in the sample. The amount of therapeutic antibody in residual blood is not neglectable, as only about 0.1% of the antibody in the blood will pass the blood-brain-barrier. Thus, the concentration of the therapeutic antibody in the blood exceeds the concentration of the therapeutic antibody in the brain by at least two and up to three orders of magnitude. Thereby the results obtained are too high if not corrected with a method according to the current invention.

The current invention is based, at least in part, on the finding that for a robust and correct determination of the amount in brain lysates of a therapeutic antibody transported across the blood-brain-barrier into the brain a correction, i.e. reduction, with the amount of therapeutic antibody in residual blood in the brain lysate sample has to be made.

The current invention is based, at least in part, on the finding that the amount of residual blood in a brain lysate can be determined by applying a correction antibody shortly before the brain sample is taken. It has been found that it is especially advantageous to use as reference antibody an antibody that is not specifically binding to any target in the experimental animal from which the brain sample is obtained, most preferably a human germline antibody.

One aspect of the invention is a method/assay for determining the concentration of a therapeutic antibody in a tissue of an experimental animal, whereby the tissue has a barrier to the blood circulation of said animal and whereby the therapeutic antibody had been administered to said experimental animal, wherein the interference from residual blood in a tissue sample of the experimental animal, which is used for determining the concentration of the therapeutic antibody in said tissue, is reduced, the method comprising the following steps
  i) determining the concentration of the therapeutic antibody in a blood serum sample of the experimental animal,
  ii) determining the concentration of the therapeutic antibody in the tissue sample of the experimental animal,
  iii) determining the concentration of an inert reference antibody in the blood serum sample of the experimental animal,
  iv) determining the concentration of the inert reference antibody in the tissue sample of the experimental animal,
  v) determining the tissue concentration in the tissue sample, and determining the concentration of the therapeutic antibody in the tissue of the experimental animal with the following formula:

$$C_{tmAb,tissue} = \frac{C_{tmAb,tissue,det.}}{C_{tissue,sample}} - \frac{\frac{C_{refmAb,tissue,det.}}{C_{tissue,sample}}}{C_{refmAb,plasma,det.}} * C_{tmAb,plasma,det.}$$

with
  $C_{tmAb,plasma,det.}$=concentration of the therapeutic antibody of i)
  $C_{tmAb,tissue,det.}$=concentration of the therapeutic antibody of ii)
  $C_{refmAb,tissue,det.}$=concentration of the inert reference antibody of iii)
  $C_{refmAb,plasma,det.}$=concentration of the inert reference antibody of iv)
  $C_{tissue,sample}$=tissue concentration of v)

whereby the inert reference antibody does not cross said barrier between the tissue and the blood circulation,
whereby the inert reference antibody had been administered i) either together with the therapeutic antibody in case the sample is to be taken within 5 minutes after the administration of the therapeutic antibody, or ii) 2 to 10 minutes prior to taking the tissue sample,
whereby the blood sample is taken together/directly prior/at the same time as the tissue sample.

Definitions

The knobs into holes dimerization modules and their use in antibody engineering are described in Carter P.; Ridgway J. B. B.; Presta L. G.: Immunotechnology, Volume 2, Number 1, February 1996, pp. 73-73(1).

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

The term "about" denotes a range of +/−20% of the thereafter following numerical value. In one embodiment, the term about denotes a range of +/−10% of the thereafter-following numerical value. In one embodiment, the term about denotes a range of +/−5% of the thereafter-following numerical value.

The term "antibody-dependent cellular cytotoxicity (ADCC)" is a function mediated by Fc receptor binding and refers to lysis of target cells by an antibody as reported herein in the presence of effector cells. ADCC is measured in one embodiment by the treatment of a preparation of CD19 expressing erythroid cells (e.g. K562 cells expressing recombinant human CD19) with an antibody as reported herein in the presence of effector cells such as freshly isolated PBMC (peripheral blood mononuclear cells) or purified effector cells from buffy coats, like monocytes or NK (natural killer) cells. Target cells are labeled with 51Cr and subsequently incubated with the antibody. The labeled cells are incubated with effector cells and the supernatant is analyzed for released 51Cr. Controls include the incubation of the target endothelial cells with effector cells but without the antibody. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In one preferred embodiment, binding to FcγR on NK cells is measured.

The term "amplifier" denotes an entity or process that enhances the signal in a detection method, such as an ELISA (e.g., an enzymatic amplifier used in an ELISA).

The terms "anti-human A-beta antibody" and "an antibody specifically binding to human A-beta" refer to an antibody that is capable of binding the human A-beta peptide with sufficient affinity such that the antibody is useful as a diagnostic and/or therapeutic agent in targeting A-beta peptide.

It is of note that human A-beta has several naturally occurring forms, whereby the human forms are referred to as Aβ39, Aβ40, Aβ41, Aβ42 and Aβ43. The most prominent form, Aβ42, has the amino acid sequence of SEQ ID NO: 01. In Aβ41, Aβ40, Aβ39, the C-terminal amino acids A, IA and VIA are missing, respectively.

In the Aβ43 form, an additional threonine residue is comprised at the C-terminus of SEQ ID NO: 01 (33106).

Thus, the term also encompasses antibodies that bind to a shortened fragment of the human A-beta polypeptide.

The term "antibody" herein is used in the broadest sense and encompasses various antibody structures, including but not limited to monoclonal antibodies, polyclonal antibodies, or multispecific antibodies (e.g., bispecific antibodies).

An antibody in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The constant domains of an antibody heavy chain comprise the CH1-domain, the CH2-domain and the CH3-domain, whereas the light chain comprises only one constant domain, CL, which can be of the kappa isotype or the lambda isotype.

The variable domain of an immunoglobulin's light or heavy chain in turn comprises different segments, i.e. four framework regions (FR) and three hypervariable regions (HVR).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, Nature Biotechnology 23:1126-1136 (2005).

The "blood-brain-barrier" or "BBB" refers to the physiological barrier between the peripheral circulation and the brain and spinal cord, which is formed by tight junctions within the brain capillary endothelial plasma membranes, creating a tight barrier that, restricts the transport of molecules into the brain, even very small molecules such as urea (60 Daltons). The BBB within the brain, the blood-spinal-cord barrier within the spinal cord, and the blood-retinal-barrier within the retina are contiguous capillary barriers within the CNS, and are herein collectively referred to an the blood-brain-barrier or BBB. The BBB also encompasses the blood-CSF barrier (choroid plexus) where the barrier is comprised of ependymal cells rather than capillary endothelial cells.

A "blood-brain-barrier receptor" (abbreviated "BBBR" herein) is an extracellular membrane-linked receptor protein expressed on brain endothelial cells which is capable of transporting molecules across the BBB or be used to transport exogenous administrated molecules. Examples of BBBR herein include: transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), and heparin-binding epidermal growth factor-like growth factor (HB-EGF). One preferred BBBR is transferrin receptor (TfR).

The term "brain effector entity" denotes a molecule that is to be transported to the brain across the BBB. The effector entity typically has a characteristic therapeutic activity that is desired to be delivered to the brain. Effector entities include neurologically disorder drugs and cytotoxic agents such as e.g. polypeptides and antibodies, in particular monoclonal antibodies or fragments thereof directed to a brain target.

The term "capture antibody" denotes an antibody that is used in a sandwich ELISA format to bind (i.e., capture) a target substance present in a sample for detection. A second antibody (i.e., the detection antibody) then binds to the captured target and allows detection of the antibody-target-antibody-complex (forming a "sandwich" comprised of antibody-target-antibody).

The "central nervous system" or "CNS" refers to the complex of nerve tissues that control bodily function, and includes the brain and spinal cord.

The terms "CNS antigen" and "brain target" denote an antigen and/or molecule expressed in the CNS, including the brain, which can be targeted with an antibody or small molecule. Examples of such antigen and/or molecule include, without limitation: beta-secretase 1 (BACE1), amyloid beta (Abeta), epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), glucocerebrosidase and caspase 6.

A "conjugate" is fusion protein of the present invention conjugated to one or more heterologous molecule(s), including but not limited to a label, neurological disorder drug or cytotoxic agent.

The term "detection antibody" denotes an antibody, which carries a means for visualization or quantitation. Such a means is typically an enzyme (catalyzing a colored or fluorescent reaction product following the addition of a suitable substrate), such as, e.g., horseradish peroxidase, urease, alkaline phosphatase, glucoamylase and β-galactosidase. In some embodiments, the detection antibody is directed against the antigen of interest. In some embodiments, the detection antibody is an anti-species antibody. In some embodiments, the detection antibody is conjugated to a detectable label such as biotin, a fluorescent marker, or a radioisotope, and is detected and/or quantitated using this label.

The term "detection reagent" denotes a reagent, which permits the detection and/or quantitation of an antibody, bound to an antigen. In some embodiments, the detection reagent is a colorimetric substrate for an enzyme that has been conjugated to an antibody. Addition of a suitable substrate to the antibody-enzyme conjugate results in the production of a colorimetric or fluorimetric signal (e.g., following the binding of the conjugated antibody to the antigen of interest). This definition also encompasses the use of biotin and avidin-based compounds (e.g., including but not limited to neutravidin and streptavidin) as part of the detection system.

The term "directly after" as used herein denotes the time span between taking a first sample and a second sample, which only encompasses the change of the sampling device and the actual time for taking the sample. In one embodiment, the term directly after denotes a time period of 5 minutes or less, in a further embodiment, of 3 minutes or less, in one preferred embodiment, of 2 minutes or less.

"Effector functions" refer to those biological activities attributable to the Fc region of an antibody, which vary with the antibody class. Examples of antibody effector functions include C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. On B-cells, it seems to function to suppress further immunoglobulin production and isotype switching to, for example, the IgE class. On macrophages, FcγRIIB acts to inhibit phagocytosis as mediated through FcγRIIA. On eosinophils and mast cells, the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils.

Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

An "effective amount" of an agent, e.g., a pharmaceutical formulation, refers to an amount effective, at dosages and for periods of time necessary, to achieve the desired therapeutic or prophylactic result.

The term "ELISA" denotes an enzyme-linked immunosorbent assay. Different ELISA formats and applications are known in the art (see, e.g., Crowther, "Enzyme-Linked Immunosorbent Assay (ELISA)," in Molecular Biomethods Handbook, Rapley et al. [eds.], pp. 595-617, Humana Press, Inc., Totowa, N J (1998); Harlow and Lane (eds.), Antibodies: A Laboratory Manual, Cold Spring Harbor Laboratory Press (1988); Ausubel et al. (eds.), Current Protocols in Molecular Biology, Ch. 11, John Wiley & Sons, Inc., New York (1994)).

One specific ELISA format is a so-called "direct ELISA". In this ELISA format a target, e.g. a polypeptide, present in a sample is detected. In a direct ELISA the sample, containing the target, is brought in contact with a solid phase, such as e.g., stationary or immobilized support (e.g., a microtiter plate well). The target, if present in the sample, becomes immobilized to the solid phase, and is thereafter detected directly using an enzyme-conjugated detection molecule. If the target is an antigen the detection molecule is an antibody specific for the antigen, or if the target is an antibody specific for an antigen the detection molecule is an enzyme-conjugated antibody specific for the antigen.

Another specific ELISA format is a so-called "indirect ELISA". In this ELISA format, an antigen (or an antibody) is immobilized to a solid phase (e.g., a microtiter plate well). Thereafter an antigen-specific antibody (or antigen) is added followed by the addition of a detection antibody specific for the antibody that specifically binds the antigen. This detection antibody can be a "species-specific" antibody (e.g., a goat anti-rabbit antibody).

Another specific ELISA format is a so-called "sandwich ELISA". In this format the antigen is immobilized on a solid phase (e.g., a microtiter plate well) via capture by an antibody specifically binding to the antigen (i.e., a capture antibody), which is (covalently or via a specific binding pair) immobilized on the solid phase. Generally, a sample comprising the antigen is added to the solid phase, followed by washing. If the antigen of interest is present in the sample, it is bound by the capture antibody to the solid phase.

The above-specified ELISA formats can be combined. A sandwich ELISA can be a "direct sandwich ELISA", wherein the captured antigen is detected directly by using an enzyme-conjugated antibody directed against the antigen. A sandwich ELISA can be an "indirect sandwich ELISA", wherein the captured antigen is detected indirectly by using an antibody directed against the antigen, which is then detected by another enzyme-conjugated antibody which binds the antigen-specific antibody either directly or via an attached label. With a reporter reagent, the third antibody is detected.

The term "Fc receptor" as used herein refers to activation receptors characterized by the presence of a cytoplasmic ITAM sequence associated with the receptor (see e.g. Ravetch, J. V. and Bolland, S., Annu. Rev. Immunol. 19 (2001) 275-290). Such receptors are FcγRI, FcγRIIA and FcγRIIIA. The term "no binding of FcγR" denotes that at an antibody concentration of 10 μg/ml the binding of an antibody as reported herein to NK cells is 10% or less of the binding found for anti-OX40L antibody LC.001 as reported in WO 2006/029879.

While IgG4 shows reduced FcR binding, antibodies of other IgG subclasses show strong binding. However, Pro238, Asp265, Asp270, Asn297 (loss of Fc carbohydrate), Pro329 and 234, 235, 236 and 237 Ile253, Ser254, Lys288, Thr307, Gln311, Asn434, and His435 are residues which provide if altered also reduce FcR binding (Shields, R. L., et al. J. Biol. Chem. 276 (2001) 6591-6604; Lund, J., et al., FASEB J. 9 (1995) 115-119; Morgan, A., et al., Immunology 86 (1995) 319-324; and EP 0 307 434). In one embodiment, the antibody as reported herein is of IgG1 or IgG2 subclass and comprises the mutation PVA236, GLPSS331, and/or L234A/L235A. In one embodiment, the antibody as reported herein is of IgG4 subclass and comprises the mutation L235E. In one embodiment, the antibody further comprises the mutation S228P.

The term "Fc-region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, MD (1991), NIH Publication 91-3242.

The antibodies as reported herein comprise as Fc-region, in one embodiment, an Fc-region derived from human origin. In one embodiment, the Fc-region comprises all parts of the human constant region. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat; Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, MD (1991), NIH Publication 91-3242). Antibodies of subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment, the Fc-region is a human Fc-region. In one embodiment, the Fc-region is of the human IgG4 subclass comprising the mutations S228P and/or L235E (numbering according to EU index of Kabat). In one embodiment, the Fc-region is of the human IgG1 subclass comprising the mutations L234A and L235A (numbering according to EU index of Kabat).

The terms "full length antibody", "intact antibody", and "whole antibody" are used herein interchangeably to refer to an antibody having a structure substantially similar to a native antibody structure, i.e. comprising two light chains and two heavy chains.

A "human antibody" is one, which possesses an amino acid sequence, which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "in-vitro" denotes either an artificial environment as such or that a process or reaction is performed within such an artificial environment.

The term "in-vivo" denotes the natural environment (e.g., an animal or a cell) of a compound or that a process or reaction is performed within its natural environment.

The term "immunoassay" denotes any technique that utilizes specifically binding molecules, such as antibodies, to capture and/or detect a specific target for qualitative or quantitative analysis. In general, an immunoassay is characterized by the following steps: 1) immobilization or capture of the analyte and 2) detection and measuring the analyte. The analyte can be captured, i.e. bound, on any solid surface, such as e.g. a membrane, plastic plate, or some other solid surface.

The term "linker" denotes a chemical linker or a single chain peptidic linker that covalently connects different entities of the blood-brain-barrier shuttle module and/or the fusion polypeptide and/or the conjugate as reported herein. The linker connects for example the brain effector entity to the monovalent binding entity. For example, if the monovalent binding entity comprises a CH2-CH3 Ig entity and a scFab directed to the blood-brain-barrier-receptor, then the linker conjugates the scFab to the C-terminal end of the CH3-CH2 Ig entity. The linker conjugating the brain effector entity to the monovalent binding entity (first linker) and the linker connecting the scFab to the C-terminal end of the CH2-CH3 Ig domain (second linker) can be the same or different.

Single chain peptidic linkers, comprising of from one to twenty amino acid residues joined by peptide bonds, can be used. In certain embodiments, the amino acids are selected from the twenty naturally occurring amino acids. In certain other embodiments, one or more of the amino acids are selected from glycine, alanine, proline, asparagine, glutamine and lysine. In other embodiments, the linker is a chemical linker. In certain embodiments, the linker is a single chain peptidic linker with an amino acid sequence with a length of at least 25 amino acid residues, in one preferred embodiment, with a length of 32 to 50 amino acid residues. In one embodiment, the peptidic linker is a (GxS)n linker with G=glycine, S=serine, (x=3, n=8, 9 or 10) or (x=4 and n=6, 7 or 8), in one embodiment, with x=4, n=6 or 7, in one preferred embodiment, with x=4, n=7. In one embodiment, the linker is (G4S)4 (SEQ ID NO: 02). In one embodiment, the linker is (G4S)6G2 (SEQ ID NO: 03).

Conjugation may be performed using a variety of chemical linkers. For example, the monovalent binding entity or the fusion polypeptide and the brain effector entity may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). The linker may be a "cleavable linker" facilitating release of the effector entity upon delivery to the brain. For example, an acid-labile linker, peptidase-sensitive linker, photo-labile linker, dimethyl linker or disulfide-containing linker (Chari et al, Cancer Res. 52 (1992) 127-131; U.S. Pat. No. 5,208,020) may be used.

Covalent conjugation can either be direct or via a linker. In certain embodiments, direct conjugation is by construction of a polypeptide fusion (i.e. by genetic fusion of the two genes encoding the monovalent binding entity towards the BBBR and effector entity and expressed as a single polypeptide (chain)). In certain embodiments, direct conjugation is by formation of a covalent bond between a reactive group on one of the two portions of the monovalent binding entity against the BBBR and a corresponding group or acceptor on the brain effector entity. In certain embodiments, direct conjugation is by modification (i.e. genetic modification) of one of the two molecules to be conjugated to include a reactive group (as non-limiting examples, a sulfhydryl group or a carboxyl group) that forms a covalent attachment to the other molecule to be conjugated under appropriate conditions. As one non-limiting example, a molecule (i.e. an amino acid) with a desired reactive group (i.e. a cysteine residue) may be introduced into, e.g., the monovalent binding entity towards the BBBR antibody and a disulfide bond formed with the neurological therapeutic antibody. Methods for covalent conjugation of nucleic acids to proteins are also known in the art (i.e., photo-crosslinking, see, e.g., Zatsepin et al. Russ. Chem. Rev. 74 (2005) 77-95). Conjugation may also be performed using a variety of linkers. For example, a monovalent binding entity and a effector entity may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptidic linkers, comprised of from one to twenty amino acid residues joined by peptide bonds, may also be used. In certain such embodiments, the amino acid residues are selected from the twenty naturally occurring amino acids. In certain other such embodiments, one or more of the amino acid residues are selected from glycine, alanine, proline, asparagine, glutamine and lysine. The linker may be a "cleavable linker" facilitating release of the effector entity upon delivery to the brain. For example, an acid-labile linker, peptidase-sensitive linker, photo-labile linker, dimethyl linker or disulfide-containing linker (Chari et al, Cancer Res. 52 (1992) 127-131; U.S. Pat. No. 5,208,020) may be used.

The term "monoclonal antibody" as used herein refers to an antibody obtained from a population of substantially homogeneous antibodies, i.e., the individual antibodies comprising the population are identical, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "monovalent binding entity" denotes a molecule able to bind specifically and in a monovalent binding mode to a BBBR. The blood brain shuttle module and/or conjugate as reported herein are characterized by the presence of a single unit of a monovalent binding entity i.e. the blood brain shuttle module and/or conjugate of the present invention comprise exactly one unit of the monovalent binding entity. The monovalent binding entity includes but is not limited to polypeptides, full length antibodies, antibody fragments including Fab, Fab', Fv fragments, single-chain antibody molecules such as e.g. single chain Fab, scFv. The monovalent binding entity can for example be a scaffold protein engineered using state of the art technologies like phage display or immunization. The monovalent binding entity can also be a polypeptide. In certain embodiments, the monovalent binding entity comprises a CH2-CH3 Ig domain and a single chain Fab (scFab) directed to a blood-brain-barrier-receptor. The scFab is coupled to the C-terminal end of the CH2-CH3 Ig domain by a linker. In certain embodiments, the scFab is directed to the transferrin receptor.

The term "monovalent binding mode" denotes a specific binding to the BBBR where the interaction between the monovalent binding entity and the BBBR takes place through one single epitope. The monovalent binding mode prevents any dimerization/multimerization of the BBBR due to a single epitope interaction point.

The monovalent binding mode prevents that the intracellular sorting of the BBBR is altered.

A "naked antibody" refers to an antibody that is not conjugated to a heterologous moiety (e.g., a cytotoxic moiety) or radiolabel. The naked antibody may be present in a pharmaceutical composition.

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable domain (VH), also called a variable heavy domain or a heavy chain variable region, followed by three constant heavy domains (CH1, CH2, and CH3). Similarly, from N- to C-terminus, each light chain has a variable domain (VL), also called a variable light domain or a light chain variable region, followed by a constant light (CL) domain.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the pharmaceutical composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

The term "sample" includes, but is not limited to, any quantity of a substance from a living thing or formerly living thing. Such living things include mice, monkeys, rats, rabbits, and other animals. In one embodiment, the sample is obtained from a monkey, especially a cynomolgus monkey, or a rabbit, or a mouse, or a rat.

The term "signal" as used herein encompasses any detectable physical change that can be used to indicate that a reaction has taken place, for example, binding of an antibody to its antigen. It is contemplated that signals in the form of fluorimetric or colorimetric products/reagents are specific forms of a signal and can be used in the method according to the current invention. In some embodiments of the present invention, the signal is assessed quantitatively.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly (methyl methacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

The terms "therapeutic (monoclonal) antibody" and "drug" are used interchangeably herein. These terms are used in the broadest sense and encompasses various antibody structures, including but not limited to monoclonal antibodies, polyclonal antibodies, and antibody fragments so long as they exhibit the desired antigen-binding activity.

The "transferrin receptor" ("TfR") is a transmembrane glycoprotein (with a molecular weight of about 180,000 Da) composed of two disulphide-bonded sub-units (each of apparent molecular weight of about 90,000 Da) involved in iron uptake in vertebrates. In one embodiment, the TfR as mentioned herein is human TfR comprising the amino acid sequence as in Schneider et al (Nature 311 (1984) 675-678), for example.

Multispecific Antibodies

In certain embodiments, the therapeutic antibody is a bispecific antibody. In one embodiment, the therapeutic antibody is a bispecific, trivalent antibody. In one preferred embodiment, the therapeutic antibody is a monoclonal, bispecific, trivalent antibody.

In certain embodiments, the therapeutic antibody is a multispecific antibody, e.g. a bispecific antibody. Multispecific antibodies are monoclonal antibodies that have binding specificities for at least two different antigens. In certain embodiments, one of the binding specificities is for a first antigen and the other is for a different second antigen. Bispecific antibodies can be prepared as full-length antibodies or antibody fragments. In one embodiment, the antibody is a bispecific antibody, which specifically binds to a first and a second antigen. In one embodiment, the bispecific antibody has i) a first binding specificity that specifically binds to a first antigen, and ii) a second binding specificity that specifically binds to a second antigen. In one embodiment, the antibody is a bispecific, trivalent antibody. In one preferred embodiment, the antibody is a monoclonal, bispecific, trivalent antibody.

In one embodiment, one of the binding sites specifically binds to a BBBR.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P., et al., Proc. Natl. Acad. Sci. USA 90 (1993) 6444-6448); and using single-chain Fv (scFv) dimers (see, e.g., Gruber, M., et al., J. Immunol. 152 (1994) 5368-5374); and preparing trispecific antibodies as described, e.g., in Tutt, A., et al., J. Immunol. 147 (1991) 60-69).

Multispecific antibodies are described in WO 2009/080251, WO 2009/080252, WO 2009/080253, WO 2009/080254, WO 2010/112193, WO 2010/115589, WO 2010/136172, WO 2010/145792, or WO 2010/145793.

Different bispecific antibody formats are known.

Exemplary bispecific antibody formats for which the methods as reported herein can be used are the CrossMab format (=CrossMab): a multispecific IgG antibody comprising a first Fab fragment and a second Fab fragment, wherein in the first Fab fragment
   a) only the CH1 and CL domains are replaced by each other (i.e. the light chain of the first Fab fragment comprises a VL and a CH1 domain and the heavy chain of the first Fab fragment comprises a VH and a CL domain);
   b) only the VH and VL domains are replaced by each other (i.e. the light chain of the first Fab fragment comprises a VH and a CL domain and the heavy chain of the first Fab fragment comprises a VL and a CH1 domain); or
   c) the CH1 and CL domains are replaced by each other and the VH and VL domains are replaced by each other (i.e. the light chain of the first Fab fragment comprises a VH and a CH1 domain and the heavy chain of the first Fab fragment comprises a VL and a CL domain); and
wherein the second Fab fragment comprises a light chain comprising a VL and a CL domain, and a heavy chain comprising a VH and a CH1 domain;
the CrossMab may comprises a first heavy chain including a CH3 domain and a second heavy chain including a CH3 domain, wherein both CH3 domains are engineered in a complementary manner by respective amino acid substitutions, in order to support heterodimerization of the first heavy chain and the modified second heavy chain, e.g. as disclosed in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, or WO 2013/096291 (incorporated herein by reference);
the one-armed single chain format (=one-armed single chain antibody): antibody comprising a first binding site that specifically binds to a first antigen and a second binding site that specifically binds to a second antigen, whereby the individual chains are as follows
   light chain (variable light chain domain+light chain kappa constant domain)
   combined light/heavy chain (variable light chain domain+light chain constant domain+peptidic linker+variable heavy chain domain+CH1+Hinge+CH2+CH3 with knob mutation)
   heavy chain (variable heavy chain domain+CH1+Hinge+CH2+CH3 with hole mutation);
the two-armed single chain format (=two-armed single chain antibody): antibody comprising a first binding site that specifically binds to a first antigen and a second binding site that specifically binds to a second antigen, whereby the individual chains are as follows
   combined light/heavy chain 1 (variable light chain domain+light chain constant domain+peptidic linker+variable heavy chain domain+CH1+Hinge+CH2+CH3 with hole mutation)
   combined light/heavy chain 2 (variable light chain domain+light chain constant domain+peptidic linker+variable heavy chain domain+CH1+Hinge+CH2+CH3 with knob mutation);
the common light chain bispecific format (=common light chain bispecific antibody): antibody comprising a first binding site that specifically binds to a first antigen and a second binding site that specifically binds to a second antigen, whereby the individual chains are as follows
   light chain (variable light chain domain+light chain constant domain)
   heavy chain 1 (variable heavy chain domain+CH1+Hinge+CH2+CH3 with hole mutation)
   heavy chain 2 (variable heavy chain domain+CH1+Hinge+CH2+CH3 with knob mutation);
the bispecific Fab format: Fab comprising two (non-overlapping) paratopes in a complementary pair of a VH and a VL domain, wherein the first paratope comprises (consists of) amino acid residues from CDR1 and CDR3 of the VL domain and CDR2 of the VH domain, and the second paratope comprises (consists of) residues from CDR1 and CDR3 of the VH domain and CDR2 of the VL domain; the term "non-overlapping" in this context indicates that an amino acid residue that is comprised within the first paratope of the bispecific Fab is not comprised in the second paratope, and an amino acid that is comprised within the second paratope of the bispecific Fab is not comprised in the first paratope;
the TCB format: a bispecific antibody comprising
   a first and a second Fab fragment, wherein each binding site of the first and the second Fab fragment specifically bind to a second antigen,
   a third Fab fragment, wherein the binding site of the third Fab fragment specifically binds to a first antigen, and wherein the third Fab fragment comprises a domain crossover such that the variable light chain domain (VL) and the variable heavy chain domain (VH) are replaced by each other, and
   an Fc-region comprising a first Fc-region polypeptide and a second Fc-region polypeptide,
   wherein the first and the second Fab fragment each comprise a heavy chain fragment and a full-length light chain,
   wherein the C-terminus of the heavy chain fragment of the first Fab fragment is fused to the N-terminus of the first Fc-region polypeptide,
   wherein the C-terminus of the heavy chain fragment of the second Fab fragment is fused to the N-terminus of the variable light chain domain of the third Fab fragment and the C-terminus of the heavy chain constant domain 1 of the third Fab fragment is fused to the N-terminus of the second Fc-region polypeptide.
the brain-shuttle format (BS): a bispecific antibody comprising
   a) one (full length) antibody comprising two pairs each of a (full length) antibody light chain and a (full length) antibody heavy chain, wherein the binding sites formed by each of the pairs of the (full length) heavy chain and the (full length) light chain specifically bind to a first antigen, and
   b) one additional Fab fragment, wherein the additional Fab fragment is fused to any C-terminus of one heavy chain of the (full length) antibody, wherein the binding site of the additional Fab fragment specifically binds to a second antigen,
   wherein the additional Fab fragment specifically binding to the second antigen comprises a domain crossover such that the constant light chain domain (CL) and the constant heavy chain domain 1 (CH1) are replaced by each other, and
   wherein the first antigen is the brain target and the second antigen is human transferrin receptor.

In one embodiment, the bispecific antibody is a CrossMab.

In one embodiment, the bispecific antibody is a one-armed single chain antibody.

In one embodiment, the bispecific antibody is a two-armed single chain antibody.

In one embodiment, the bispecific antibody is a common light chain bispecific antibody.

In one embodiment, the bispecific antibody is a bispecific Fab.

In one embodiment, the bispecific antibody is a TCB.

In one embodiment, the bispecific antibody is a BS.

Multivalent, multispecific antibodies specifically bind to different targets, most likely with different affinities and complex stabilities for each target. Only a fully active multivalent, multispecific antibody can bind to all targets and shows the full biological activity in a corresponding assay.

A. Exemplary Bispecific Antibody: Anti-Human A-Beta/Human Transferrin Receptor Antibody In certain embodiments, the therapeutic antibody to be determined in a method according to the current invention is an antibody that binds to human A-beta and human transferrin receptor. This antibody is a bispecific antibody consisting of a full-length core antibody and a fused Fab fragment in which certain domains are crosswise exchanged. Thus, the resulting bispecific antibody is asymmetric. Therefore, the bispecific antibodies are produced using the heterodimerization technology called knobs-into-holes using a first heavy chain with the so-called knob mutations (HC-knob) and a second heavy chain with the so-called hole mutations (HChole).

Exemplary antibody 0012 is composed of four polypeptides that have the amino acid sequence of SEQ ID NO: 04 to 07.

Exemplary antibody 0015 is composed of four polypeptides that have the amino acid sequence of SEQ ID NO: 08 to 11.

Exemplary antibody 0020 is composed of three polypeptides that have the amino acid sequence of SEQ ID NO: 12 to 14.

Exemplary antibody 0024 is composed of four polypeptides that have the amino acid sequence of SEQ ID NO: 15 to 18.

In one aspect, the therapeutic antibody is a bispecific antibody comprising
  a) one full length antibody comprising two pairs each of a full length antibody light chain and a full length antibody heavy chain, wherein the binding sites formed by each of the pairs of the full length heavy chain and the full length light chain specifically bind to a first antigen, and
  b) one additional Fab fragment, wherein the additional Fab fragment is fused to the C-terminus of one heavy chain of the full length antibody, wherein the binding site of the additional Fab fragment specifically binds to a second antigen,
  wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
  wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
  wherein the additional Fab fragment specifically binding to the second antigen comprises a domain crossover such that the constant light chain domain (CL) and the constant heavy chain domain 1 (CH1) are replaced by each other, and wherein the first antigen is human A-beta protein and the second antigen is human transferrin receptor.

In another embodiment, the therapeutic antibody is a bispecific antibody comprising
  a) one full length antibody comprising two pairs each of a full length antibody light chain and a full length antibody heavy chain, wherein the binding sites formed by each of the pairs of the full length heavy chain and the full length light chain specifically bind to a first antigen, and
  b) one additional Fab fragment, wherein the additional Fab fragment is fused to the C-terminus of one heavy chain of the full length antibody, wherein the binding site of the additional Fab fragment specifically binds to a second antigen,
  wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
  wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
  wherein the additional Fab fragment specifically binding to the second antigen comprises a domain crossover such that the constant light chain domain (CL) and the constant heavy chain domain 1 (CH1) are replaced by each other,
  wherein the first antigen is human A-beta protein and the second antigen is human transferrin receptor,
  wherein the human A-beta binding site comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 19 and a light chain variable domain (VL) sequence having at least 90%, 91%, 92%, 93%, 94%, 95%, 96%, 97%, 98%, 99%, or 100% sequence identity to the amino acid sequence of SEQ ID NO: 20, and
  wherein the human transferrin receptor binding site comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 21 and a light chain variable domain (VL) sequence having at least 90%, 91%, 92%, 93%, 94%, 95%, 96%, 97%, 98%, 99%, or 100% sequence identity to the amino acid sequence of SEQ ID NO: 22.

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but a binding site comprising that sequence retains the ability to bind to its antigen. In certain embodiments, a total of 1 to 10 amino acids have been substituted, inserted and/or deleted in SEQ ID NO: 19 or 21. In certain embodiments, substitutions, insertions, or deletions occur in regions outside the HVRs (i.e., in the FRs).

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but a binding site comprising that sequence retains the ability to bind to its antigen. In certain embodiments, a total of 1 to 10 amino acids have been substituted, inserted and/or deleted in SEQ ID NO: 20 or 22. In certain embodiments, substitutions, insertions, or deletions occur in regions outside the HVRs (i.e., in the FRs).

In one embodiment, the human A-beta binding site comprises the VH sequence as in SEQ ID NO: 19, including post-translational modifications of that sequence and the VL sequence as in SEQ ID NO: 20.

In one embodiment, the human transferrin receptor-binding site comprises the VH sequence as in SEQ ID NO: 21, including post-translational modifications of that sequence and the VL sequence as in SEQ ID NO: 22.

In one embodiment, the bispecific antibody comprises
i) a light chain that has a sequence identity to SEQ ID NO: 23 of at least 70%, at least 80%, at least 90%, or 95% or more,
ii) a heavy chain that has a sequence identity to SEQ ID NO: 24 of at least 70%, at least 80%, at least 90%, or 95% or more,
iii) a light chain that has a sequence identity to SEQ ID NO: 25 of at least 70%, at least 80%, at least 90%, or 95% or more, and
iv) a heavy chain Fab fragment that has a sequence identity to SEQ ID NO: 26 of at least 70%, at least 80%, at least 90%, or 95% or more,
wherein

```
SEQ ID NO: 23 has the amino acid sequence
DIVLTQSPATLSLSPGERATLSCRASQSVSSSYLAWYQQKPGQAPRLL

IYGASSRATGVPARFSGSGSGTDFTLTISSLEPEDFATYYCLQIYNMPIT

FGQGTKVEIKRTVAAPSVFIFPPSDRKLKSGTASVVCLLNNFYPREAK

VQWKVDNALQSGNSQESVTEQDSKDSTYSLSSTLTLSKADYEKHKV

YACEVTHQGLSSPVTKSFNRGEC,

SEQ ID NO: 24 has the amino acid sequence
QVELVESGGGLVQPGGSLRLSCAASGFTFSSYAMSWVRQAPGKGLE

WVSAINASGTRTYYADSVKGRFTISRDNSKNTLYLQMNSLRAEDTAV

YYCARGKGNTHKPYGYVRYFDVWGQGTLVTVSSASTKGPSVFPLAP

SSKSTSGGTAALGCLVEDYFPEPVTVSWNSGALTSGVHTFPAVLQSS

GLYSLSSVVTVPSSSLGTQTYICNVNHKPSNTKVDEKVEPKSCDKTHT

CPPCPAPELLGGPSVFLFPPKPKDTLMISRTPEVTCVVVDVSHEDPEV

KFNWYVDGVEVHNAKTKPREEQYNSTYRVVSVLTVLHQDWLNGKE

YKCKVSNKALPAPIEKTISKAKGQPREPQVCTLPPSRDELTKNQVSLS

CAVKGFYPSDIAVEWESNGQPENNYKTTPPVLDSDGSFFLVSKLTVD

KSRWQQGNVFSCSVMHEALHNHYTQKSLSLSPG,

SEQ ID NO: 25 has the amino acid sequence
AIQLTQSPSSLSASVGDRVTITCRASQSISSYLAWYQQKPGKAPKLLIY

RASTLASGVPSRFSGSGSGTDFTLTISSLQPEDFATYYCQQNYASSNV

DNTFGGGTKVEIKSSASTKGPSVFPLAPSSKSTSGGTAALGCLVKDYF

PEPVTVSWNSGALTSGVHTFPAVLQSSGLYSLSSVVTVPSSSLGTQTY

ICNVNHKPSNTKVDKKVEPKSC, and

SEQ ID NO: 26 has the amino acid sequence
QSMQESGPGLVKPSQTLSLTCTVSGFSLSSYAMSWIRQHPGKGLEWI

GYIWSGGSTDYASWAKSRVTISKTSTTVSLKLSSVTAADTAVYYCAR

RYGTSYPDYGDASGFDPWGQGTLVTVSSASVAAPSVFIFPPSDEQLKS

GTASVVCLLNNFYPREAKVQWKVDNALQSGNSQESVTEQDSKDSTY

SLSSTLTLSKADYEKHKVYACEVTHQGLSSPVTKSFNRGEC.
```

In another embodiment, the therapeutic antibody is a bispecific antibody comprising a) one full length antibody comprising two pairs each of a full length antibody light chain and a full length antibody heavy chain, wherein the binding sites formed by each of the pairs of the full length heavy chain and the full length light chain specifically bind to a first antigen, and b) one additional Fab fragment, wherein the additional Fab fragment is fused to the C-terminus of one heavy chain of the full length antibody, wherein the binding site of the additional Fab fragment specifically binds to a second antigen, wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat), wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index), wherein the additional Fab fragment specifically binding to the second antigen comprises a domain crossover such that the constant light chain domain (CL) and the constant heavy chain domain 1 (CH1) are replaced by each other, wherein the first antigen is human A-beta protein and the second antigen is human transferrin receptor, wherein the human A-beta binding site comprises a heavy chain variable domain (VH) that has the amino acid sequence of SEQ ID NO: 19 and a light chain variable domain (VL) that has the amino acid sequence of SEQ ID NO: 20, and wherein the human transferrin receptor-binding site comprises a heavy chain variable domain (VH) that has the amino acid sequence of SEQ ID NO: 21 and a light chain variable domain (VL) that has the amino acid sequence of SEQ ID NO: 22.

In another embodiment, the therapeutic antibody is a bispecific antibody comprising a) one full length antibody comprising two pairs each of a full length antibody light chain and a full length antibody heavy chain, wherein the binding sites formed by each of the pairs of the full length heavy chain and the full length light chain specifically bind to a first antigen, wherein the full length antibody comprises an Fc-region that is formed by the Fc-region polypeptides, each comprising the CH1, CH2 and CH3 domain, of the two full length heavy chains, and b) one additional Fab fragment, wherein the additional Fab fragment is fused to the C-terminus of one heavy chain of the full length antibody, wherein the binding site of the additional Fab fragment specifically binds to a second antigen, wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat), wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index), wherein the additional Fab fragment specifically binding to the second antigen comprises a domain crossover such that the constant light chain domain (CL) and the constant heavy chain domain 1 (CH1) are replaced by each other, wherein the first antigen is human A-beta protein and the second antigen is human transferrin receptor, wherein the human A-beta binding site comprises a heavy chain variable domain (VH) that has the amino acid sequence of SEQ ID NO: 19 and a light chain variable domain (VL) that has the amino acid sequence of SEQ ID NO: 20, wherein the human transferrin receptor binding site comprises a heavy chain variable domain (VH) that has the amino acid sequence of SEQ ID NO: 21 and a light chain variable domain (VL) that has the amino acid sequence of SEQ ID NO: 22, and wherein the Fc-region polypeptides are a) of the human subclass IgG1,
b) of the human subclass IgG4,
c) of the human subclass IgG1 with the mutations L234A, L235A and P329G,
d) of the human subclass IgG4 with the mutations S228P, L235E and P329G,
e) of the human subclass IgG1 with the mutations L234A, L235A and P329G in both Fc-region polypeptides and the mutations T366W and S354C in one Fc-region polypeptide and the mutations T366S, L368A, Y407V and Y349C in the respective other Fc-region polypeptide,
f) of the human subclass IgG4 with the mutations S228P and P329G in both Fc-region polypeptides and the mutations T366W and S354C in one Fc-region polypeptide and the mutations T366S, L368A, Y407V and Y349C in the respective other Fc-region polypeptide,
g) of the human subclass IgG1 with the mutations L234A, L235A, P329G, I253A, H310A and H435A in both Fc-region polypeptides and the mutations T366W and S354C in one Fc-region polypeptide and the mutations T366S, L368A, Y407V and Y349C in the respective other Fc-region polypeptide, or
h) of the human subclass IgG1 with the mutations L234A, L235A, P329G, M252Y, S254T and T256E in both Fc-region polypeptides and the mutations T366W and S354C in one Fc-region polypeptide and the mutations T366S, L368A, Y407V and Y349C in the respective other Fc-region polypeptide.

B. Exemplary Anti-Transferrin Receptor Antibodies

The anti-transferrin receptor binding site of a therapeutic antibody to be determined in a method according to the current invention have an off-rate for binding to the human transferrin receptor that is within a certain range in order to ensure proper BBB shuttling. This range is defined at the one end by the off-rate of the murine anti-transferrin receptor antibody 128.1 (variable domain amino acid sequences given in SEQ ID NO: 27 and 28) determined by surface plasmon resonance for the cynomolgus transferrin receptor and at the other end by 5% of that off-rate (i.e. a 20-times slower dissociation). The off-rate for the human transferrin receptor should be between and including 0.1 l/s and 0.005 l/s.

One aspect as reported herein is an anti-transferrin receptor antibody that specifically binds to human transferrin receptor and cynomolgus transferrin receptor, which comprises i) a humanized heavy chain variable domain derived from the heavy chain variable domain of SEQ ID NO: 29, and ii) a humanized light chain variable domain derived from the light chain variable domain of SEQ ID NO: 30, wherein the antibody has an off-rate for the human transferrin receptor that is equal to or less than (i.e. at most) the off-rate of the anti-transferrin receptor antibody 128.1 for the cynomolgus transferrin receptor, whereby the off-rates are determined by surface plasmon resonance, and whereby the anti-transferrin receptor antibody 128.1 has a heavy chain variable domain of SEQ ID NO: 27 and a light chain variable domain of SEQ ID NO: 28.

In one embodiment, the off-rate for the human transferrin receptor is between and including 0.1 l/s and 0.005 l/s.

In one embodiment, the antibody has in the light chain variable domain at position 80 a proline amino acid residue (P) (numbering according to Kabat).

In one embodiment, the antibody has in the light chain variable domain at position 91 an asparagine amino acid residue (N) (numbering according to Kabat).

In one embodiment, the antibody has in the light chain variable domain at position 93 an alanine amino acid residue (A) (numbering according to Kabat).

In one embodiment, the antibody has in the heavy chain variable domain at position 100 g a serine amino acid residue (S) (numbering according to Kabat).

In one embodiment, the antibody has in the heavy chain variable domain at position 100 g a glutamine amino acid residue (Q) (numbering according to Kabat).

In one embodiment, the antibody has in the heavy chain variable domain at position 65 a serine amino acid residue (S) (numbering according to Kabat).

In one embodiment, the antibody has in the heavy chain variable domain at position 105 a glutamine amino acid residue (Q) (numbering according to Kabat).

In one embodiment, the antibody the antibody has in the light chain variable domain at position 80 a proline amino acid residue (P), in the light chain variable domain at position 91 an asparagine amino acid residue (N), in the light chain variable domain at position 93 an alanine amino acid residue (A), in the heavy chain variable domain at position 100 g a serine amino acid residue (S), in the heavy chain variable domain at position 65 a serine amino acid residue (S), and in the heavy chain variable domain at position 105 a glutamine amino acid residue (Q) (numbering according to Kabat).

In one embodiment, the antibody the antibody has in the light chain variable domain at position 80 a proline amino acid residue (P), in the light chain variable domain at position 91 an asparagine amino acid residue (N), in the light chain variable domain at position 93 an alanine amino acid residue (A), in the heavy chain variable domain at position 100 g a glutamine amino acid residue (Q), in the heavy chain variable domain at position 65 a serine amino acid residue (S), and in the heavy chain variable domain at position 105 a glutamine amino acid residue (Q) (numbering according to Kabat).

Such anti-transferrin receptor bispecific antibodies can be used as blood-brain-barrier shuttle module to deliver a brain effector entity across the blood-brain-barrier into the brain. The blood-brain-barrier shuttle module is a monovalent binding entity that specifically binds to the human transferrin receptor. The anti-transferrin receptor bispecific antibodies when used as blood-brain-barrier shuttle module are useful, e.g., for the diagnosis or treatment of neurological disorders, such as Alzheimer's disease, Parkinson's Disease and Alzheimer's Disease with Parkinson's Disease co-morbidity.

In one embodiment, the anti-transferrin receptor binding site of the therapeutic antibody comprises the heavy chain variable domain of SEQ ID NO: 31 and the light chain variable domain of SEQ ID NO: 32 which reflect with respect to the human transferrin receptor the binding properties of the murine antibody 128.1 with respect to the cynomolgus transferrin receptor regarding the binding off-rate.

In one embodiment, the anti-transferrin receptor binding site of the therapeutic antibody specifically binds to human transferrin receptor (huTfR) and cynomolgus transferrin receptor (cyTfR) and comprises i) a humanized heavy chain variable domain derived from the heavy chain variable domain of SEQ ID NO: 29 and ii) a humanized light chain variable domain derived from the light chain variable domain of SEQ ID NO: 30, wherein the light chain variable domain has at position 80 a proline amino acid residue (P), at position 91 an asparagine amino acid residue (N) and at position 93 an alanine amino acid residue (A) (numbering according to Kabat).

In one embodiment, the anti-transferrin receptor binding site of the therapeutic antibody further has in the heavy chain variable domain at position 100 g a serine amino acid residue (S) (numbering according to Kabat).

In one embodiment, the anti-transferrin receptor binding site of the therapeutic antibody further has in the heavy chain variable domain at position 65 a serine amino acid residue (S) (numbering according to Kabat).

In one embodiment, the anti-transferrin receptor binding site of the therapeutic antibody further has in the heavy chain variable domain at position 105 a glutamine amino acid residue (Q) (numbering according to Kabat).

In one embodiment, the anti-transferrin receptor binding site of the therapeutic antibody specifically binds to human transferrin receptor (huTfR) and cynomolgus transferrin receptor (cyTfR) and comprises i) a humanized heavy chain variable domain derived from the heavy chain variable domain of SEQ ID NO: 29 and ii) a humanized light chain variable domain derived from the light chain variable domain of SEQ ID NO: 30, wherein the therapeutic antibody has an off-rate in the unit l/s for the human transferrin receptor that is equal to or less than (i.e. at most) the off-rate in the unit l/s of the anti-transferrin receptor antibody 128.1 for the cynomolgus transferrin receptor, whereby the off-rates are determined by surface plasmon resonance, and whereby the anti-transferrin receptor antibody 128.1 has a heavy chain variable domain of SEQ ID NO: 27 and a light chain variable domain of SEQ ID NO: 28.

In one embodiment, the anti-transferrin receptor binding site of the therapeutic antibody has an off-rate in the unit l/s for the human transferrin receptor that is i) equal to or less than (i.e. at most) the off-rate in the unit l/s of the anti-transferrin receptor antibody 128.1 for the cynomolgus transferrin receptor and ii) equal to or more than (i.e. at least) 5% of the off-rate in the unit l/s of the anti-transferrin receptor antibody 128.1 for the cynomolgus transferrin receptor.

In one embodiment, the anti-transferrin receptor binding site of the therapeutic antibody comprises (a) a HVR-H1 comprising the amino acid sequence of SEQ ID NO: 33; (b) a HVR-H2 comprising the amino acid sequence of SEQ ID NO: 34; (c) a HVR-H3 comprising the amino acid sequence of SEQ ID NO: 35, 36 or 37, in one preferred embodiment, SEQ ID NO: 36; (d) a HVR-L1 comprising the amino acid sequence of SEQ ID NO: 38; (e) a HVR-L2 comprising the amino acid sequence of SEQ ID NO: 39; and (f) a HVR-L3 comprising the amino acid sequence of SEQ ID NO: 40.

In any of the above embodiments, an anti-transferrin receptor-binding site is humanized. In one embodiment, an anti-transferrin receptor-binding site comprises HVRs as in any of the above embodiments, and further comprises an acceptor human framework, e.g. a human immunoglobulin framework or a human consensus framework.

In one embodiment, the antibody is a bispecific antibody comprising at least one pair of a heavy chain variable domain of SEQ ID NO: 31 and a light chain variable domain of SEQ ID NO: 32 forming a binding site for the transferrin receptor and at least one pair of a heavy chain variable domain of SEQ ID NO: 41 and a light chain variable domain of SEQ ID NO: 42 binding site for human CD20. In one embodiment, the heavy chain variable region comprises a replacement of the amino acid residue at Kabat position 11 with any amino acid but leucine. In one embodiment, the substitution comprises a replacement of the amino acid residue at Kabat position 11 with a nonpolar amino acid. In one preferred embodiment, the substitution comprises a replacement of the amino acid residue at Kabat position 11 in the heavy chain variable domain of SEQ ID NO: 41 with an amino acid residue selected from the group consisting of valine, leucine, isoleucine, serine, and phenylalanine.

In one embodiment, the antibody is a bispecific antibody comprising at least one pair of a heavy chain variable domain of SEQ ID NO: 31 and a light chain variable domain of SEQ ID NO: 32 forming a binding site for the transferrin receptor and at least one pair of a heavy chain variable domain of SEQ ID NO: 43 and a light chain variable domain of SEQ ID NO: 44 binding site for human alpha-synuclein.

In one embodiment, the antibody is a bispecific antibody comprising at least one pair of a heavy chain variable domain of SEQ ID NO: 31 and a light chain variable domain of SEQ ID NO: 32 forming a binding site for the transferrin receptor and at least one pair of a humanized heavy chain variable domain derived from SEQ ID NO: 45 and a humanized light chain variable domain derived from SEQ ID NO: 46 binding site for human alpha-synuclein.

In one embodiment, the antibody is a bispecific antibody comprising at least one pair of a heavy chain variable domain of SEQ ID NO: 31 and a light chain variable domain of SEQ ID NO: 32 forming a binding site for the transferrin receptor and at least one pair of a humanized heavy chain variable domain derived from SEQ ID NO: 47 and a humanized light chain variable domain derived from SEQ ID NO: 48 binding site for human alpha-synuclein.

In one embodiment, the antibody is a bispecific antibody comprising at least one pair of a heavy chain variable domain of SEQ ID NO: 31 and a light chain variable domain of SEQ ID NO: 32 forming a binding site for the transferrin receptor and at least one pair of a humanized heavy chain variable domain derived from SEQ ID NO: 49 and a humanized light chain variable domain derived from SEQ ID NO: 50 binding site for human alpha-synuclein.

In one embodiment, the antibody is a bispecific antibody comprising at least one pair of a heavy chain variable domain of SEQ ID NO: 31 and a light chain variable domain of SEQ ID NO: 32 forming a binding site for the transferrin receptor and at least one pair of a humanized heavy chain variable domain derived from SEQ ID NO: 51 and a humanized light chain variable domain derived from SEQ ID NO: 52 binding site for human alpha-synuclein.

In one embodiment, the antibody is a bispecific antibody comprising at least one pair of a heavy chain variable domain of SEQ ID NO: 31 and a light chain variable domain of SEQ ID NO: 32 forming a binding site for the transferrin receptor and at least one pair of a humanized heavy chain variable domain derived from SEQ ID NO: 53 and a humanized light chain variable domain derived from SEQ ID NO: 54 binding site for human alpha-synuclein.

In one embodiment, the antibody is a bispecific antibody comprising at least one pair of a heavy chain variable domain of SEQ ID NO: 31 and a light chain variable domain of SEQ ID NO: 32 forming a binding site for the transferrin receptor and a binding site for i) glucocerebrosidase that has the amino acid sequence of SEQ ID NO: 55, or ii) a functional variant of SEQ ID NO: 55 having at least 70% sequence identity, or iii) a functional variant of SEQ ID NO: 55 having one or more amino acid mutations, deletions or insertions, or iv) a truncated functional variant of SEQ ID NO: 55 having at least one amino acid residue at the N-terminus or the C-terminus or within the amino acid sequence deleted, or v) a combination of iii) and iv).

In another embodiment, the therapeutic antibody is a multispecific antibody. In one such embodiment, the multispecific antibody comprises a first antigen-binding site, which binds TfR, and a second antigen-binding site, which binds a brain antigen. In one such aspect, the brain antigen is selected from the group consisting of: beta-secretase 1 (BACE1), Abeta, epidermal growth factor receptor (EGFR), human epidermal growth factor receptor 2 (HER2), tau, apolipoprotein E (ApoE), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), glucocerebrosidase, and caspase 6. In another embodiment, the multispecific antibody binds both TfR and BACE1. In another embodiment, the multispecific antibody binds both TfR and Abeta. In another embodiment, the multispecific antibody binds both TfR and alpha synuclein. In another embodiment, the multispecific antibody binds both TfR and CD20. In another embodiment, the multispecific antibody binds both TfR and glucocerebrosidase. In another embodiment, the therapeutic compound is a neurological disorder therapeutic antibody.

In one embodiment, the effector function is reduced or eliminated by at least one modification of the Fc region. In one embodiment, the effector function or complement activation function is reduced or eliminated by deletion of all or a portion of the Fc region, or by engineering the antibody such that it does not include an Fc region or non-Fc region competent for effector function or complement activation function. In one embodiment, the at least one modification of the Fc region is selected from: a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 30 335, 338, 340, 373, 376, 382, 388, 389, 414, 416, 419, 434, 435, 437, 438, and 439; a point mutation of the Fc region to impair binding to C1q selected from the following positions: 270, 322, 329, and 321; eliminating some or all of the Fc region, and a point mutation at position 132 of the CH1 domain. In one embodiment, the modification is a point mutation of the Fc region to impair binding to C1q selected from the following positions: 270, 322, 329, and 321. In another embodiment, the modification is elimination of some or all of the Fc region. In another embodiment, complement-triggering function is reduced or eliminated by deletion of all or a portion of the Fc region, or by engineering the antibody such that it does not include an Fc region that engages the complement pathway. In one embodiment, the antibody is selected from a Fab or a single chain antibody. In another embodiment, the non-Fc region of the antibody is modified to reduce or eliminate activation of the complement pathway by the antibody. In one embodiment, the modification is a point mutation of the CH1 region to impair binding to C3. In one embodiment, the point mutation is at position 132 (see, e.g., Vidarte et al., J. Biol. Chem. 276 (2001) 38217-38223).

In one aspect of the above embodiment, the affinity of the antibody for TfR is decreased, as measured relative to a wild-type antibody of the same isotype not having lowered affinity for TfR. In one such aspect, the antibody has a $K_D$ or $IC_{50}$ for TfR of about 1 pM to about 100 μM.

In one embodiment, the antibody as reported herein is effector function silent. In one embodiment, the antibody has no effector function. In one embodiment, the antibody is of the human IgG1 subclass and has the mutations L234A, L235A and P329G in both heavy chains (numbering according to the EU index of Kabat).

In one embodiment, the antibody is
a) a full length antibody of the human subclass IgG1, or
b) a full length antibody of the human subclass IgG4, or
c) a full-length antibody of the human subclass IgG1 with the mutations L234A, L235A and P329G,
d) a full-length antibody of the human subclass IgG4 with the mutations S228P, L235E and optionally P329G,
e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
f) a full-length antibody of the human subclass IgG4 with the mutations S228P and optionally P329G in both heavy chains and the mutations T366W and S354C in one heavy chain and the mutations T366S, L368A, Y407V and Y349C in the respective other heavy chain.

In one embodiment, the bispecific therapeutic antibody comprises
  i) a homodimeric Fc-region of the human IgG1 subclass optionally with the mutations P329G, L234A and L235A, or
  ii) a homodimeric Fc-region of the human IgG4 subclass optionally with the mutations P329G, S228P and L235E, or
  iii) a heterodimeric Fc-region whereof
    a) one Fc-region polypeptide comprises the mutation T366W, and the other Fc-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C, or
  iv) a heterodimeric Fc-region of the human IgG4 subclass whereof both Fc-region polypeptides comprise the mutations P329G, L234A and L235A and
    a) one Fc-region polypeptide comprises the mutation T366W, and the other Fc-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C, or
  v) a heterodimeric Fc-region of the human IgG4 subclass whereof both Fc-region polypeptides comprise the mutations P329G, S228P and L235E and
    a) one Fc-region polypeptide comprises the mutation T366W, and the other Fe-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C.

Immunoassays

The principles of different immunoassays are described in the art. For example, Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Monoclonal antibodies and their constant domains contain a number of reactive amino acid side chains for conjugating to a member of a binding pair, such as a polypeptide/protein, a polymer (e.g. PEG, cellulose or polystyrol), or an enzyme. Chemical reactive groups of amino acids are, for example, amino groups (lysins, alpha-amino groups), thiol groups (cystins, cysteines, and methionins), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pages 50-100.

One of the most common reactive groups of antibodies is the aliphatic 8-amine of the amino acid lysine. In general, nearly all antibodies contain abundant lysine. Lysine amines are reasonably good nucleophiles above pH 8.0 (pKa=9.18) and therefore react easily and cleanly with a variety of reagents to form stable bonds. Amine-reactive reagents react primarily with lysins and the α-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiffs base). A Schiffs base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with N-terminal and 8-amine groups of amino acids to form amide linkages. The anhydride rings open to create multivalent, metal-chelating arms able to bind tightly to metals in a coordination complex.

Another common reactive group in antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiotreitol (DTT) is required to generate the reactive free thiol. Thiol-reactive reagents are those that will couple to thiol groups on polypeptides, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succinimidyl (acetylthio) acetate (SATA), and sulfosuccinimidyl 6-[3-(2-pyridyldithio) propionamido] hexanoate (Sulfo-LC-SPDP) to provide efficient ways of introducing multiple sulfhydryl groups via reactive amino groups. Haloacetyl derivatives, e.g. iodoacetamides, form thioether bonds and are reagents for thiol modification. Further useful reagents are maleimides. The reaction of maleimides with thiol-reactive reagents is essentially the same as with iodoacetamides. Maleimides react rapidly at slight acidic to neutral pH.

Another common reactive group in antibodies are carboxylic acids. Antibodies contain carboxylic acid groups at the C-terminal position and within the side chains of aspartic acid and glutamic acid. The relatively low reactivity of carboxylic acids in water usually makes it difficult to use these groups to selectively modify polypeptides and antibodies. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic ε-amines of lysine to form a stable amide bond. Protein crosslinking can occur when the pH is raised above 8.0.

Sodium periodate can be used to oxidize the alcohol part of a sugar within a carbohydrate moiety attached to an antibody to an aldehyde. Each aldehyde group can be reacted with an amine, hydrazide, or hydrazine as described for carboxylic acids. Since the carbohydrate moiety is predominantly found on the crystallizable fragment region (Fc-region) of an antibody, conjugation can be achieved through site-directed modification of the carbohydrate away from the antigen-binding site. A Schiffs base intermediate is formed, which can be reduced to an alkyl amine through the reduction of the intermediate with sodium cyanoborohydride (mild and selective) or sodium borohydride (strong) water-soluble reducing agents.

The conjugation of a tracer and/or capture and/or detection antibody to its conjugation partner can be performed by different methods, such as chemical binding, or binding via a binding pair. The term "conjugation partner" as used herein denotes e.g. solid supports, polypeptides, detectable labels, members of specific binding pairs. In one embodiment, the conjugation of the capture and/or tracer and/or detection antibody to its conjugation partner is performed by chemically binding via N-terminal and/or ε-amino groups (lysine), ε-amino groups of different lysins, carboxy-, sulfhydryl-, hydroxyl-, and/or phenolic functional groups of the amino acid backbone of the antibody, and/or sugar alcohol groups of the carbohydrate structure of the antibody. In one embodiment, the capture antibody is conjugated to its conjugation partner via a binding pair. In one preferred embodiment, the capture antibody is conjugated to biotin and immobilization to a solid support is performed via solid support immobilized avidin or streptavidin. In one embodiment, the capture antibody is conjugated to its conjugation partner via a binding pair. In one preferred embodiment, the tracer antibody is conjugated to digoxygenin by a covalent bond as detectable label.

Chromogens (fluorescent or luminescent groups and dyes), enzymes, NMR-active groups or metal particles, haptens, e.g. digoxygenin, are examples of "detectable labels". The detectable label can also be a photoactivatable crosslinking group, e.g. an azido or an azirine group. Metal chelates, which can be detected by electrochemiluminescense, are also preferred signal-emitting groups, with particular preference being given to ruthenium chelates, e.g. a ruthenium (bispyridyl)32+chelate. Suitable ruthenium labeling groups are described, for example, in EP 0 580 979, WO 90/05301, WO 90/11511, and WO 92/14138. For direct detection, the labeling group can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay, e.g. EP-A-0 061 888), and radioisotopes.

Indirect detection systems comprise, for example, that the detection reagent, e.g., the detection antibody is labeled with a first partner of a binding pair. Examples of suitable binding pairs are antigen/antibody, biotin or biotin analogues such as aminobiotin, iminobiotin or desthiobiotin/avidin or Streptavidin, sugar/lectin, nucleic acid or nucleic acid analogue/complementary nucleic acid, and receptor/ligand, e.g., steroid hormone receptor/steroid hormone. In one preferred embodiment, the first binding pair members comprise hapten, antigen and hormone. In one preferred embodiment, the hapten is selected from the group consisting of digoxin, digoxygenin and biotin and analogues thereof. The second partner of such binding pair, e.g. an antibody, Streptavidin, etc., usually is labeled to allow for direct detection, e.g., by the labels as mentioned above.

Immunoassays can be performed generally in three different formats. One is with direct detection, one with indirect detection, or by a sandwich assay. The direct detection immunoassay uses a detection (or tracer) antibody that can be measured directly. An enzyme or other molecule allows for the generation of a signal that will produce a color, fluorescence, or luminescence that allow for the signal to be visualized or measured (radioisotopes can also be used, although it is not commonly used today). In an indirect assay a primary antibody that binds to the analyte is used to provide a defined target for a secondary antibody (tracer antibody) that specifically binds to the target provided by the primary antibody (referred to as detector or tracer antibody). The secondary antibody generates the measurable signal. The sandwich assay makes use of two antibodies, a capture and a tracer (detector) antibody. The capture antibody is used to bind (immobilize) analyte from solution or bind to it in solution. This allows the analyte to be specifically removed from the sample. The tracer (detector) antibody is used in a second step to generate a signal (either directly or indirectly as described above). The sandwich format requires two antibodies each with a distinct epitope on the target molecule. In addition, they must not interfere with one another, as both antibodies must be bound to the target at the same time.

Different principles for the determination of bispecific antibodies in an immunoassay are known to a person skilled in the art:

1) capture using
   one of the antigens;
   an anti-idiotypic antibody against one of the binding sites;
2) detection using
   the respective other antigen;
   an anti-idiotypic antibody against the respective other binding site;

These can be combined independently of each other.

Blood-Brain-Barrier Penetrating Antibodies of the Method According to the Invention The present invention relates in one aspect to the determination of the concentration of a bispecific antibody for use in the treatment of a disease in a patient in brain tissue,
   wherein the bispecific therapeutic antibody comprises
      i) an (effector function competent) Fc-region,
      ii) two binding sites specifically binding to a first (cell surface) target, and
      iii) one binding site specifically binding to a second (cell surface) target,
   wherein the treatment has reduced side effect after administration,
   wherein the side effect is one or more selected from the group consisting of vasodilation, bronchoconstriction, laryngeal edema, drop of cardiac pressure, and hypothermia.

In one embodiment, the two binding sites specifically binding to the first target and the binding site specifically binding to the second target are arranged in opposite directions, i.e. one is conjugated to the N-terminus of the Fc-region and the other is conjugated to the C-terminus of the Fc-region.

In one embodiment, the first (cell surface) target and the second (cell surface) target are different.

In one embodiment, the binding sites specifically binding to the first (cell surface) target and the binding site specifically binding to the second (cell surface) target are located at opposite ends (i.e. those specifically binding to the first target are both/each at an N-terminal end of a (full length) antibody heavy chain and that to the second target is at the C-terminal end of one of the (full length) antibody heavy chains of the bispecific antibody.

In one embodiment, the binding sites specifically binding to the first (cell surface) target and the binding site specifically binding to the second (cell surface) target are located at opposite ends of the bispecific antibody, i.e. one of the binding sites specifically binding to the first target is conjugated to the first N-terminus of the Fc-region and the other is conjugated to the second N-terminus of the Fc-region and the binding site that specifically binds to the second target is conjugated to one of the C-termini of the Fc-region.

In one embodiment, the binding site specifically binding to the second (cell surface) target is linked to one of the binding sites specifically binding to the first (cell surface) target by a peptidic linker. In one embodiment, the peptidic linker has the amino acid sequence of SEQ ID NO: 56 or 57.

In one embodiment, the binding site specifically binding to a second (cell surface) target is within the Fc-region, wherein at least one structural loop region of any of a CH2 domain, a CH3 domain, or a CH4 domain comprises at least one modification enabling the binding of said at least one modified loop region to the second (cell surface) target wherein the unmodified immunoglobulin constant domain does not bind to said target.

In one embodiment, the binding sites are pairs of an antibody heavy chain variable domain and an antibody light chain variable domain.

In one embodiment, the bispecific therapeutic antibody comprises
i) a pair of a first antibody light chain and a first antibody heavy chain,
ii) a pair of a second antibody light chain and a second antibody heavy chain, and
iii) an additional antibody fragment selected from the group consisting of scFv, Fab, scFab, dAb fragment, DutaFab and CrossFab,
wherein the pair of antibody chains of i) and ii) comprise the binding sites specifically binding to the first (cell surface) target and the additional antibody fragment of iii) comprises the binding site specifically binding to the second (cell surface) target.

In one embodiment, the additional antibody fragment of iii) is conjugated either directly or via a peptidic linker either to the first antibody heavy chain or to the second antibody heavy chain. In one embodiment, the additional antibody fragment of iii) is conjugated either directly or via a peptidic linker to the C-terminus of the antibody heavy chain of i) or ii). In one embodiment, the peptidic linker has the amino acid sequence of SEQ ID NO: 56 or 57. In one embodiment, the first antibody light chain and the second antibody light chain have the same amino acid sequence and the first antibody heavy chain and the second antibody heavy chain differ by mutations required for heterodimerization. In one embodiment, the mutations required for heterodimerization are the knobs-into-hole mutations. In one embodiment, the antibody heavy chain not conjugated to the additional antibody fragment of iii) does not comprise i) the C-terminal lysine residue or ii) the C-terminal glycine-lysine dipeptide.

In one embodiment, the first target is a brain target and the second target is the human transferrin receptor. In one embodiment, the first target is a brain target and the second target is the human transferrin receptor 1.

In one embodiment, the brain target is selected from the group consisting of beta-secretase 1 (BACE1), human amyloid beta (Abeta), epidermal growth factor receptor (EGFR), human epidermal growth factor receptor 2 (HER2), human Tau protein, phosphorylated human Tau protein, apolipoprotein E4 (ApoE4), human alpha-synuclein, human CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In one preferred embodiment, the brain target is selected from the group consisting of human CD20, human Tau protein, phosphorylated human Tau protein, human alpha-synuclein and human amyloid beta protein. In one preferred embodiment, the brain target is human amyloid beta protein. In one embodiment, the brain target is selected from SEQ ID NO: 58, 59, 60, 01, 61.

In one preferred embodiment, the bispecific therapeutic antibody comprises
i) a pair of a first antibody light chain and a first antibody heavy chain comprising a first light chain variable domain and a first heavy chain variable domain, which form a first binding site specifically binding to a brain target selected from the group consisting of human CD20, human Tau protein, phosphorylated human Tau protein, human alpha-synuclein and human amyloid beta protein,
ii) a pair of a second antibody light chain and a second antibody heavy chain comprising a second light chain variable domain and a second heavy chain variable domain, which form a second binding site specifically binding to the same brain target as the first binding site,
iii) an additional antibody fragment selected from the group consisting of scFv, Fab, scFab, dAb fragment, DutaFab and CrossFab, comprising a third light chain variable domain and a third heavy chain variable domain, which form a third binding site specifically binding to the human transferrin receptor (transferrin receptor 1), and
iv) a (human) effector function competent Fc-region (of the human IgG1 subclass),
wherein the additional antibody fragment of iii) is conjugated either directly or via a peptidic linker to the C-terminus of the antibody heavy chain of i) or ii).

In one embodiment, the additional antibody fragment is a Fab fragment, which specifically bind to a second antigen, and which is fused via a peptidic linker to the C-terminus of one of the heavy chains of i) or ii), wherein the constant domains CL and CH1 of the second light chain and the second heavy chain are replaced by each other, comprising a third light chain variable domain and a third heavy chain variable domain, which form a third binding site specifically binding to the human transferrin receptor (transferrin receptor 1).

In one embodiment, the binding site specifically binding to the human transferrin receptor (transferrin receptor 1) comprises (a) a HVR-H1 comprising the amino acid sequence of SEQ ID NO: 33 or 62; (b) a HVR-H2 comprising the amino acid sequence of SEQ ID NO: 34 or 63 or 35; (c) a HVR-H3 comprising the amino acid sequence of SEQ ID NO: 36, 37 or 64; (d) a HVR-L1 comprising the amino acid sequence of SEQ ID NO: 38 or 65; (e) a HVR-L2 comprising the amino acid sequence of SEQ ID NO: 39; and (f) a HVR-L3 comprising the amino acid sequence of SEQ ID NO: 66 or 40.

In one embodiment, the binding site specifically binding to the human transferrin receptor (transferrin receptor 1) comprises (a) a HVR-H1 comprising the amino acid sequence of SEQ ID NO: 33; (b) a HVR-H2 comprising the amino acid sequence of SEQ ID NO: 34; (c) a HVR-H3 comprising the amino acid sequence of SEQ ID NO: 37; (d) a HVR-L1 comprising the amino acid sequence of SEQ ID NO: 38; (e) a HVR-L2 comprising the amino acid sequence of SEQ ID NO: 39; and (f) a HVR-L3 comprising the amino acid sequence of SEQ ID NO: 40.

In one embodiment, the therapeutic antibody comprises one pair of a heavy chain variable domain of SEQ ID NO: 31 and a light chain variable domain of SEQ ID NO: 32 forming a binding site for the transferrin receptor (transferrin receptor 1) and at least one (i.e. one or two) pair of a heavy chain variable domain of SEQ ID NO: 19 and a light chain variable domain of SEQ ID NO: 20 (each) forming a binding site for human amyloid beta protein (Abeta).

In one embodiment, the therapeutic antibody comprises one pair of a heavy chain variable domain of SEQ ID NO: 31 and a light chain variable domain of SEQ ID NO: 32 forming the binding site for the human transferrin receptor (transferrin receptor 1) and two pairs of a heavy chain variable domain of SEQ ID NO: 41 and a light chain variable domain of SEQ ID NO: 42 each forming a binding site for human CD20. In one embodiment, the heavy chain variable region comprises a replacement of the amino acid residue at Kabat position 11 with any amino acid but leucine. In one embodiment, the substitution comprises a replacement of the amino acid residue at Kabat position 11 with a nonpolar amino acid. In one preferred embodiment, the substitution comprises a replacement of the amino acid residue at Kabat position 11 in the heavy chain variable domain of SEQ ID NO: 41 with an amino acid residue selected from the group consisting of valine, leucine, isoleucine, serine, and phenylalanine.

In one embodiment, the therapeutic antibody comprises one pair of a heavy chain variable domain of SEQ ID NO: 31 and a light chain variable domain of SEQ ID NO: 32 forming the binding site for the human transferrin receptor (transferrin receptor 1) and two pairs of a heavy chain variable domain of SEQ ID NO: 43 and a light chain variable domain of SEQ ID NO: 44 each forming a binding site for human alpha-synuclein.

In one embodiment, the therapeutic antibody comprises one pair of a heavy chain variable domain of SEQ ID NO: 31 and a light chain variable domain of SEQ ID NO: 32 forming the binding site for the human transferrin receptor (transferrin receptor 1) and two pairs of a humanized heavy chain variable domain derived from SEQ ID NO: 45 and a humanized light chain variable domain derived from SEQ ID NO: 46 each forming a binding site for human alpha-synuclein.

In one embodiment, the therapeutic antibody comprises one pair of a heavy chain variable domain of SEQ ID NO: 31 and a light chain variable domain of SEQ ID NO: 32 forming the binding site for the human transferrin receptor and two pairs of a humanized heavy chain variable domain derived from SEQ ID NO: 47 and a humanized light chain variable domain derived from SEQ ID NO: 48 each forming a binding site for human alpha-synuclein.

In one embodiment, the therapeutic antibody comprises one pair of a heavy chain variable domain of SEQ ID NO: 31 and a light chain variable domain of SEQ ID NO: 32 forming the binding site for the human transferrin receptor (transferrin receptor 1) and two pairs of a humanized heavy chain variable domain derived from SEQ ID NO: 49 and a humanized light chain variable domain derived from SEQ ID NO: 50 each forming a binding site for human alpha-synuclein.

In one embodiment, the therapeutic antibody comprises one pair of a heavy chain variable domain of SEQ ID NO: 31 and a light chain variable domain of SEQ ID NO: 32 forming the binding site for the human transferrin receptor (transferrin receptor 1) and two pairs of a humanized heavy chain variable domain derived from SEQ ID NO: 51 and a humanized light chain variable domain derived from SEQ ID NO: 52 each forming a binding site for human alpha-synuclein.

In one embodiment, the therapeutic antibody comprising one pair of a heavy chain variable domain of SEQ ID NO: 31 and a light chain variable domain of SEQ ID NO: 32 forming the binding site for the human transferrin receptor (transferrin receptor 1) and two pairs of a humanized heavy chain variable domain derived from SEQ ID NO: 53 and a humanized light chain variable domain derived from SEQ ID NO: 54 each forming a binding site for human alpha-synuclein.

In one embodiment, the disease is a neurological disorder. In one embodiment, the disease is selected from the group of neurological disorders consisting of neuropathy, amyloidosis, cancer, an ocular disease or disorder, viral or microbial infection, inflammation, ischemia, neurodegenerative disease, seizure, behavioral disorders, lysosomal storage disease, Lewy body disease, post poliomyelitis syndrome, Shy-Draeger syndrome, olivopontocerebellar atrophy, Parkinson's disease, multiple system atrophy, striatonigral degeneration, tauopathies, Alzheimer disease, supranuclear palsy, prion disease, bovine spongiform encephalopathy, scrapie, Creutzfeldt-Jakob syndrome, kuru, Gerstmann-Straussler-Scheinker disease, chronic wasting disease, and fatal familial insomnia, bulbar palsy, motor neuron disease, nervous system heterodegenerative disorder, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, Unverricht-Lundborg syndrome, dementia, Pick's disease, spinocerebellar ataxia, cancer of the CNS and/or brain, including brain metastases resulting from cancer elsewhere in the body. In one embodiment, the disease is selected from the group of neurological disorders consisting of Alzheimer's disease, Parkinson's disease, cancer of the CNS and/or brain, including brain metastases resulting from cancer elsewhere in the body, and tauopathies. In one embodiment, the disease is selected from the group of neurological disorders consisting of Alzheimer's disease, Parkinson's disease and tauopathies.

In one embodiment, the therapeutic antibody comprises an effector function competent Fc-region. In one embodiment, the effector function competent Fc-region is an Fc-region that specifically binds to/can be specifically bound by human FcγR. In one embodiment, the effector function competent Fc-region can elicit ADCC.

In one embodiment, ADCC elicited (upon injection/while binding to the second (cell surface) target) by the bispecific therapeutic antibody is lower than that elicited by a bivalent bispecific antibody that has only one, i.e. exactly one, binding site that specifically bind to the first (cell surface) target and (exactly) one binding site that specifically binds to the second (cell surface) target, i.e. one of the binding sites specifically binding to the first (cell surface) target is deleted. In one embodiment, the ADCC is 10-fold or more lower.

In one embodiment, the administration is an intravenous, subcutaneous, or intramuscular administration.

In one embodiment, the first antibody heavy chain (of i)) and the second antibody heavy chain (of ii)) form a heterodimer. In one embodiment, the first antibody heavy chain and the second antibody heavy chain comprise mutations supporting the formation of a heterodimer.

In one embodiment,
a) the antibody heavy chains are full-length antibody heavy chains of the human subclass IgG1,
b) the antibody heavy chains are full-length antibody heavy chains of the human subclass IgG4,
c) one of the antibody heavy chains is a full length antibody heavy chain of the human subclass IgG1 with the mutations T366W and optionally S354C or Y349C and the other antibody heavy chain is a full length antibody heavy chain of the human subclass IgG1 with the mutations T366S, L368A, Y407V and optionally Y349C or S354C,
d) both antibody heavy chains are full length antibody heavy chains of the human subclass IgG1 with the mutations I253A, H310A and H435A and the mutations T366W and optionally S354C or Y349C in one of the antibody heavy chains and the mutations T366S, L368A, Y407V and optionally Y349C or S354C in the respective other antibody heavy chain,
e) both antibody heavy chains are full length antibody heavy chains of the human subclass IgG1 with the mutations M252Y, S254T and T256E and the mutations T366W and optionally S354C or Y349C in one of the antibody heavy chains and the mutations T366S, L368A, Y407V and optionally Y349C or S354C in the respective other antibody heavy chain, or
f) both antibody heavy chains are antibody heavy chains of the human subclass IgG1 with the mutations T307H and N434H and the mutations T366W and optionally S354C or Y349C in one of the antibody heavy chains and the mutations T366S, L368A, Y407V and optionally Y349C or S354C in the respective other antibody heavy chain.

In one embodiment,
a) the antibody heavy chains are antibody heavy chains of the human subclass IgG1,
b) the antibody heavy chains are antibody heavy chains of the human subclass IgG4,
c) one of the antibody heavy chains is an antibody heavy chain of the human subclass IgG1 with the mutations T366W and optionally S354C or Y349C and the other antibody heavy chain is an antibody heavy chain of the human subclass IgG1 with the mutations T366S, L368A, Y407V and optionally Y349C or S354C,
d) both antibody heavy chains are antibody heavy chains of the human subclass IgG1 with the mutations I253A, H310A and H435A and the mutations T366W and optionally S354C or Y349C in one of the antibody heavy chains and the mutations T366S, L368A, Y407V and optionally Y349C or S354C in the respective other antibody heavy chain,
e) both antibody heavy chains are antibody heavy chains of the human subclass IgG1 with the mutations M252Y, S254T and T256E and the mutations T366W and optionally S354C or Y349C in one of the antibody heavy chains and the mutations T366S, L368A, Y407V and optionally Y349C or S354C in the respective other antibody heavy chain, or
f) both antibody heavy chains are antibody heavy chains of the human subclass IgG1 with the mutations T307H and N434H and the mutations T366W and optionally S354C or Y349C in one of the antibody heavy chains and the mutations T366S, L368A, Y407V and optionally Y349C or S354C in the respective other antibody heavy chain,
wherein the C-terminal lysine or glycine-lysine dipeptide is present or absent.

Embodiments of the Methods According to the Invention

The relation between CSF, blood-brain-barrier and blood has been reviewed by Katsinelos, T., et al. (Front. Immunol. 10 (2019) 1139) as follows:

IgG levels are maintained in human serum at around 10 mg/ml. The brain is isolated from serum by the blood-brain barrier (BBB), which is impermeable to large macromolecules including IgG (Neuwelt, E. A., et al., Nat. Rev. Neurosci. 12 (2011) 169-182). The brain, instead, is bathed in cerebrospinal fluid (CSF), which is produced following the filtration of blood and transport of ions across the choroid plexus. The resulting concentration of IgG in CSF is around 500- to 1,000-fold lower than in serum. At face value, this low concentration of antibody in the brain makes CNS antigens unattractive as targets for passive immunotherapy, which is normally administered to the periphery. This is compounded by a poor understanding of the mechanisms by which steady state levels of antibody are maintained. CSF flows around the brain, before exiting the CNS along spinal and cranial nerves and via drainage to the lymphatic system (Louveau, A., et al., Nature 523 (2015) 337-341; Aspelund, A., J. Exp. Med. 212 (2015) 991-999). Intrathecally administered IgG is rapidly cleared from the brain, largely through this bulk flow and with a possible contribution of selective transport out of the brain. The neonatal Fc receptor, FcRn, is expressed in abundance at the BBB (Schlachetzki, F., et al., J. Neurochem. 81 (2002) 203-206). Given FcRn's role in transcytosis of antibodies across the placenta, it has been suggested that FcRn may perform reverse transcytosis to help maintain the low IgG environment of the CNS. There is some evidence that antibody clearance from the brain is mediated in part by the antibody Fc domain (Zhang, Y. and Pardridge, W. M., J. Neuroimmunol. 114 (2001) 168-172; Cooper, P. R., et al., Brain Res. 1534 (2013) 13-21), and export of an anti-AD monoclonal antibody was reduced in an FcRn-deficient mouse (Deane, R., et al., J. Neurosci. 25 (2005) 11495-11503). However, the brain concentration of peripherally administered IgG was not significantly different between wild-type mice and mice lacking FcRn (Abuqayyas, L. and Balthasar, J. P., Mol. Pharma. 10 (2013) 1505-1513).

For small experimental animals, the blood is removed from the brain prior to sampling by perfusion. For example, mice can be transcardially perfused with ice-cold PBS at a rate of 2 ml/min for 8 min. and brains are subsequently harvested.

Methods to transport therapeutic antibodies across the blood brain barrier, using multispecific antibodies, for example, bispecific or trispecific antibodies, comprising one or more than one carrier molecule, and one or more than one cargo molecule, via a receptor-mediate transcytosis pathway are currently explored. For example, a transferrin receptor (TfR)-binding antibody (and variants thereof) may be used as the carrier, and when fused to a cargo molecule produces a bispecific antibody that is able to cross the blood brain barrier (see for example Zuchero, Y. J, Y., et. al., Neuron 89 (12016) 70-82; Bien-Ly, N., et. al. J. Exp. Med. 211 (2014) 233-244; US 2018/8002433; CA 3,000,560; which are incorporated herein by reference). Alternatively, an insulin-like growth factor 1 receptor (IGF-1R)-binding antibody may be used as a carrier, and fused to the cargo molecule, to produce a bispecific antibody that crosses the blood brain barrier (see for example WO 2015/131256; WO 2015/131257; WO 2015/131258; which are incorporated herein by reference).

For a robust and correct determination of the amount in brain, lysates of a therapeutic antibody transported across the blood-brain-barrier into the brain the interference from residual blood in the sample has to be excluded. As outlined above the resulting concentration of IgG in CSF is around 500- to 1,000-fold lower than in serum and the brain is spanned by an interwoven net of blood vessels. Thus, the chance of residual blood in brain tissue sample is not neglectable. Furthermore, even minor amounts of residual blood can severely interfere with the quantitative determination of antibody in brain tissue.

Thus, a correction, i.e. reduction, with the amount of therapeutic antibody in residual blood in the brain lysate sample has to be made.

Thus, the use of a quantitative blood correction marker that does not significantly diffuse during the perfusion phase into the brain is required. However, if these are determined at steady state, a small, constant concentration will exist behind the BBB.

The current invention is based, at least in part, on the finding that the amount of residual blood in a brain lysate can be determined by applying a correction antibody shortly before the brain sample is taken. It has been found that it is especially advantageous to use as reference antibody an antibody that is not specifically binding to any target in the experimental animal from which the brain sample is obtained, most preferably a human germline antibody.

Thus, herein is reported a method for the determination of the amount of a therapeutic antibody, which has been transported across the blood-brain-barrier from the blood into the brain of an experimental animal. The amount is preferably determined in a brain lysate sample. The gist of the invention lies in the additional application of an inert antibody, which is not transported across the blood-brain-barrier, shortly before obtaining the brain sample in which the amount of the therapeutic antibody transported across the blood-brain-barrier has to be determined. By applying the inert antibody, a correction value for the amount of therapeutic antibody present in residual blood in the brain sample is obtained. This residual blood-derived amount is used to correct the determined amount for non-brain-located antibody. A determination without correction would determine the total amount of therapeutic antibody in the sample, i.e. the amount transported across the blood-brain-barrier into the brain and the amount in residual blood in the sample. The amount of therapeutic antibody in residual blood is not neglectable, as only about 0.1% of the antibody in the blood will pass the blood-brain-barrier. Thus, the concentration of the therapeutic antibody in the blood exceeds the concentration of the therapeutic antibody in the brain by at least two and up to three orders of magnitude. Thereby the results obtained are too high if not corrected with a method according to the current invention.

This is especially important for the comparator IgG or brain shuttles with clearance approaching that of an IgG, because slowly clearing molecules maintain a high concentration in the blood, and if the amount is comparatively very small in the brain, then a small amount of blood contamination can overwhelm the determination of brain concentrations.

The method according to the current invention can be applied to any brain tissue sample independently of the method used for removing blood therefrom.

The method according to the invention has a cross-species assay availability, sufficient assay-robustness, -precision and -accuracy and a broad sensitivity range.

In a nutshell, the current invention provides a method for determining residual blood in a brain sample of an experimental animal, wherein just prior to perfusion, i.e. at most 5 min. before, a second inert IgG is administered, a plasma sample is taken, perfusion is conducted, brain and plasma concentrations are measured and corrected wherein the advantage is that the amount that transits the blood-brain-barrier is limited; thereby, the concentration of the second inert antibody reflects only plasma volume wherein a first specific assay for the therapeutic antibody and a second specific assay for the second inert antibody is employed wherein issues with anti-therapeutic antibody antibody positive animals, which may confound the measurement, could be prevented.

FIG. 1 provides an exemplary calculation exploiting the use of an inter antibody to determine blood contamination in a (brain) tissue sample.

For example, using a conventional ELISA the concentration of the therapeutic monoclonal antibody (tmAb) and the inert reference monoclonal antibody (refmAb) is determined in the blood plasma as well as in the homogenized brain tissue sample.

The result of an ELISA is normally obtained as a mass concentration with the SI unit [g/L]. In a first step each of the mass concentrations determined for the tmAb and the refmAb, respectively, is converted into a mass fraction with the unit [g/g] by dividing the determined mass concentration by the brain tissue concentration of the sample. In the second step the amount of residual plasma in the brain tissue sample, i.e. the plasma-contamination, is calculated by dividing the mass fraction of the inert antibody obtained in the first step by the determined plasma concentration of the refmAb. Thereby the volume of residual plasma per weight of brain sample is obtained. In a third step the mass fraction of tmAb in the brain tissue sample originating from plasma contamination is calculated by multiplying the plasma concentration of the tmAb with the volume of residual plasma per weight of brain sample. In the fourth and final step, the true brain concentration of the tmAb is obtained by subtracting the mass fraction of tmAb in the brain tissue sample originating from plasma contamination obtained in the third step from the mass fraction determined for the tmAb in the first step.

The method according to the invention has been applied to the analysis of two bispecific antibodies, binding to TfR and a therapeutic target 1 or 2, respectively, in cynomolgus monkey brain lysates. The respective structure of the antibodies is shown in FIG. 2. The detection assays for the therapeutic antibody and the reference antibody, respectively, are shown in FIG. 3.

As outlined in Example 1 the assay for the determination of the inert antibody has sensitivity of 8 ng/ml, i.e. about 1.1-1.5 µL blood plasma/g cynomolgus brain can be detected (this corresponds to about 2.2-3 µL blood/g cynomolgus brain).

Five different brain regions have been analyzed: Cerebellum, Hippocampus, Statium, Cortex and Choroid plexus.

Four different animals have been analyzed, whereof animal 1 to 3 contained no residual blood in the brain samples but animal 4 did as determined by photo analysis (data not shown).

With the method according to the current invention, this contamination could be detected and, thus, the respective values could be corrected accordingly.

| animal | time | Sample tissue | DP47GS PGLALA [ng/mL] MW | plasma concentration [µL plasma/g brain] | blood contamination [µL blood/g brain] | DP47GS PGLALA [µg/mL] in CPP |
|---|---|---|---|---|---|---|
| 1 | 336 h | Cerebellum | BLQ | | | 25 |
| | | Hippocampus | BLQ | | | |
| | | Striatum | BLQ | | | |
| | | Cortex | BLQ | | | |
| | | Choroid plexus | BLQ | | | |
| 2 | 336 h | Cerebellum | BLQ | | | 23 |
| | | Hippocampus | BLQ | | | |
| | | Striatum | BLQ | | | |
| | | Cortex | BLQ | | | |
| | | Choroid plexus | BLQ | | | |
| 3 | 336 h | Cerebellum | BLQ | | | 33 |
| | | Hippocampus | BLQ | | | |
| | | Striatum | BLQ | | | |
| | | Cortex | BLQ | | | |
| | | Choroid plexus | BLQ | | | |
| 4 | 336 h | Cerebellum | 18 | 1.6 | 3 | 27 |
| | | Hippocampus | BLQ | | | |
| | | Striatum | 9 | 1.3 | 3 | |
| | | Cortex | 17 | 2.1 | 4 | |
| | | Choroid plexus | BLQ | | | |

| | | determined concentration | | | | | | |
|---|---|---|---|---|---|---|---|---|
| | | plasma | | brain [ng/g] | | | | Choroid |
| animal | | [ng/mL] | [ng/µL] | Cerebellum | Hippocampus | Striatum | Cortex | plexus |
| 1 | antibody_1 | 35 | 0.034741 | 10.9 | 50.5 | 21.0 | 13.4 | 334 |
| 2 | antibody_1 | 184 | 0.184316 | 21.5 | 47.5 | 28.7 | 21.8 | 744 |
| 3 | antibody_1 | 20 | 0.019709 | 17.3 | 46.1 | 24.4 | 24.6 | 747 |
| 4 | antibody_1 | 101 | 0.101429 | 17.5 | 45.1 | 28.2 | 25.1 | 385 |
| | brain tissue concentration [g/mL]-> | | | 0.422 | 0.164 | 0.262 | 0.295 | 0.019 |
| | corrected brain concentration [ng/g]-> | | | 17.3 | | 27.9 | 24.9 | |

| | | plasma | | brain [ng/mL] | | | | Choroid |
|---|---|---|---|---|---|---|---|---|
| | | [ng/mL] | [ng/µL] | Cerebellum | Hippocampus | Striatum | Cortex | plexus |
| 1 | inert reference antibody | 25107 | 25.107 | BLQ | BLQ | BLQ | BLQ | BLQ |
| 2 | inert reference antibody | 25807 | 25.807 | BLQ | BLQ | BLQ | BLQ | BLQ |
| 3 | inert reference antibody | 33193 | 33.193 | BLQ | BLQ | BLQ | BLQ | BLQ |
| 4 | inert reference antibody | 27212 | 27.212 | 18 | BLQ | 9 | 17 | BLQ |

In a further study fifteen animals have been does with an anti-Abeta antibody at 20 mg/kg and fifteen animals have been does with 10 mg/kg of an anti-Abeta/TfR antibody. After different time points after administration, the respective samples have been analyzed. In all sample residual blood has been detected in the respective brain tissue samples. Thus, also in these cases corrected values were obtained with the method according to the current invention.

| analyte | time after application | animal | Sample tissue | antibody ng/g tissue | plasma µl/g tissue |
|---|---|---|---|---|---|
| Anti-Abeta antibody | 4 h | 29211 | Brain (Cerebellum) | 22 | 1.0 |
| | | | Brain (Hippocampus) | 21 | 0.9 |
| | | | Brain (Striatum) | 20 | 0.9 |
| | | | Brain (Cortex) | 26 | 1.2 |
| Anti-Abeta antibody | 4 h | 29213 | Brain (Cerebellum) | 16 | 0.6 |
| | | | Brain (Hippocampus) | 20 | 0.7 |
| | | | Brain (Striatum) | 13 | 0.5 |
| | | | Brain (Cortex) | 15 | 0.6 |
| | | | Brain (Choroid plexus) | 822 | 29.6 |
| Anti-Abeta antibody | 4 h | 29214 | Brain (Cerebellum) | 31 | 1.2 |
| | | | Brain (Hippocampus) | 38 | 1.4 |
| | | | Brain (Striatum) | 21 | 0.8 |
| | | | Brain (Cortex) | 25 | 1.0 |
| | | | Brain (Choroid plexus) | 569 | 21.7 |
| Anti-Abeta antibody | 24 h | 29328 | Brain (Cerebellum) | 53 | 3.7 |
| | | | Brain (Hippocampus) | 31 | 2.1 |
| | | | Brain (Striatum) | 22 | 1.5 |
| | | | Brain (Cortex) | 13 | 0.9 |
| | | | Brain (Choroid plexus) | 925 | 63.8 |
| Anti-Abeta antibody | 24 h | 29329 | Brain (Cerebellum) | 22 | 1.1 |
| | | | Brain (Hippocampus) | 22 | 1.0 |
| | | | Brain (Striatum) | 21 | 1.0 |
| | | | Brain (Cortex) | 23 | 1.1 |
| | | | Brain (Choroid plexus) | 925 | 43.6 |
| Anti-Abeta antibody | 24 h | 29330 | Brain (Cerebellum) | 18 | 0.9 |
| | | | Brain (Hippocampus) | 25 | 1.3 |
| | | | Brain (Striatum) | 25 | 1.2 |
| | | | Brain (Cortex) | 28 | 1.4 |
| | | | Brain (Choroid plexus) | 493 | 25.0 |
| Anti-Abeta antibody | 96 h | 29208 | Brain (Cerebellum) | 29 | 1.1 |
| | | | Brain (Hippocampus) | 32 | 1.2 |
| | | | Brain (Striatum) | 32 | 1.2 |
| | | | Brain (Cortex) | 35 | 1.3 |
| | | | Brain (Choroid plexus) | 411 | 15.0 |
| Anti-Abeta antibody | 96 h | 29217 | Brain (Cerebellum) | 19 | 0.6 |
| | | | Brain (Hippocampus) | 42 | 1.3 |
| | | | Brain (Striatum) | 22 | 0.7 |
| | | | Brain (Cortex) | 23 | 0.7 |
| | | | Brain (Choroid plexus) | 925 | 28.8 |
| Anti-Abeta antibody | 96 h | 29219 | Brain (Cerebellum) | 21 | 0.6 |
| | | | Brain (Hippocampus) | 21 | 0.6 |
| | | | Brain (Striatum) | 16 | 0.5 |
| | | | Brain (Cortex) | 28 | 0.8 |
| | | | Brain (Choroid plexus) | 529 | 15.7 |
| Anti-Abeta antibody | 168 h | 29114 | Brain (Cerebellum) | 33 | 1.1 |
| | | | Brain (Hippocampus) | 23 | 0.7 |
| | | | Brain (Striatum) | 32 | 1.0 |
| | | | Brain (Cortex) | 22 | 0.7 |
| | | | Brain (Choroid plexus) | 493 | 15.9 |
| Anti-Abeta antibody | 168 h | 29119 | Brain (Cerebellum) | 20 | 1.1 |
| | | | Brain (Hippocampus) | 19 | 1.0 |
| | | | Brain (Striatum) | 26 | 1.4 |
| | | | Brain (Cortex) | 28 | 1.5 |
| | | | Brain (Choroid plexus) | 569 | 30.7 |
| Anti-Abeta antibody | 168 h | 29122 | Brain (Cerebellum) | 24 | 1.1 |
| | | | Brain (Hippocampus) | 18 | 0.8 |
| | | | Brain (Striatum) | 26 | 1.2 |
| | | | Brain (Cortex) | 21 | 1.0 |
| | | | Brain (Choroid plexus) | 925 | 42.3 |
| Anti-Abeta antibody | 336 h | 29140 | Brain (Cerebellum) | 34 | 1.5 |
| | | | Brain (Hippocampus) | 20 | 0.9 |
| | | | Brain (Striatum) | 37 | 1.7 |
| | | | Brain (Cortex) | 54 | 2.5 |
| | | | Brain (Choroid plexus) | 569 | 25.7 |
| Anti-Abeta antibody | 336 h | 29191 | Brain (Cerebellum) | 22 | 0.8 |
| | | | Brain (Hippocampus) | 23 | 0.9 |
| | | | Brain (Striatum) | 21 | 0.8 |
| | | | Brain (Cortex) | 22 | 0.8 |
| | | | Brain (Choroid plexus) | 925 | 34.7 |
| Anti-Abeta antibody | 336 h | 29194 | Brain (Cerebellum) | 59 | 2.9 |
| | | | Brain (Hippocampus) | 22 | 1.1 |

| analyte | time after application | animal | Sample tissue | antibody ng/g tissue | plasma µl/g tissue |
|---|---|---|---|---|---|
| | | | Brain (Striatum) | 16 | 0.8 |
| | | | Brain (Cortex) | 33 | 1.6 |
| | | | Brain (Choroid plexus) | 740 | 36.2 |
| Anti-Abeta/TfR antibody | 4 h | 29317 | Brain (Cerebellum) | 22 | 0.8 |
| | | | Brain (Hippocampus) | 32 | 1.2 |
| | | | Brain (Striatum) | 20 | 0.8 |
| | | | Brain (Cortex) | 23 | 0.9 |
| | | | Brain (Choroid plexus) | 206 | 7.9 |
| Anti-Abeta/TfR antibody | 4 h | 29319 | Brain (Cerebellum) | 13 | 0.6 |
| | | | Brain (Hippocampus) | 23 | 1.1 |
| | | | Brain (Striatum) | 28 | 1.3 |
| | | | Brain (Cortex) | 13 | 0.6 |
| | | | Brain (Choroid plexus) | 673 | 30.8 |
| Anti-Abeta/TfR antibody | 4 h | 29331 | Brain (Cerebellum) | 44 | 1.6 |
| | | | Brain (Hippocampus) | 22 | 0.8 |
| | | | Brain (Striatum) | 14 | 0.5 |
| | | | Brain (Cortex) | 19 | 0.7 |
| | | | Brain (Choroid plexus) | 617 | 21.6 |
| Anti-Abeta/TfR antibody | 24 h | 29197 | Brain (Cerebellum) | 32 | 1.2 |
| | | | Brain (Hippocampus) | 23 | 0.9 |
| | | | Brain (Striatum) | 69 | 2.7 |
| | | | Brain (Cortex) | 22 | 0.8 |
| | | | Brain (Choroid plexus) | 308 | 11.9 |
| Anti-Abeta/TfR antibody | 24 h | 29199 | Brain (Cerebellum) | 21 | 0.7 |
| | | | Brain (Hippocampus) | 20 | 0.6 |
| | | | Brain (Striatum) | 16 | 0.5 |
| | | | Brain (Cortex) | 19 | 0.6 |
| | | | Brain (Choroid plexus) | 296 | 9.6 |
| Anti-Abeta/TfR antibody | 24 h | 29201 | Brain (Cerebellum) | 21 | 0.6 |
| | | | Brain (Hippocampus) | 19 | 0.6 |
| | | | Brain (Striatum) | 18 | 0.6 |
| | | | Brain (Cortex) | 17 | 0.5 |
| | | | Brain (Choroid plexus) | 389 | 11.7 |
| Anti-Abeta/TfR antibody | 96 h | 29207 | Brain (Cerebellum) | 16 | 0.6 |
| | | | Brain (Hippocampus) | 21 | 0.8 |
| | | | Brain (Striatum) | 25 | 0.9 |
| | | | Brain (Cortex) | 30 | 1.1 |
| | | | Brain (Choroid plexus) | 389 | 14.3 |
| Anti-Abeta/TfR antibody | 96 h | 29218 | Brain (Cerebellum) | 26 | 1.0 |
| | | | Brain (Hippocampus) | 24 | 0.9 |
| | | | Brain (Striatum) | 16 | 0.6 |
| | | | Brain (Cortex) | 23 | 0.9 |
| | | | Brain (Choroid plexus) | 822 | 32.1 |
| Anti-Abeta/TfR antibody | 96 h | 29220 | Brain (Cerebellum) | 17 | 0.7 |
| | | | Brain (Hippocampus) | 15 | 0.6 |
| | | | Brain (Striatum) | 21 | 0.9 |
| | | | Brain (Cortex) | 17 | 0.7 |
| | | | Brain (Choroid plexus) | 389 | 16.3 |
| Anti-Abeta/TfR antibody | 168 h | 29118 | Brain (Cerebellum) | 17 | 0.6 |
| | | | Brain (Hippocampus) | 19 | 0.7 |
| | | | Brain (Striatum) | 19 | 0.7 |
| | | | Brain (Cortex) | 20 | 0.7 |
| | | | Brain (Choroid plexus) | 493 | 18.4 |
| Anti-Abeta/TfR antibody | 168 h | 29141 | Brain (Cerebellum) | 21 | 1.0 |
| | | | Brain (Hippocampus) | 32 | 1.6 |
| | | | Brain (Striatum) | 45 | 2.2 |
| | | | Brain (Cortex) | 20 | 1.0 |
| | | | Brain (Choroid plexus) | 1057 | 51.9 |
| Anti-Abeta/TfR antibody | 168 h | 29157 | Brain (Cerebellum) | 24 | 0.7 |
| | | | Brain (Hippocampus) | 24 | 0.6 |
| | | | Brain (Striatum) | 50 | 1.4 |
| | | | Brain (Cortex) | 18 | 0.5 |
| | | | Brain (Choroid plexus) | 1057 | 28.8 |
| Anti-Abeta/TfR antibody | 240 h | 28640 | Brain (Cerebellum) | 29 | 1.4 |
| | | | Brain (Hippocampus) | 22 | 1.0 |
| | | | Brain (Striatum) | 20 | 0.9 |
| | | | Brain (Cortex) | 19 | 0.9 |
| | | | Brain (Choroid plexus) | 1057 | 49.9 |
| Anti-Abeta/TfR antibody | 240 h | 28641 | Brain (Cerebellum) | 14 | 0.4 |
| | | | Brain (Hippocampus) | 16 | 0.5 |
| | | | Brain (Striatum) | 26 | 0.8 |
| | | | Brain (Cortex) | 19 | 0.6 |
| | | | Brain (Choroid plexus) | 463 | 14.5 |
| Anti-Abeta/TfR antibody | 240 h | 29139 | Brain (Cerebellum) | 21 | 0.9 |
| | | | Brain (Hippocampus) | 17 | 0.7 |

-continued

| analyte | time after application | animal | Sample tissue | antibody ng/g tissue | plasma µl/g tissue |
|---|---|---|---|---|---|
| | | | Brain (Striatum) | 22 | 0.9 |
| | | | Brain (Cortex) | 12 | 0.5 |
| | | | Brain (Choroid plexus) | 218 | 9.4 |

To show the general applicability of the method according to the current invention the same analysis has been done with a second antibody, an anti-TfR/target_2 antibody, in C57BL/6 wild-type mice.

An overlay of the calibration curves of the detection assay of the inert reference antibody in the presence of 1% cynomolgus brain lysate (CBL; cynoBL) and 1% mouse brain lysate (MBL; muBL) is shown in FIG. 4. It can be seen that the origin of the matrix does not influence the assay.

The working range for the assay in the presence of 1% MBL is 8.4 ng/mL to 250 ng/mL. Up to 10 µg/mL of therapeutic antibody can be present in the assay without interference in the presence of 1% MBL.

The working range for the assay in the presence of 1% mouse pooled plasma (MPP) is 11 ng/mL to 220 ng/mL. Up to 20 µg/mL of therapeutic antibody can be present in the assay without interference in the presence of 1% MPP.

A single dose of 20 mg/ml of the antibody was applied and sample were analyzed 24 h, 48 h, 96 h, 168 h, 336 h, 504 h and 672 h after application. The respective concentrations in brain lysate and plasma have been determined. In FIG. 5, the determined concentrations of the applied antibody in brain lysate are shown as ratio of uncorrected vs. corrected brain concentration. That is, if the correction does not influence the value then the ratio is 1. If due to the correction by the residual plasma value the determined concentration of the second antibody has been reduced the value will become smaller than 1. This difference increases by time as more antibody is transported across the blood-brain-barrier. It can be seen from FIG. 5 that the ratio becomes smaller and smaller by time. Thereby it can be seen that the correction done according to the method according to the current invention eliminated interference from residual blood in the brain samples. The respective assay used for the determination of the second antibody is shown in FIG. 6.

Inert Reference Monoclonal Antibody of the Method According to the Invention

An inert reference monoclonal antibody useful in the method according to the current invention is preferably a human immunoglobulin molecule, especially a human immunoglobulin molecule that is not capable of specific binding to an antigen.

An exemplary inert reference monoclonal antibody is the antibody DP47GS. DP47GS comprises a heavy chain variable region sequence based on the human VH3-23 germline sequence and a light chain variable region sequence based on the human Vk3-20 germline sequence.

In one embodiment, said inert reference monoclonal antibody is an IgG-class immunoglobulin molecule, particularly an IgG1-subclass immunoglobulin molecule. In one embodiment, said inert reference monoclonal antibody is a human immunoglobulin molecule. In one embodiment, said inert reference monoclonal antibody is a monoclonal antibody. In one embodiment, said inert reference monoclonal antibody is not capable of specific binding to an antigen. In one embodiment, said inert reference monoclonal antibody comprises a heavy chain variable region sequence based on the human VH3-23 germline sequence. In a specific embodiment, said inert reference monoclonal antibody comprises the heavy chain variable region sequence of SEQ ID NO: 67. In one embodiment, said inert reference monoclonal antibody comprises a light chain variable region sequence based on the human Vk3-20 germline sequence. In a specific embodiment, said inert reference monoclonal antibody comprises the light chain variable region sequence of SEQ ID NO: 68. In an even more specific embodiment, said inert reference monoclonal antibody comprises the heavy chain variable region sequence of SEQ ID NO: 67 and the light chain variable region sequence of SEQ ID NO: 68. In one embodiment, said inert reference monoclonal antibody is not capable of specific binding to an antigen, and comprises a heavy chain variable region sequence based on the human VH3-23 germline sequence and a light chain variable region sequence based on the human Vk3-20 germline sequence.

In one embodiment, said inert reference monoclonal antibody comprises a heavy chain variable region sequence based on the human VH3-23 germline sequence. In a specific embodiment, said inert reference monoclonal antibody comprises a heavy chain variable region sequence that is at least 95%, 96%, 97%, 98%, 99% or 100% identical to the sequence of SEQ ID NO: 67. In one embodiment, said inert reference monoclonal antibody comprises a light chain variable region sequence based on the human Vk3-20 germline sequence. In a specific embodiment, said inert reference monoclonal antibody comprises a light chain variable region sequence that is at least 95%, 96%, 97%, 98%, 99% or 100% identical to the sequence of SEQ ID NO: 68. In an even more specific embodiment, said inert reference monoclonal antibody comprises the heavy chain variable region sequence of SEQ ID NO: 67 and the light chain variable region sequence of SEQ ID NO: 68. Immunoglobulin molecules comprising these variable region sequences are not capable of specific binding to an antigen, particularly a human antigen. They lack binding to normal tissues as well as PBMCs, have no polyreactivity and show no non-specific accumulation in vivo by imaging (data not shown). The variable region sequences are entirely based on human germline sequences, with the exception of the heavy chain CDR 3 wherein a GSG sequence has been introduced to generate a non-binding immunoglobulin.

In one embodiment, said inert reference monoclonal antibody comprises a heavy chain with a variable domain with the amino acid sequence of SEQ ID NO: 67 and a human IgG1 constant region and a light chain with a variable domain with the amino acid sequence of SEQ ID NO: 68 and a human kappa light chain constant domain. In one embodiment, said inert reference monoclonal antibody comprises in the heavy chain Fc-region the mutations L234A, L235A and P329G (numbering according to Kabat EU index).

In one embodiment, said inert reference monoclonal antibody comprises a heavy chain with the amino acid sequence of SEQ ID NO: 69 and a light chain with the amino acid sequence of SEQ ID NO: 70.

Comparative Methods and Results
Comparative Technical Approach:
Correction by Residual Blood Volume without Perfusion Friden et al. (J. Cerebral Blood Flow & Met 30 (2010) 150-161) collected the available information from literature on brain vascular space (cf. Table 1 of Friden et al.).

Based on the most commonly used 14C-Dextran method, brain plasma value would amount for approx. 18.1 µL/g brain tissue. When applying this correction all determined values became negative.

Thus, simply assuming that the total brain plasma value would be present in a brain tissue sample was not correct.

Thus, no absolute value could be applied but a co-determined correction factor was required.

Thus, a different correction factor was required.

As perfusion will be performed, a control for remaining blood contamination is required. This is especially important for the comparator IgG or brain shuttles with clearance approaching that of an IgG—why? Because slowly clearing molecules maintain a high concentration in the blood, and if the amount is comparatively very small in the brain, then a small amount of blood contamination can overwhelm the determination of brain concentrations.

Thus, there is the need to use a quantitative blood correction marker that does not significantly diffuse during the application as well as the perfusion phase in to the brain.

Comparative Markers:

Different other non-antibody inert reference molecules, which were, prior to their testing, deemed to be likewise suitable as a corrective means in the method according to the current invention are other endogenous proteins with high molecular weight and high endogenous blood levels.

Determination of Complement Factor H

Different publications indicated that in cynomolgus cerebrospinal fluid (liquor cerebrospinalis) as well as cynomolgus brain lysates no complement factor H is present, wherein it is common in non-CSF or non-brain tissue. Therefore, it has been assumed that the detection of complement factor H is a viable surrogate marker for the determination of residual contaminating blood in cCSF and CBL samples.

As positive controls human pooled serum (HPS; 200-800 µg/mL complement factor H) and human pooled plasma (HPP; about 300 µg/mL complement factor H) were available.

The assay was set-up as an Elecsys-assay (Roche Diagnostics GmbH, Mannheim, Germany). The respective calibration curve is shown in FIG. 7. The working range of this assay was between 7.8 µg/mL and 2000 µg/mL.

| sample | | | µg/mL |
|---|---|---|---|
| positive control | human pooled plasma | | 322 |
| | human pooled serum | | 324 |
| 1 | cynomolgus pooled serum | | 1.4 |
| 2 | cynomolgus pooled plasma 1 | | 1.4 |
| 3 | cynomolgus pooled plasma 2 | | 1.4 |
| 4 | animal 01 | HH8061813 | 1.2 |
| 5 | animal 02 | HH8061813 | 1.2 |
| 6 | animal 12 | HH7061813 | 1.2 |
| 7 | animal 07 | HH7061813 | 1.0 |
| 8 | animal 08 | HH7061813 | 1.0 |
| 9 | cynomolgus pooled plasma 1 | | 1.1 |
| 10 | cynomolgus pooled plasma 2 | | 1.3 |
| 11 (replica of 1) | cynomolgus pooled serum | | 1.5 |
| negative control | cynomolgus brain lysate animal 1 | | blank value |
| | cynomolgus brain lysate animal 2 | | blank value |
| | cynomolgus cerebrospinal fluid | | blank value |

Thus, it has been found that the determination of complement factor H is not suited as surrogate marker for residual contaminating blood as the assay is not sensitive enough.

Determination of Alpha-2-Macroglobulin

Different publications indicated that in cynomolgus cerebrospinal fluid (liquor cerebrospinalis) as well as cynomolgus brain lysates no $\alpha$2-macroglobulin is present, wherein it is common in non-CSF or non-brain tissue (1500-2000 µg/mL). Therefore, it has been assumed that the detection of $\alpha$2-macroglobulin is a viable surrogate marker for the determination of residual contaminating blood in cCSF and CBL samples.

The assay principle of the ELISA-assay for the determination $\alpha$2-macroglobulin is shown in FIG. 8 and a respective calibration curve in FIG. 9.

The assay had a working range from 0.62 ng/mL (LLOQ) to 39 ng/mL (ULOQ).

| | |
|---|---|
| human pooled serum | 2.8 g/l |
| cynomolgus pooled serum 1 | 36 ng/ml |
| cynomolgus pooled serum 2 | 44 ng/ml |
| cynomolgus brain lysate sample | 0 ng/ml |

The expected values for human serum and plasma could be confirmed whereas in cynomolgus pooled serum only $1/25,000$ of the expected amount could be detected. Thus, this value is too low to be quantified in diluted form in cynomolgus cerebrospinal fluid and brain lysates. Thus, the determination of $\alpha$2-macroglobulin is not suited as surrogate marker.

Determination of Complement Component 5a (C5a)

Different publications indicated that in cynomolgus cerebrospinal fluid (liquor cerebrospinalis) as well as cynomolgus brain lysates no complement component 5a is present, wherein it is common in non-CSF or non-brain tissue (60-110 µg/mL in human serum) Therefore, it has been assumed that the detection of complement component C5a is a viable surrogate marker for the determination of residual contaminating blood in cCSF and CBL samples.

Like for $\alpha$2-macroglobulin an ELISA has been set-up with a murine anti-human C5a antibody as capture antibody and a biotinylated murine anti-human C5a antibody as detection antibody, whereby both antibodies bind to non-interfering epitopes on human C5a. A respective calibration curve is shown in FIG. 10.

The assay had a working range from 0.03 ng/mL (LLOQ) to 2 ng/mL (ULOQ).

| | final concentration in matrix |
|---|---|
| human pooled serum | 57 µg/mL |
| human pooled plasma | 24.5 µg/mL |
| cynomolgus pooled serum 1 | 52 µg/mL |
| cynomolgus pooled serum 2 | 70 µg/mL |
| cynomolgus brain lysate | 11 µg/mL |

Thus, it has been found that C5a can be determined in CBL samples.

Thus, the determination of C5a is not suited as surrogate marker.

Use of Magnevist®

Magnevist® (gadopentetat-dimeglumin) is a MRT-imaging agent. It was assumed that Magnevist® will not passage the blood-brain-barrier.

A pharmacokinetic study showed that up to 15 minutes only the measured brain concentration represents the blood compartment correctly. After this time, there is diffusion of Magnevist® into the brain tissue, confounding the applied correction. The respective time-course is shown in FIG. 11. At the 5-minute time point, plasma volume is estimated as 14.1 µL/g brain.

Thus, this approach cannot be sued with perfusion, as the time taken for perfusion would lead to a diffusion of Magnevist across the blood-brain-barrier—confounding the residual blood correction.

Determination of Cynomolgus IgG in Cynomolgus Cerebrospinal Fluid (cCSF)

Different publications indicated that in cynomolgus cerebrospinal fluid (liquor cerebrospinalis) only minor amounts of cynomolgus IgG are present. Therefore, it has been assumed that the detection of total Ig in cCSF is a viable surrogate marker for the direct determination of transported therapeutic antibody. Therefore, a bridging ELISA was set up as shown in FIG. 12. To exclude matrix effects a human IgG-depleted cCSF was generated by incubating the cCSF with anti-human CH1/kappa antibody bound to magnetic beads.

The respective calibration curves with buffer and human IgG-depleted cCSF are shown in FIG. 13. It can be seen that no matrix effect occurs.

The assay had a working range of from 120 ng/ml to 7.2 ng/mL IgG.

Using this assay it has been found that in cynomolgus pooled plasma samples (CPP) about 11-19 mg/mL IgG could be detected, whereas in cCSF samples substantial amounts of about 4-18 µg/mL cynomolgus IgG could be detected.

The following examples, sequences and figures are provided to aid the understanding of the present invention, the true scope of which is set forth in the appended claims. It is understood that modifications can be made in the procedures set forth without departing from the spirit of the invention.

| SEQ ID NO | description |
|---|---|
| 01 | human Aβ42 |
| 02 | (G4S)4 linker |
| 03 | (G4S)6G2 linker |
| 04 | mAh 0012 |
| 05 | mAh 0012 |
| 06 | mAh 0012 |
| 07 | mAh 0012 |
| 08 | mAh 0015 |
| 09 | mAh 0015 |
| 10 | mAh 0015 |
| 11 | mAh 0015 |
| 12 | mAh 0020 |
| 13 | mAh 0020 |
| 14 | mAh 0020 |
| 15 | mAh 0024 |
| 16 | mAh 0024 |
| 17 | mAh 0024 |
| 18 | mAh 0024 |
| 19 | A-beta binding site VH |
| 20 | A-beta binding site VL |
| 21 | transferrin receptor binding site VH |
| 22 | transferrin receptor binding site VL |
| 23 | light chain |
| 24 | heavy chain |
| 25 | light chain |
| 26 | heavy chain Fab fragment |
| 27 | anti-transferrin receptor antibody 128.1 VH |
| 28 | anti-transferrin receptor antibody 128.1 VL |
| 29 | heavy chain variable domain |
| 30 | light chain variable domain |
| 31 | anti-transferrin receptor binding site VH |
| 32 | anti-transferrin receptor binding site VL |
| 33 | the anti-transferrin receptor binding site HVR-H1 |
| 34 | the anti-transferrin receptor binding site HVR-H2 |
| 35 | the anti-transferrin receptor binding site HVR-H3 |
| 36 | the anti-transferrin receptor binding site HVR-H3 |
| 37 | the anti-transferrin receptor binding site HVR-H3 |
| 38 | the anti-transferrin receptor binding site HVR-L1 |
| 39 | the anti-transferrin receptor binding site HVR-L2 |
| 40 | the anti-transferrin receptor binding site HVR-L3 |
| 41 | heavy chain variable domain anti-CD20 antibody |
| 42 | light chain variable domain anti-CD20 antibody |
| 43 | heavy chain variable domain anti-alpha synuclein (asyn) antibody |
| 44 | light chain variable domain anti-alpha synuclein antibody |
| 45 | heavy chain variable domain anti-alpha synuclein antibody |
| 46 | light chain variable domain anti-alpha synuclein antibody |
| 47 | heavy chain variable domain anti-alpha synuclein antibody |
| 48 | light chain variable domain anti-alpha synuclein antibody |
| 49 | heavy chain variable domain anti-alpha synuclein antibody |
| 50 | light chain variable domain anti-alpha synuclein antibody |
| 51 | heavy chain variable domain anti-alpha synuclein antibody |
| 52 | light chain variable domain anti-alpha synuclein antibody |
| 53 | heavy chain variable domain anti-alpha synuclein antibody |
| 54 | light chain variable domain anti-alpha synuclein antibody |
| 55 | glucocerebrosidase |
| 56 | peptidic linker |
| 57 | peptidic linker |
| 58 | brain target |
| 59 | brain target |
| 60 | brain target |
| 61 | brain target |
| 62 | the anti-transferrin receptor binding site HVR-H1 |
| 63 | the anti-transferrin receptor binding site HVR-H2 |
| 64 | the anti-transferrin receptor binding site HVR-H3 |
| 65 | the anti-transferrin receptor binding site HVR-L1 |
| 66 | the anti-transferrin receptor binding site HVR-L3 |
| 67 | heavy chain variable region sequence DP47GS |
| 68 | light chain variable region sequence DP47GS |
| 69 | inert reference monoclonal antibody comprises a heavy chain |
| 70 | inert reference monoclonal antibody comprises a light chain |

GENERAL METHODS

Preparation of Cynomolgus Brain Tissue Homogenates

Figure 1:
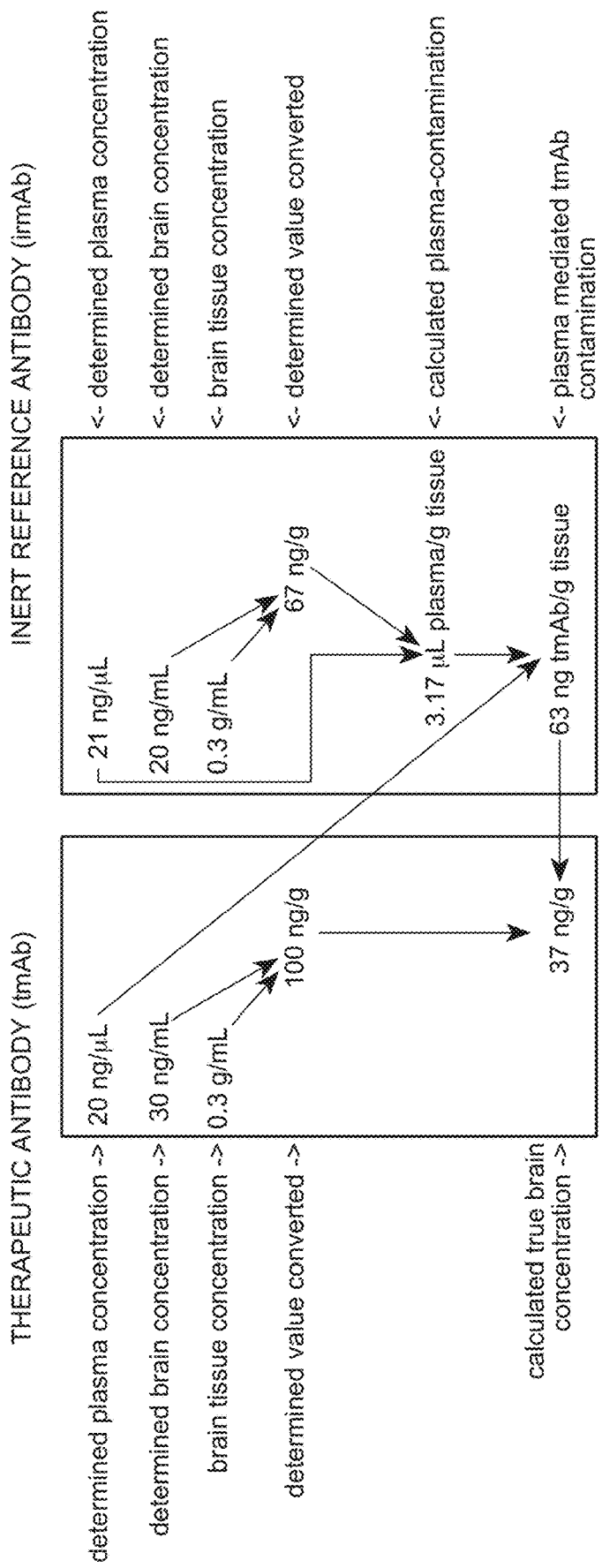
FIG. 1 Exemplary calculation for determining residual-plasma-corrected brain lysate concentration of a tmAb.
Figure 2:
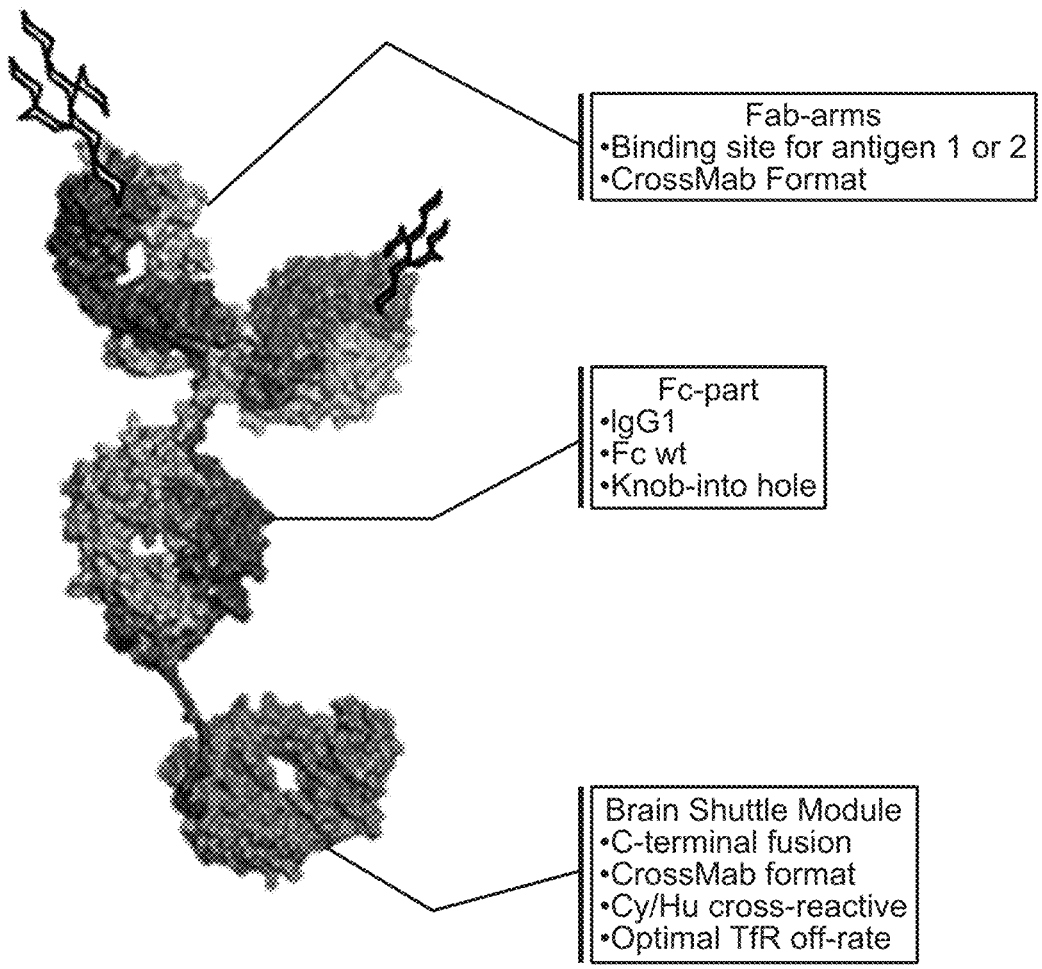
FIG. 2 Structure of the exemplary brain-shuttle construct used in the examples of the method according to the invention.
Figure 3:
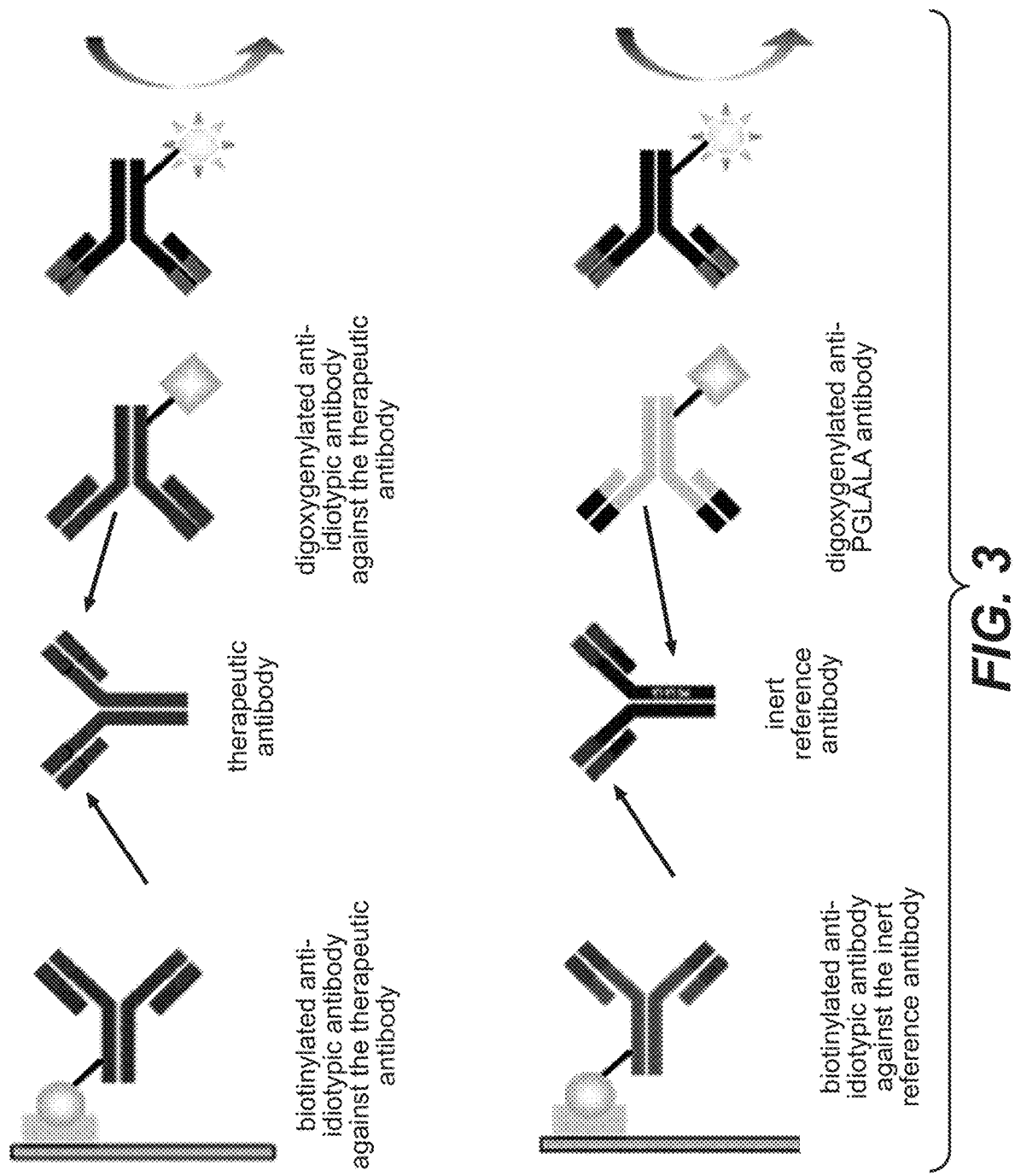
FIG. 3 Detection assay for therapeutic antibody and reference antibody used in the Examples.
Figure 4:
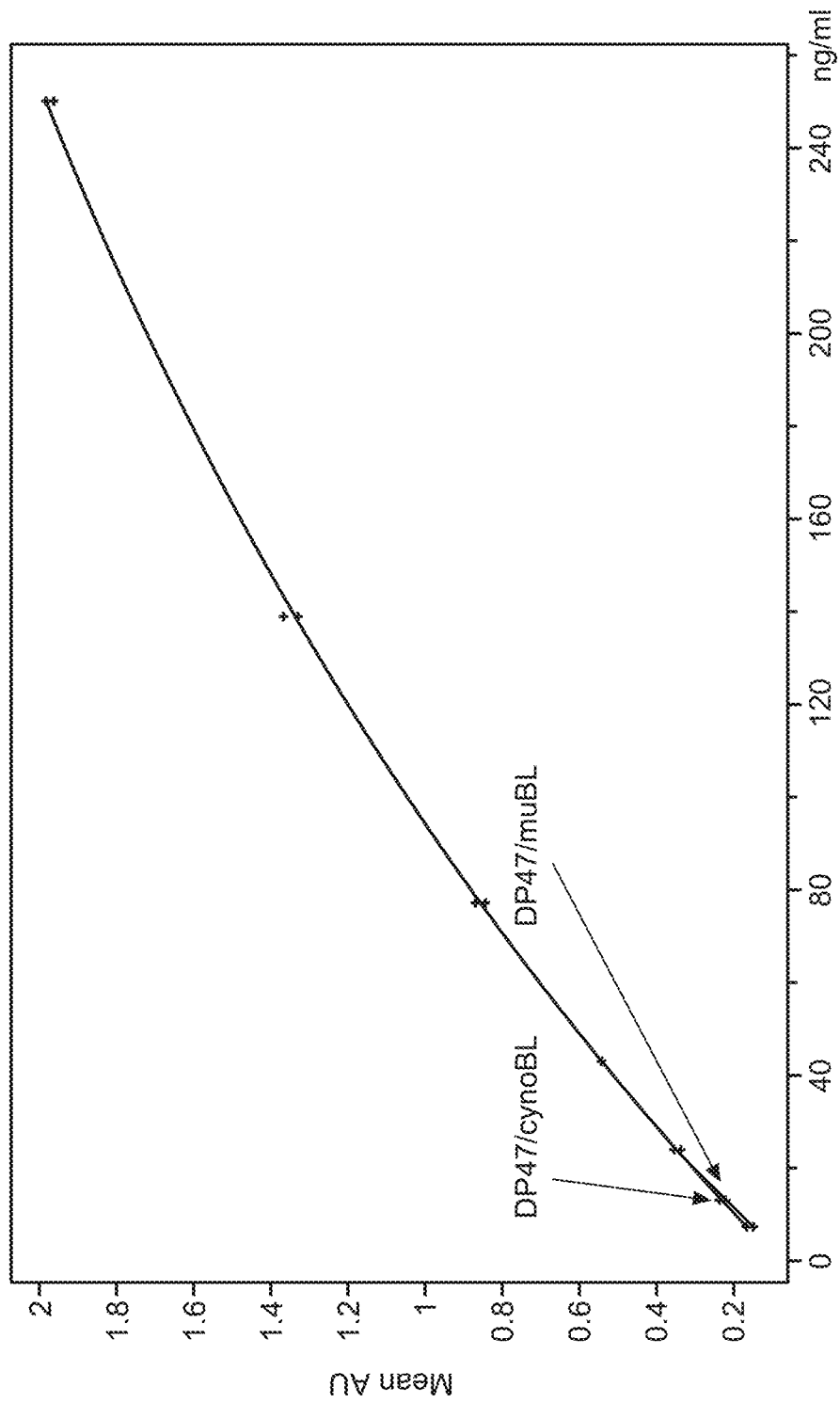
FIG. 4 Overlay of the calibration curves of the detection assay according to Example 1 for the inert reference antibody in the presence of 1% cynomolgus and mouse, respectively, brain lysate.
Figure 5:
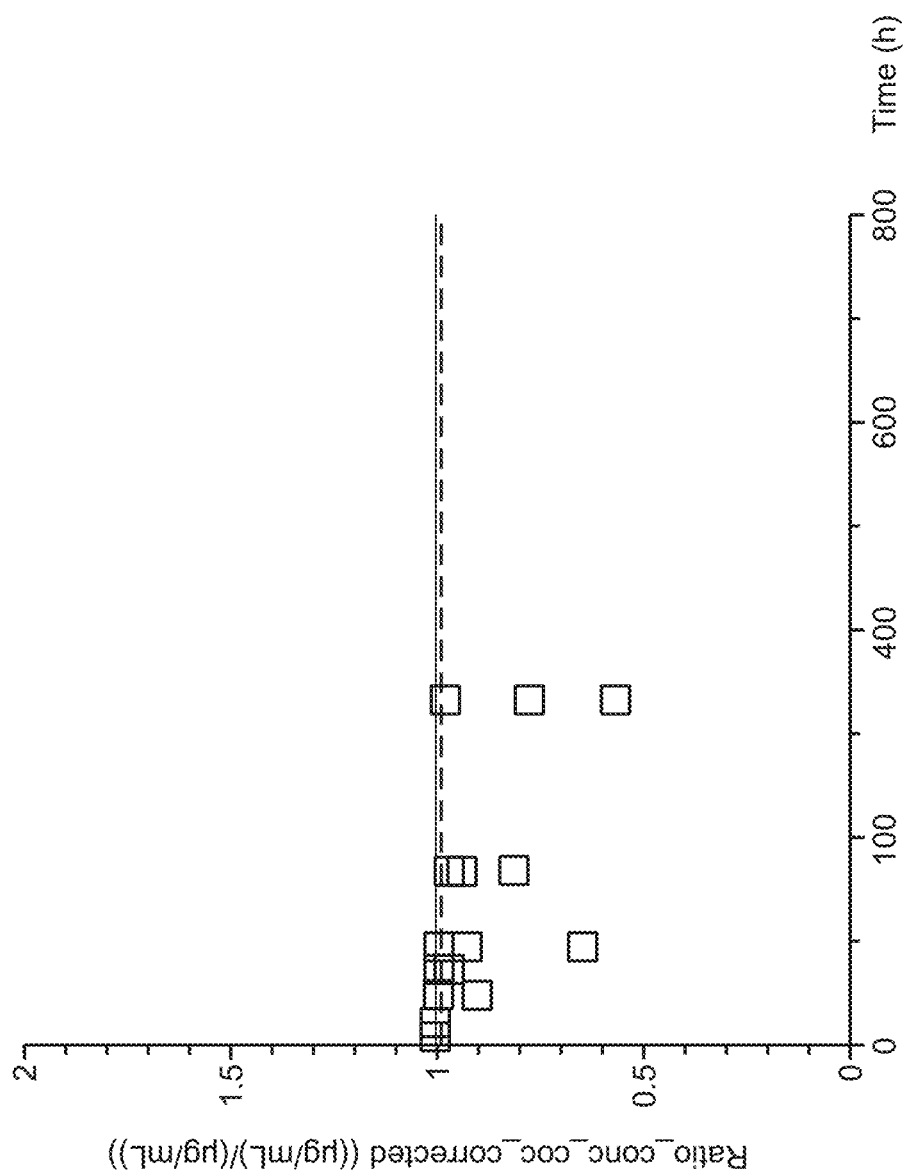
FIG. 5 Ratio of corrected concentration to non-corrected concentration of antibody 2 in mouse brain lysate.
Figure 6:
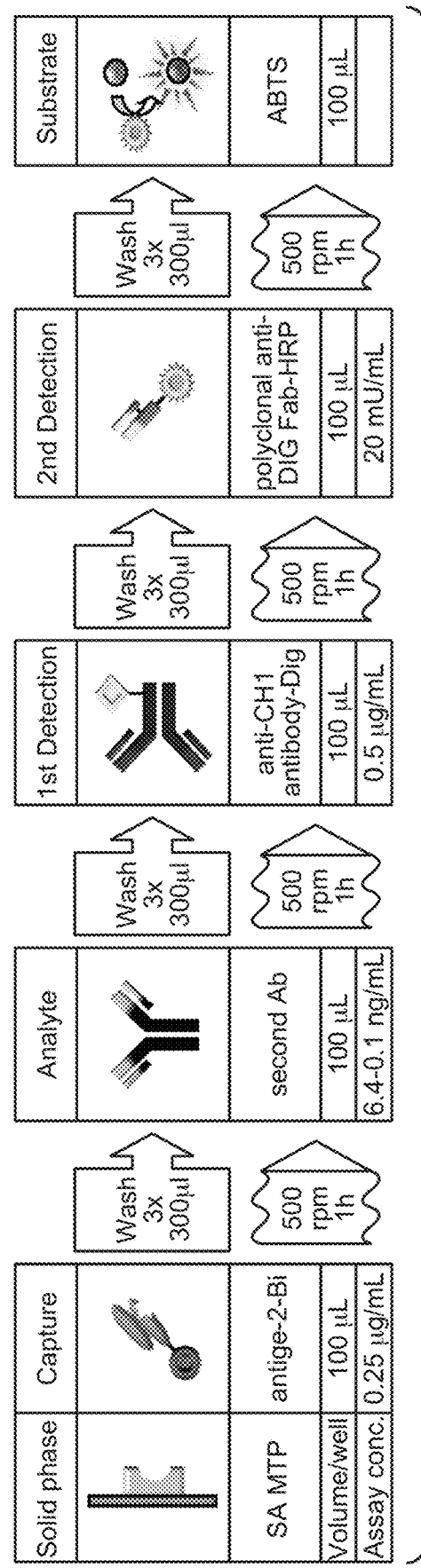
FIG. 6 ELISA for the determination of antibody 2.
Figure 7:
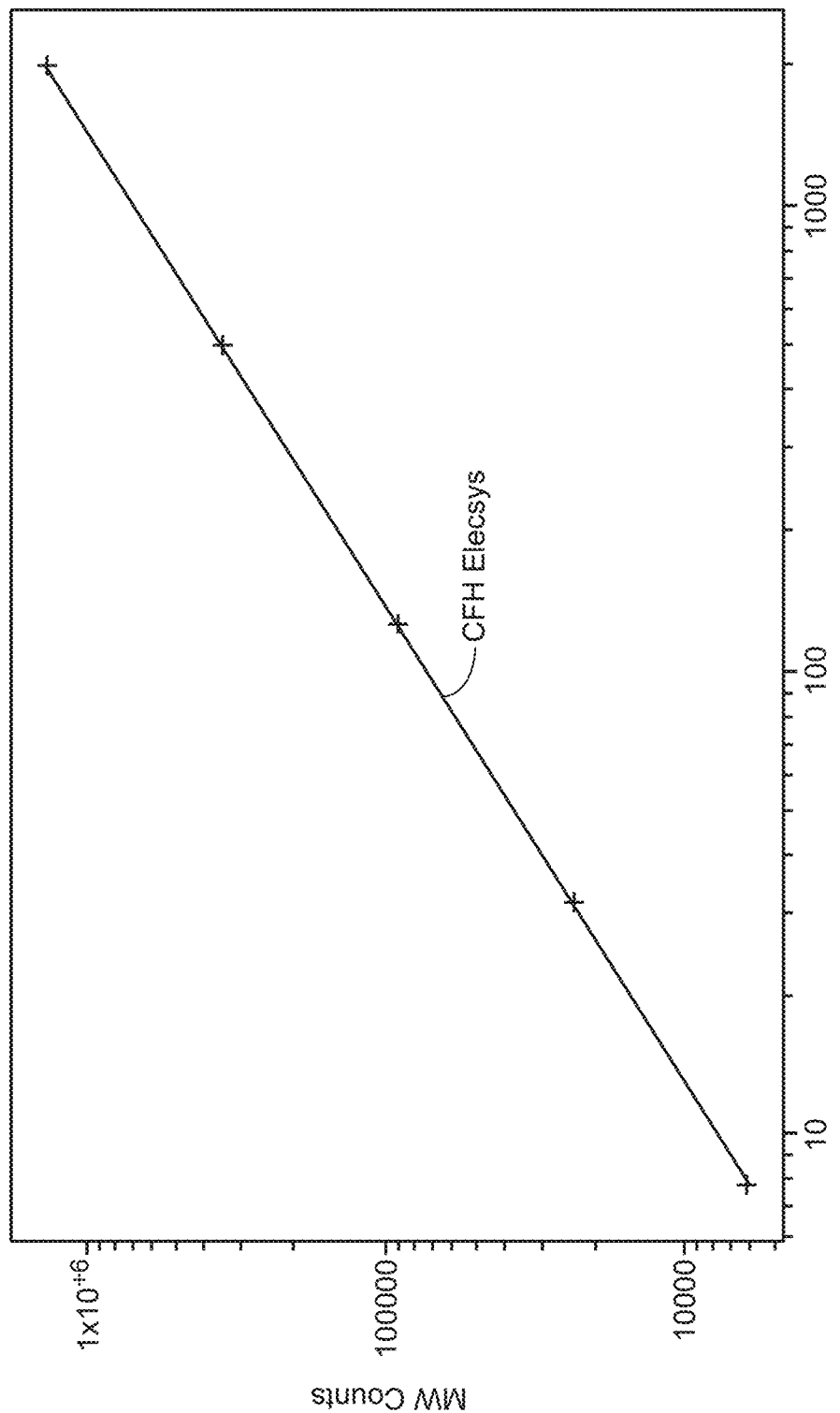
FIG. 7 Calibration curve of complement factor H Elecsys assay.
Figure 8:
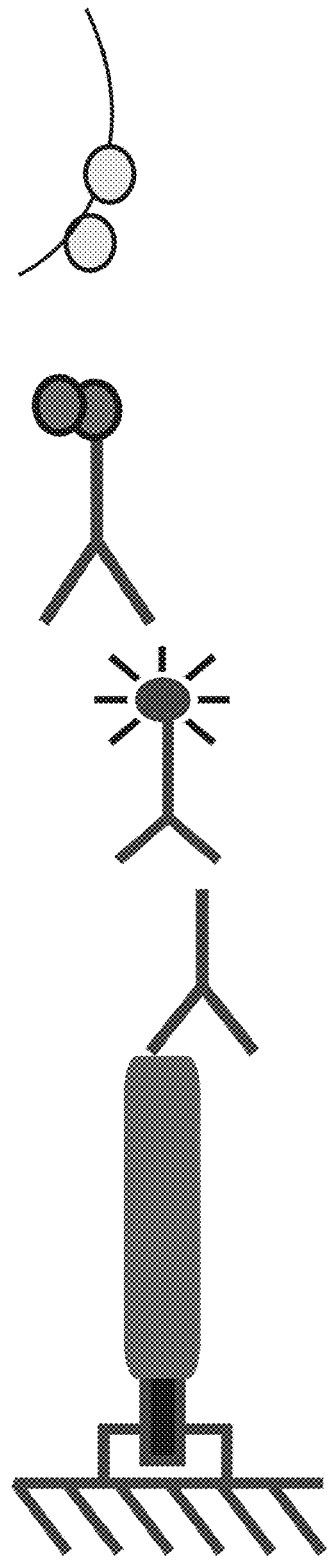
FIG. 8 ELISA for the quantification of α2-macroglobulin in cCSF. The capture antibody is a murine anti-human α2-macroglobulin antibody; the detection antibody is a biotinylated goat anti-human α2-macroglobulin antibody.
Figure 9:
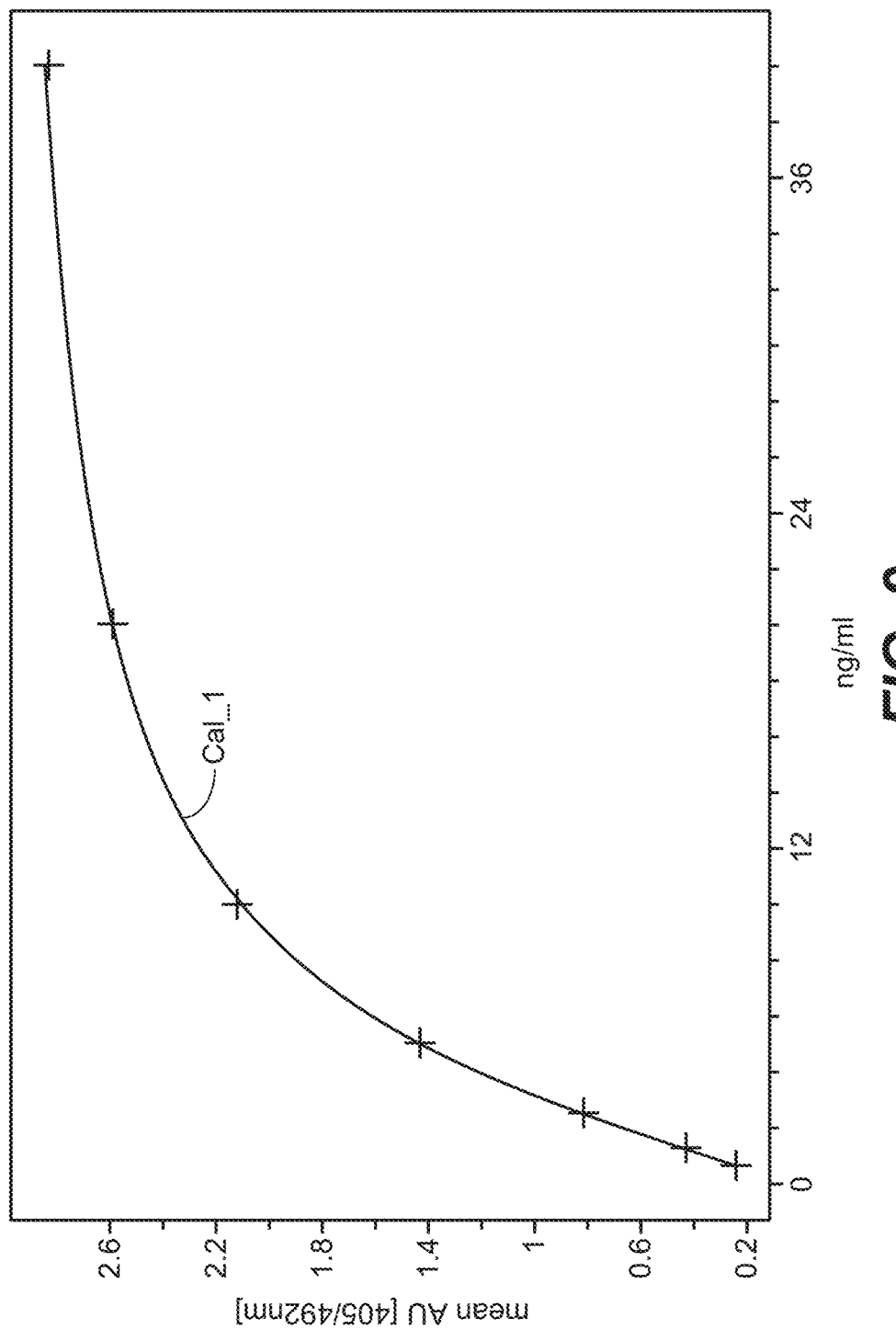
FIG. 9 Calibration curve of the ELISA of FIG. 8.
Figure 10:
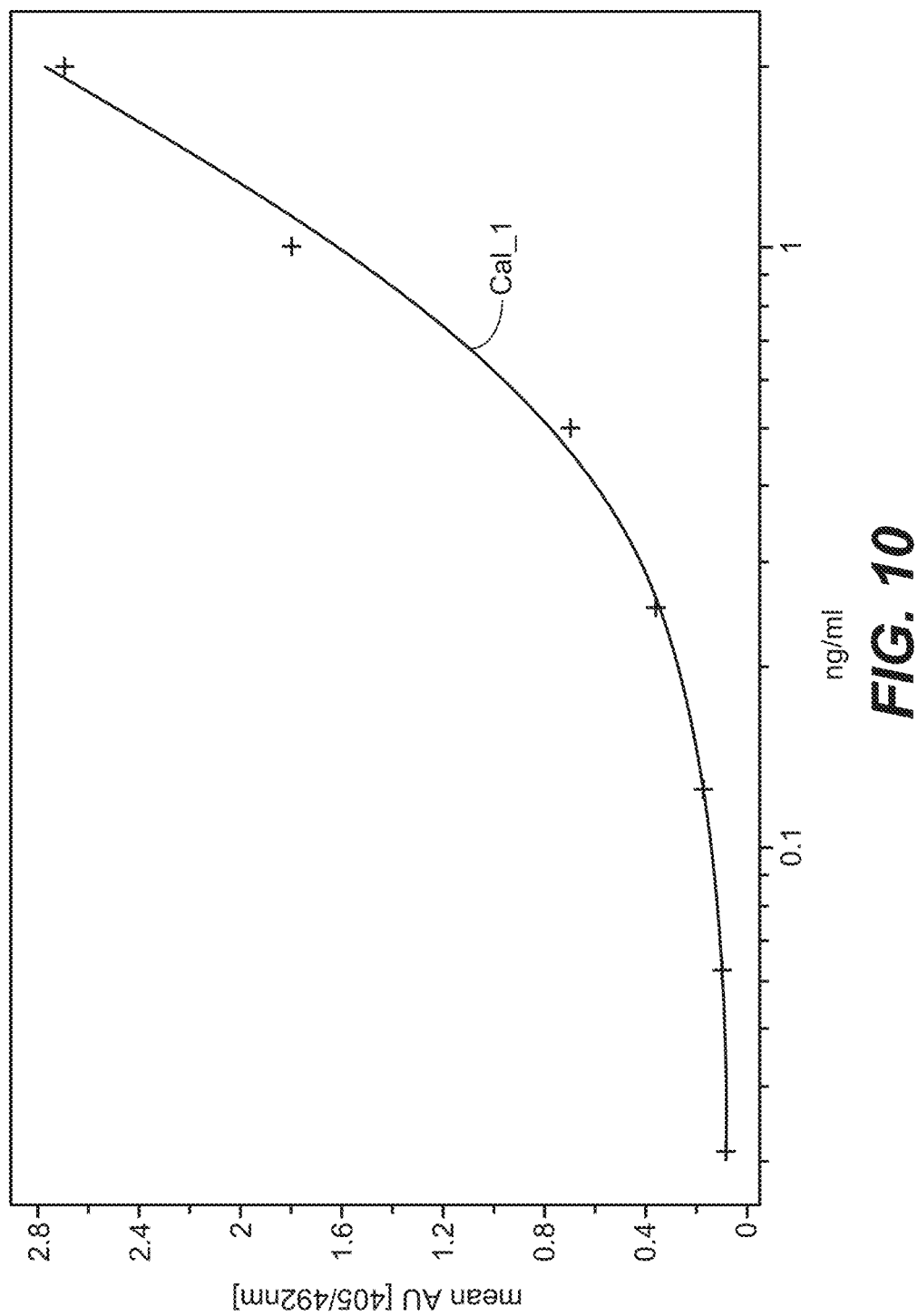
FIG. 10 Calibration curve of complement component 5a ELISA assay.
Figure 11:
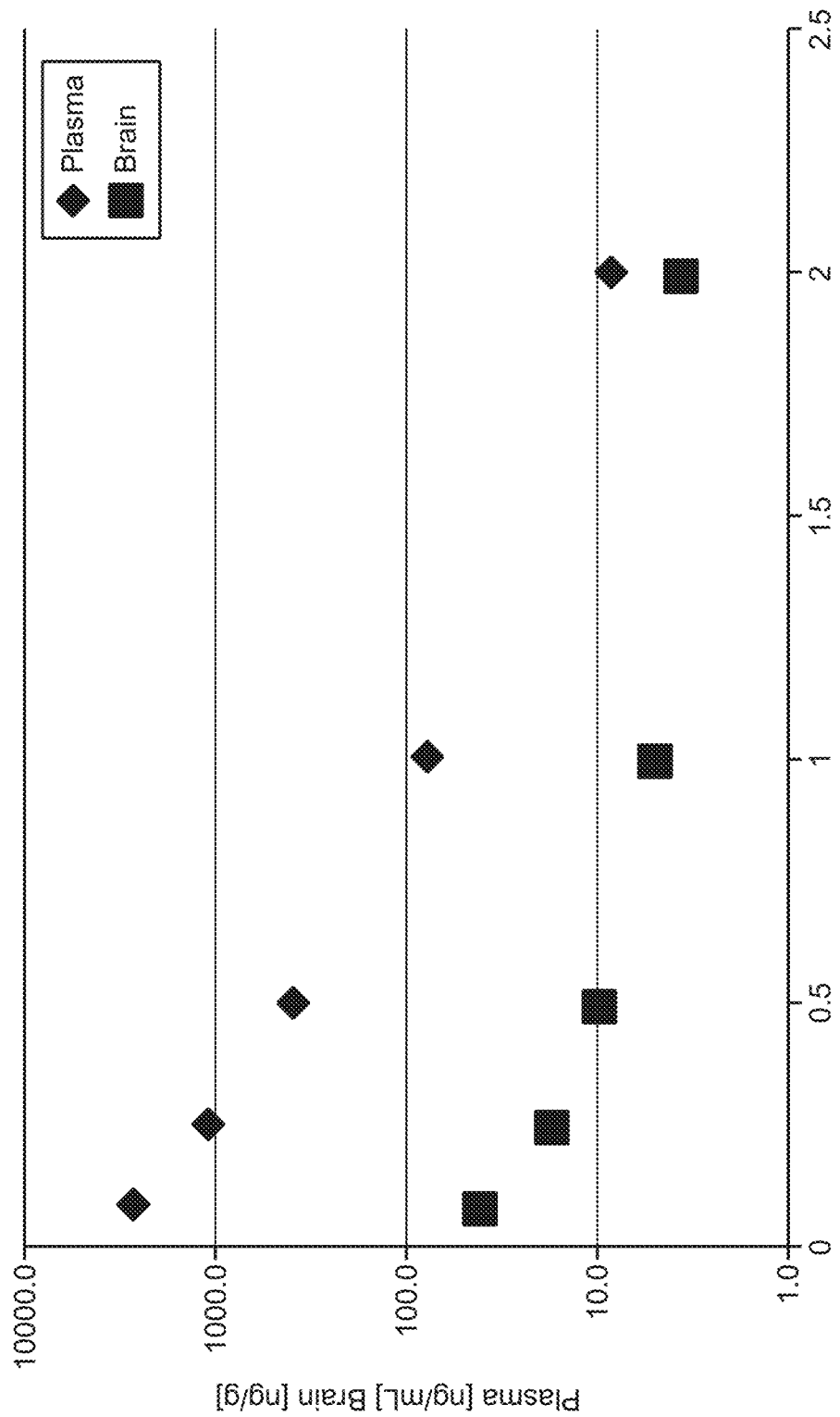
FIG. 11 Time course of Magnevist in PK study in plasma and brain tissue.
Figure 12:
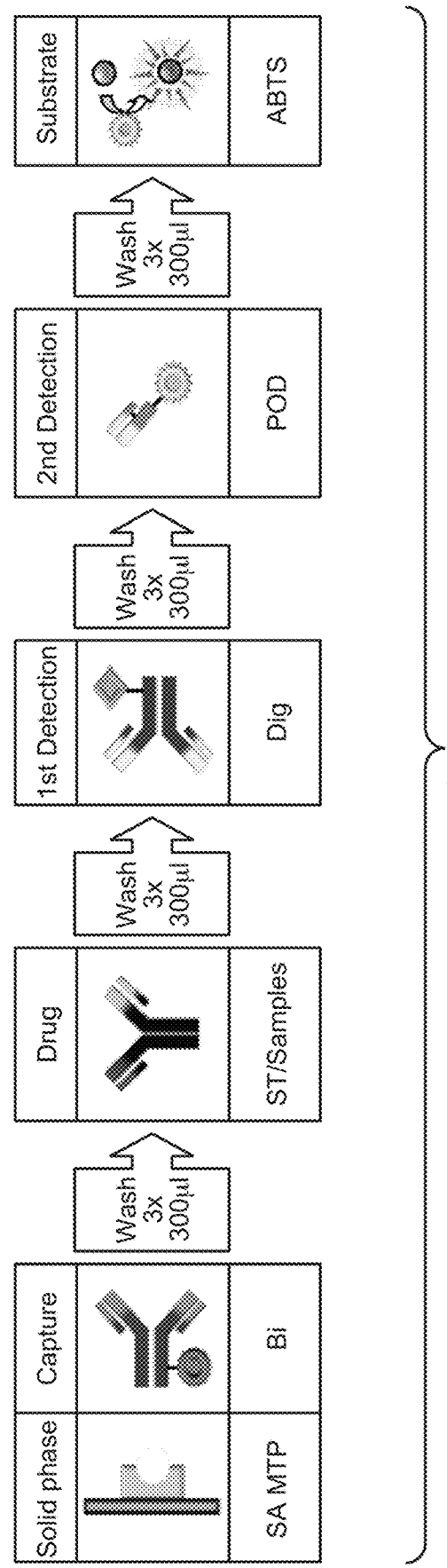
FIG. 12 ELISA for the quantification of cynomolgus IgG in cCSF. The capture mAb is an anti-cyno IgG antibody; the detection mAb is an anti-cyno IgG antibody binding to a not interference epitope with respect to the first antibody.
Figure 13:
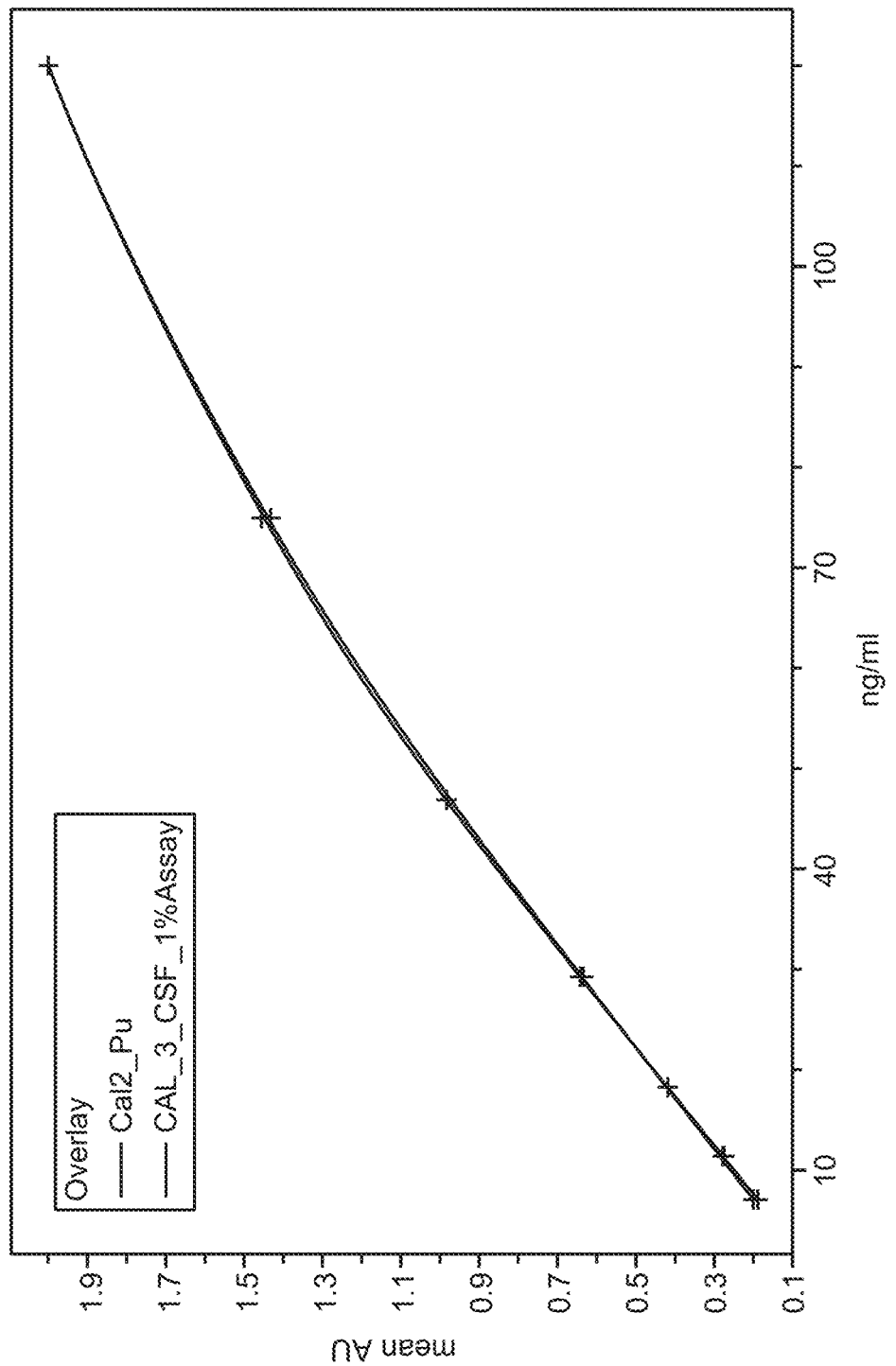
FIG. 13 Calibration curve of the ELISA of FIG. 12.

Frozen cynomolgus/mouse brain tissue samples of 300 mg were thawed at room temperature for 2 h. 800 µL of lysis buffer, one tablet of cOmplete protease inhibitor cocktail (Roche Diagnostics GmbH) dissolved in 50 mL Tissue Extraction Reagent I (Invitrogen), were added to the thawed brain tissue. Next, the sample was homogenized in a MagNA Lyser instrument (Roche Diagnostics) for 20 seconds at 6500 rpm. The tissue homogenate was then centrifuged for 10 minutes at 12,000 rpm using a Centrifuge 5430 (Eppendorf). Finally, the supernatant was transferred to a 1.5 mL vial for further analysis or stored at −80° C.

Example 1

ELISA for the Quantification of DP47GS-PGLALA in Brain Lysates

To quantify the inert reference monoclonal antibody DP47GS-PGLALA (SEQ ID NO: 69 and 70) in cynomolgus brain lysate samples a serial sandwich enzyme linked immunosorbent assay (ELISA) was used. In the ELISA procedure, all samples and controls are subjected to an initial 1:100 pre-dilution in Assay Diluent to the desired 1% final assay concentration.

Capture Antibody (anti-DP47GS antibody, biotinylated), diluted Calibrators (DP47GS-PGLALA) as well as diluted Quality controls and samples, detection reagent (anti-PGLALA antibody clone M-1.7.24, digoxygenylated) and anti-digoxygenin-antibody-POD-conjugate are added successively to a streptavidin coated microtiter plate (SA-MTP). The reagents were incubated for 1 hour on a MTP shaker at 500 rpm and after each step the MTP was washed three times with 300 µL washing buffer (1×PBS, 0.05% Tween) and residual fluids were removed. After that, the formed immobilized immune complexes were visualized by addition of ABTS solution, a horseradish POD substrate, which was converted to a colored reaction product. Finally, the color intensity was photometrically determined (absorption at 405 nm-490 nm reference wavelength). The signal is proportional to the analyte concentration in the brain lysate sample. The quantification of DP47GS-PGLALA was performed by back calculation of the absorbance values using the corresponding calibration curve with a non-linear 4-parameter Wiemer-Rodbard curve fitting function with weighting.

| Quality control | Calculation | brain lysate concentration DP47GS-PGLALA [ng/mL] | assay concentration DP47GS-PGLALA [ng/mL] |
|---|---|---|---|
| ULQC Upper limit of quantification | highest calibrator | 250 | 2.5 |
| HQC High range | highest calibrator × 0.75 | 185 | 1.85 |
| MQC Medium range | geometric mean of HQC and LQC | 80 | 0.80 |
| LQC Low range | LLQC × 3 | 25 | 0.25 |
| LLQC Lower limit of quantification | lowest calibrator | 8 | 0.08 |

Coating with capture reagent is achieved by pipetting 100 µL of a solution comprising 500 ng/mL biotinylated anti-DP47GS antibody into each SA-MTP well. Thereafter the MTP is covered with adhesive cover foil and incubated for 1 hour on a MTP shaker (500 rpm). The supernatant is removed and each well of the MTP is washed three times with 300 µL washing buffer (PBS, 0.05% Tween). Residual washing buffer is carefully removed.

Then 100 µl of the respective calibrators, quality controls and samples to the designated wells of the coated MTP. Thereafter the MTP is covered with adhesive cover foil and incubated for 1 hour on a MTP shaker (500 rpm). The supernatant is removed and each well of the MTP is washed three times with 300 µL washing buffer (PBS, 0.05% Tween). Residual washing buffer is carefully removed.

Then 100 µL of digoxygenylated anti-PGLALA antibody clone M-1.7.24 at a concentration of 125 ng/mL is added to each MTP well. Thereafter the MTP is covered with adhesive cover foil and incubated for 1 hour on a MTP shaker (500 rpm). The supernatant is removed and each well of the MTP is washed three times with 300 µL washing buffer (PBS, 0.05% Tween). Residual washing buffer is carefully removed.

The 100 µL of an anti-digoxygenin antibody-POD-conjugate at a concentration of 50 mU/mL is added to each MTP well. Thereafter the MTP is covered with adhesive cover foil and incubated for 1 hour on a MTP shaker (500 rpm). The supernatant is removed and each well of the MTP is washed three times with 300 µL washing buffer (PBS, 0.05% Tween). Residual washing buffer is carefully removed.

Then 100 µL ABTS solution is added to each MTP well. The optical density is measured until the average signal of the duplicates of Calibrator sample 1 reaches 1.8-2.2 AU at a measuring wavelength of 405 nm (reference wavelength 490 nm).

Example 2

ELISA for the Quantification of Cynomolgus IgG in CSF

To quantify cynomolgus IgG in cynomolgus cerebrospinal fluid a serial sandwich enzyme linked immunosorbent assay (ELISA) was used. In the ELISA procedure, all samples and controls are subjected to an initial pre-dilution in Assay Diluent to the desired 1% final assay concentration.

Capture Antibody (anti-cynomolgus IgG antibody 1; epitope 1; biotinylated), diluted Calibrators as well as diluted Quality controls and samples, detection reagent (anti-cynomolgus IgG antibody 2; epitope 2, not interfering with epitope 1; digoxygenylated) and anti-digoxygenin-antibody-POD-conjugate are added successively to a streptavidin coated microtiter plate (SA-MTP). The reagents were incubated for 1 hour on a MTP shaker at 500 rpm and after each step the MTP was washed three times with 300 μL washing buffer (1×PBS, 0.05% Tween) and residual fluids were removed. After that, the formed immobilized immune complexes were visualized by addition of ABTS solution, a horseradish POD substrate, which was converted to a colored reaction product. Finally, the color intensity was photometrically determined (absorption at 405 nm-490 nm reference wavelength). The signal is proportional to the analyte concentration in the brain lysate sample. The quantification of cynomolgus IgG was performed by back calculation of the absorbance values using the corresponding calibration curve with a non-linear 4-parameter Wiemer-Rodbard curve fitting function with weighting.

| Quality control | Calculation | cCSF concentration cynomolgus IgG [ng/mL] | assay concentration cynomolgus IgG [ng/mL] |
|---|---|---|---|
| ULQC Upper limit of quantification | highest calibrator | 12000 | 120 |
| HQC High range | highest calibrator × 0.75 | 9000 | 90 |
| MQC Medium range | geometric mean of HQC and LQC | 45000 | 45 |
| LQC Low range | LLQC × 3 | 2200 | 22 |
| LLQC Lower limit of quantification | lowest calibrator | 720 | 7.2 |

Coating with capture reagent is achieved by pipetting 100 μL of a solution comprising 250 ng/mL biotinylated anti-cynomolgus IgG antibody 1 into each SA-MTP well. Thereafter the MTP is covered with adhesive cover foil and incubated for 1 hour on a MTP shaker (500 rpm). The supernatant is removed and each well of the MTP is washed three times with 300 μL washing buffer (PBS, 0.05% Tween). Residual washing buffer is carefully removed.

Then 100 μl of the respective calibrators, quality controls and samples to the designated wells of the coated MTP Thereafter the MTP is covered with adhesive cover foil and incubated for 1 hour on a MTP shaker (500 rpm). The supernatant is removed and each well of the MTP is washed three times with 300 μL washing buffer (PBS, 0.05% Tween). Residual washing buffer is carefully removed.

Then 100 μL of digoxygenylated anti-cynomolgus antibody 2 at a concentration of 250 ng/mL is added to each MTP well. Thereafter the MTP is covered with adhesive cover foil and incubated for 1 hour on a MTP shaker (500 rpm). The supernatant is removed and each well of the MTP is washed three times with 300 μL washing buffer (PBS, 0.05% Tween). Residual washing buffer is carefully removed.

The 100 μL of an anti-digoxygenin antibody-POD-conjugate at a concentration of 25 mU/mL is added to each MTP well. Thereafter the MTP is covered with adhesive cover foil and incubated for 1 hour on a MTP shaker (500 rpm). The supernatant is removed and each well of the MTP is washed three times with 300 μL washing buffer (PBS, 0.05% Tween). Residual washing buffer is carefully removed.

Then 100 μL ABTS solution is added to each MTP well. The optical density is measured until the average signal of the duplicates of Calibrator sample 1 reaches 1.8-2.2 AU at a measuring wavelength of 405 nm (reference wavelength 490 nm).

Example 3

Production of Brain Tissue Lysates

First, the lysis buffer was freshly prepared according to the manufacturer's instructions (Invitrogen; tissue extraction reagent I; Cat.-No. FNN0071). Per 50 ml of lysis buffer 1 tables of Complete is added (Roche Diagnostics GmbH, Mannheim, Germany; Cat.-No. 11697498001).

Second, to the brain tissue sample, approx. 100-300 mg, between 600 μL and 800 μL were lysis buffer is added. Optionally MagNA Lyser Green Beads are added.

Third, the samples were placed for 20 sec. at 6500 rpm in the MagNA Lyser (Roche Diagnostics GmbH, Mannheim, Germany).

Fourth, after incubation in the MagNA Lyser the samples are centrifuged for 10 min. at 12,000 rpm (Eppendorf Centrifuge 5430).

Fifth, the supernatant (500-700 μL) was recovered and stored at −80° C. until further analysis.

What is claimed is:

1. A method for determining the concentration of a therapeutic antibody in a tissue of an experimental animal, whereby the tissue has a barrier to the blood circulation of said animal and whereby the therapeutic antibody had been administered to said experimental animal, wherein the interference from residual blood in a tissue sample of the experimental animal, which is used for determining the concentration of the therapeutic antibody in said tissue, is reduced, the method comprising the following steps of administering a therapeutic antibody and an inert reference antibody to the experimental animal, i) determining the concentration of the therapeutic antibody in a blood sample of the experimental animal, ii) determining the concentration of the therapeutic antibody in the tissue sample of the experimental animal, iii) determining the concentration of an inert reference antibody in the blood sample of the experimental animal, iv) determining the concentration of the inert reference antibody in the tissue sample of the experimental animal, v) determining the tissue concentration in the tissue sample, and determining the concentration of the therapeutic antibody in the tissue of the experimental animal with the following formula:

$$C_{tmAb,tissue} = \frac{C_{tmAb,tissue,det.}}{C_{tissue,sample}} - \frac{\frac{C_{refmAb,tissue,det.}}{C_{tissue,sample}}}{C_{refmAb,plasma,det.}} * C_{tmAb,plasma,det.}$$

with $C_{tmAb,plasma,det.}$=concentration of the therapeutic antibody of i)

$C_{tmAb,tissue,det.}$=concentration of the therapeutic antibody of ii)

$C_{refmAb,tissue,det.}$=concentration of the inert reference antibody of iii)

$C_{refmAb,plasma,det.}$=concentration of the inert reference antibody of iv)

$C_{tissue,sample}$=tissue concentration of v)

whereby the inert reference antibody does not cross said barrier between the tissue and the blood circulation, whereby the inert reference antibody had been administered i) either together with the therapeutic antibody in case the sample is to be taken within 5 minutes after the administration of the therapeutic antibody, or ii) 2 to 10 minutes prior to taking the tissue sample, whereby the blood sample is taken directly prior to the tissue sample, wherein the inert reference antibody is DP47GS, wherein the inert reference antibody comprises a heavy chain variable region and a light chain variable region, wherein the heavy chain variable region comprises the amino acid sequence of SEQ ID NO: 67 and the light chain variable region comprises the amino acid sequence of SEQ ID NO: 68.

2. The method according to claim 1, wherein the tissue is either brain tissue and the therapeutic antibody can cross the blood-brain-barrier or ocular tissue and the therapeutic antibody can cross the blood-ocular-barrier.

3. The method according to claim 1, wherein the therapeutic antibody is a bispecific antibody.

4. The method according to claim 1, wherein the therapeutic antibody is specifically binding to human transferrin receptor and a brain target.

5. The method according to claim 4, wherein the brain target is selected from the group consisting of human CD20, human Abeta, human alpha-synuclein, human tau, human glucocerebrosidase, human lingo-1, and human huntingtin.

6. The method according to claim 1, wherein the experimental animal is selected from mouse, rat, rabbit, dog, sheep, ape, and monkey.

7. The method according to claim 1, wherein the experimental animal is a non-human experimental animal with a body weight of more than 100 g and less than 15 kg.

8. The method according to claim 1, wherein the experimental animal is a cynomolgus monkey.

9. The method according to claim 1, wherein the inert reference antibody is a human germline antibody.

10. The method according to claim 1, wherein the inert reference antibody does not cross said barrier in detectable amounts within 15 minutes after its application.

11. The method according to claim 10, wherein the inert reference antibody does not cross said barrier in detectable amounts within 10 minutes after its application.

12. The method according to claim 1, wherein the inert antibody is administered about 5 minutes prior to taking the tissue sample.

13. The method according to claim 1, wherein the tissue is perfused with an aqueous solution directly after taking the blood sample and prior to taking the tissue sample.

14. The method according to claim 1, wherein the determining of the concentrations is by a bridging ELISA.

* * * * *